US010351487B2

(12) United States Patent
Smith et al.

(10) Patent No.: US 10,351,487 B2
(45) Date of Patent: Jul. 16, 2019

(54) METHODS FOR CONVERSION OF ETHANOL TO FUNCTIONALIZED LOWER HYDROCARBONS AND DOWNSTREAM HYDROCARBONS

(71) Applicant: Gevo, Inc., Englewood, CO (US)

(72) Inventors: Jonathan O. Smith, Highlands Ranch, CO (US); Nicholas McGuire, Denver, CO (US); Leo E. Manzer, Wilmington, DE (US); Madeline Sjodin, Denver, CO (US); Paul Starkey, Denver, CO (US); Carolina Salazar, Parker, CO (US)

(73) Assignee: GEVO, INC, Englewood, CO (US)

( * ) Notice: Subject to any disclaimer, the term of this patent is extended or adjusted under 35 U.S.C. 154(b) by 0 days.

(21) Appl. No.: 15/519,419

(22) PCT Filed: Oct. 14, 2015

(86) PCT No.: PCT/US2015/055581
§ 371 (c)(1),
(2) Date: Apr. 14, 2017

(87) PCT Pub. No.: WO2016/061262
PCT Pub. Date: Apr. 21, 2016

(65) Prior Publication Data
US 2017/0226028 A1    Aug. 10, 2017

Related U.S. Application Data

(60) Provisional application No. 62/063,829, filed on Oct. 14, 2014, provisional application No. 62/081,817, (Continued)

(51) Int. Cl.
*C07C 1/24* (2006.01)
*C07C 1/20* (2006.01)
(Continued)

(52) U.S. Cl.
CPC .............. *C07C 1/24* (2013.01); *B01J 23/02* (2013.01); *B01J 23/06* (2013.01); *B01J 23/10* (2013.01);
(Continued)

(58) Field of Classification Search
CPC ........... C07C 1/24; C07C 2/10; C07C 45/512; C07C 2521/02; C07C 2521/06
(Continued)

(56) References Cited

U.S. PATENT DOCUMENTS 2,931,787 A    4/1960    Jones et al.
2,981,767 A    4/1961    Gay et al.
(Continued)

FOREIGN PATENT DOCUMENTS

EP    0407811 A2    1/1991
EP    0598243 A2    5/1994
(Continued)

OTHER PUBLICATIONS

Denmark, et al., "Lewis base catalysis in organic synthesis." Angew Chem Int Ed Engl. (2008); 47(9): 1560-1638.
(Continued)

*Primary Examiner* — Fred M Teskin
(74) *Attorney, Agent, or Firm* — Cooley LLP

(57) ABSTRACT

This application relates to the production of functionalized lower hydrocarbons and more particularly to the process of converting ethanol to functionalized lower hydrocarbons. In particular embodiments, the ethanol to functionalized lower hydrocarbon conversion is catalyzed by a $Zn_xZr_yA_vQ_s Mn_wO_z$ mixed oxide catalyst or a bifunctional heterogeneous catalyst. In particular embodiments, the ethanol to be converted is present at molar concentrations in the reactor feed equal to or exceeding 14%.

23 Claims, 6 Drawing Sheets

Related U.S. Application Data filed on Nov. 19, 2014, provisional application No. 62/114,943, filed on Feb. 11, 2015, provisional application No. 62/114,945, filed on Feb. 11, 2015, provisional application No. 62/131,652, filed on Mar. 11, 2015, provisional application No. 62/180,169, filed on Jun. 16, 2015, provisional application No. 62/180,455, filed on Jun. 16, 2015, provisional application No. 62/206,031, filed on Aug. 17, 2015, provisional application No. 62/209,540, filed on Aug. 25, 2015.

(51) Int. Cl.

| | | |
|---|---|---|
| *C07C 45/51* | (2006.01) | |
| *B01J 37/03* | (2006.01) | |
| *B01J 37/00* | (2006.01) | |
| *B01J 23/02* | (2006.01) | |
| *B01J 23/06* | (2006.01) | |
| *B01J 23/18* | (2006.01) | |
| *C07C 2/06* | (2006.01) | |
| *C07C 2/52* | (2006.01) | |
| *C07C 45/00* | (2006.01) | |
| *C07C 51/16* | (2006.01) | |
| *C07C 67/03* | (2006.01) | |
| *C08F 236/08* | (2006.01) | |
| *C10L 1/04* | (2006.01) | |
| *B01J 37/08* | (2006.01) | |
| *B01J 23/10* | (2006.01) | |

(52) U.S. Cl.
CPC .......... *B01J 37/0018* (2013.01); *B01J 37/03* (2013.01); *B01J 37/082* (2013.01); *C07C 1/20* (2013.01); *C07C 2/06* (2013.01); *C07C 2/52* (2013.01); *C07C 45/00* (2013.01); *C07C 45/512* (2013.01); *C07C 51/16* (2013.01); *C07C 67/03* (2013.01); *C08F 236/08* (2013.01); *C10L 1/04* (2013.01); *C07C 2521/02* (2013.01); *C07C 2521/04* (2013.01); *C07C 2521/06* (2013.01); *C07C 2523/06* (2013.01); *C07C 2523/34* (2013.01); *C10L 2200/04* (2013.01); *C10L 2270/04* (2013.01); *Y02P 20/132* (2015.11); *Y02P 20/52* (2015.11)

(58) Field of Classification Search
USPC ....................................................... 585/640
See application file for complete search history.

(56) References Cited

U.S. PATENT DOCUMENTS

| | | |
|---|---|---|
| 2,984,644 A | 5/1961 | Wheat |
| 3,073,874 A | 1/1963 | Valet et al. |
| 3,258,455 A | 6/1966 | Natta et al. |
| 3,364,190 A | 1/1968 | Emrick |
| 3,568,457 A | 3/1971 | Briggs et al. |
| 3,794,690 A | 2/1974 | Steggerda |
| 3,803,249 A | 4/1974 | Rieve |
| 3,998,755 A | 12/1976 | Hayes |
| 4,163,697 A | 8/1979 | Michaux |
| 5,015,756 A | 5/1991 | Ramachandran et al. |
| 5,210,329 A | 5/1993 | Gomes De et al. |
| 5,393,918 A | 2/1995 | Dobson |
| 5,434,316 A | 7/1995 | Kissinger |
| 5,443,973 A | 8/1995 | Soshiwata et al. |
| 5,567,853 A | 10/1996 | Gupta |
| 5,786,522 A | 7/1998 | Cipullo |
| 7,067,597 B2 | 6/2006 | Van Egmond et al. |
| 8,193,402 B2 | 6/2012 | Gruber et al. |
| 8,373,012 B2 | 2/2013 | Peters et al. |
| 8,378,160 B2 | 2/2013 | Gruber et al. |
| 8,450,543 B2 | 5/2013 | Peters et al. |
| 8,487,149 B2 | 7/2013 | Gruber et al. |
| 8,546,627 B2 | 10/2013 | Gruber et al. |
| 2003/0109749 A1 | 6/2003 | Bogan et al. |
| 2004/0192994 A1 | 9/2004 | Bridges et al. |
| 2010/0150805 A1 | 6/2010 | Serban et al. |
| 2010/0216958 A1 | 8/2010 | Peters et al. |
| 2011/0087000 A1 | 4/2011 | Peters et al. |
| 2012/0171741 A1 | 7/2012 | Peters et al. |
| 2013/0261347 A1 | 10/2013 | Scates et al. |
| 2014/0234929 A1 | 8/2014 | Barr et al. |
| 2015/0217273 A1* | 8/2015 | Sun .......................... B01J 37/08 585/640 |

FOREIGN PATENT DOCUMENTS

| | | |
|---|---|---|
| EP | 1186592 A1 | 3/2002 |
| WO | WO 1997/012654 A1 | 4/1997 |
| WO | WO 2003/053570 A1 | 7/2003 |
| WO | WO 2008/024109 A1 | 2/2008 |
| WO | WO 2010/064652 A1 | 6/2010 |
| WO | WO 2011/136983 A1 | 11/2011 |
| WO | WO 2014/070354 A1 | 5/2014 |
| WO | WO 2016/061262 A1 | 4/2016 |

OTHER PUBLICATIONS

Dhaliwal, et al., "Measurement of the Unsaturation of Butyl Rubbers by the Iodine Index Method," Chemistry and Technology (1994); 67(4): 567-581.

Hutchings, et al., "The Conversion of Methanol and Other O-Compounds to Hydrocarbons over Zeolite β." Journal of Catalysis (1994); 147(1): 177-185.

Jacobsen, et al., "Mesoporous Zeolite Single Crystals." J. Am. Chem. Soc., (2000); 122 (29): 7116-7117.

Liu et al., "A study of ZnxZryOz mixed oxides for direct conversion of ethanol to isobutene." Applied Catalysis A: General (2013); 467: 91-97.

Mizuno, et al., "One-path and Selective Conversion of Ethanol to Propene on Scandium-modified Indium Oxide Catalysts." Chemical Letters (2012); 41: 892-894.

Murthy et al., "Conversion of ethanol to acetone over promoted iron oxide catalysis." J. Catalysis (1988); 109: 298-302.

Nakajima et al., "Efficient synthesis of acetone from ethanol over ZnO—CaO catalyst." J. Chem Soc. Chem Comm. (1987); 6: 394-395.

PCT/US2015/055581, International Search Report and Written Opinion dated Feb. 3, 2016, 19 pages.

PCT/US2015/055581, International Preliminary Report on Patentability dated Apr. 18, 2017, 16 pages.

Sun, et al., "Direct conversion of bio-ethanol to isobutene on nanosized Zn(x)Zr(y)O(z) mixed oxides with balanced acid-base sites." J Am Chem Soc. (2011); 133(29): 11096-11099.

Tago, et al., "Selective production of isobutylene from acetone over alkali metal ion-exchanged BEA zeolites." Catalysis Today (2011); 164: 158-162.

* cited by examiner

METHODS FOR CONVERSION OF ETHANOL TO FUNCTIONALIZED LOWER HYDROCARBONS AND DOWNSTREAM HYDROCARBONS

CROSS-REFERENCE TO RELATED APPLICATIONS

This application is a National Stage Entry of International Application No.: PCT/US2015/055581, filed on Oct. 14, 2015, which claims the benefit of priority to U.S. Provisional Application No. 62/209,540, filed on Aug. 25, 2015, U.S. Provisional Application No. 62/206,031, filed on Aug. 17, 2015, U.S. Provisional Application No. 62/180,455, filed on Jun. 16, 2015, U.S. Provisional Application No. 62/180,169, filed on Jun. 16, 2015, U.S. Provisional Application No. 62/131,652, filed on Mar. 11, 2015, U.S. Provisional Application No. 62/114,943, filed on Feb. 11, 2015, U.S. Provisional Application No. 62/114,945, filed on Feb. 11, 2015, U.S. Provisional Application No. 62/081,817, filed on Nov. 19, 2014, and U.S. Provisional Application No. 62/063,829, filed on Oct. 14, 2014, the contents of each of which are hereby incorporated by reference in their entireties.

TECHNICAL FIELD

The present application relates generally to methods for the conversion of ethanol to functionalized lower hydrocarbons and downstream hydrocarbons. More specifically, the present application relates to an improved process for the direct conversion of ethanol to isobutylene, propylene, and/or acetone, with improved carbon selectivity, product purity, and/or yield via utilization of novel $Zn_xZr_yA_vQ_sMn_wO_z$ mixed oxide catalysts or novel bifunctional heterogeneous catalysts.

BACKGROUND

Functionalized lower hydrocarbons, such as isobutylene, propylene, and acetone, are of significant interest for industrial and chemical applications.

Isobutylene, also known as isobutene or 2-methylpropene, is a hydrocarbon of significant interest that is widely used as an intermediate in the production of industrially important products, including para-xylene, jet fuel blendstocks, gasoline oxygenates, isooctane, methacrolein, methyl methacrylate, and butyl rubber. Methods for the conversion of isobutylene into these products are described in U.S. Pat. Nos. 8,193,402, 8,373,012, 8,378,160, 8,450,543, 8,487,149, and 8,546,627, as well as U.S. Patent Application Publication Nos. 2010/0216958, 2011/0087000, and 2012/0171741, each of which is herein incorporated by reference in its entirety for all purposes.

Historically, isobutylene has been obtained through the catalytic or steam cracking of fossil fuel feedstocks. With the depletion of fossil fuel resources, alternative routes for synthesizing isobutylene have been evaluated. In recent years, isobutylene has been generated from the dehydration of the bio-based commodity chemical, isobutanol. See U.S. Pat. Nos. 8,193,402, 8,373,012, 8,378,160, 8,450,543, 8,487,149, and 8,546,627, each of which is herein incorporated by reference in its entirety for all purposes.

Propylene, also known as methylethylene or propene, is a hydrocarbon of significant interest that is widely used as an intermediate in the production of plastic polypropylene which is used throughout industry in the manufacture of films, packaging, caps, and closures. Methods for the conversion of propylene into these products are described in U.S. Pat. Nos. 3,364,190, 7,067,597, 3,258,455, each of which is herein incorporated by reference in its entirety for all purposes.

Historically, propylene has been obtained through the catalytic or steam cracking of fossil fuel feedstocks. With the depletion of fossil fuel resources, alternative routes for synthesizing propylene have been evaluated. In recent years, propylene has been generated from olefin metathesis, also known as disproportionation, in which reversible reactions between ethylene and linear butenes results in the breaking of double bonds followed by reforming to propylene. In addition, propane dehydrogenation converts propane into propylene and byproduct hydrogen. See Patent references US2004/0192994 and WO 2011/136983, each of which is herein incorporated by reference in its entirety for all purposes.

Acetone is a functionalized hydrocarbon of significant interest that is widely used as an intermediate in the production of industrially important products, for example, methyl methacrylate and bisphenol A, as well as a solvent for cleaning purposes. Methods for the conversion of acetone into these and other products are described in U.S. Pat. Nos. EP0407811A2, US5393918, US5443973, EP1186592A1, EP0598243A2, US5434316A, US5210329, US5786522A each of which is herein incorporated by reference in its entirety for all purposes.

Historically, acetone has been obtained directly or indirectly from propylene. Approximately 83% of acetone is produced via the so-called cumene process. As a result, acetone production is tied to phenol production. In the cumene process, benzene is alkylated with propylene to produce cumene, which is oxidized by air to produce phenol and acetone. Other processes involve the direct oxidation of propylene (Wacker-Hoechst process), or the hydration of propylene to give 2-propanol which is oxidized to acetone. Acetone has been previously produced, and continues to be produced, in small quantities using the acetone-butanol-ethanol (ABE process) fermentation process with *Clostridium acetobutylicum* bacteria.

Bioethanol is also a significant commodity chemical product. With the increased availability and reduced cost of bioethanol, researchers have explored bioethanol as a feedstock for making a variety of downstream hydrocarbons, including the aforementioned hydrocarbon building blocks, isobutylene, propylene, and acetone. Until very recently, a process for the direct conversion of ethanol to isobutylene or propylene had not been described.

In 2011, however, Sun et al. disclosed a method utilizing a nanosized $Zn_xZr_yO_z$ mixed oxide catalyst prepared by a carbon template method for the selective conversion of ethanol to isobutylene with a carbon selectivity of 55% (83% of the maximum theoretical yield) from ethanol. In that reference, low levels of propylene have been detected, but not in industrially relevant yields. See Sun et al., 2011, *J. Am. Chem. Soc.* 133: 11096-11099, which is herein incorporated by reference in its entirety for all purposes. Utilizing a catalyst containing a 1:10 ratio of zinc to zirconium, Sun and colleagues were able to achieve isobutylene yields as high as 83% from ethanol fed at a relatively low molar concentration (0.6%) with less than 5% yield to propylene. Later results published by the same group demonstrated that increasing the molar concentration of ethanol in the feed stream beyond 0.6% dramatically reduces selectivity to isobutylene. Indeed, Liu et al. show that when the ethanol molar concentration in the feed stream increased from 0.6% to 11.9% for a given residence time, the isobutylene yield dropped from 85.4% to 8.2%, which suggests that further increasing the ethanol molar concentration beyond 11.9% would be expected to further reduce the isobutylene yield as well as propylene yield. Liu et al also demonstrated that increasing residence time enabled an increase in the ethanol molar concentration in the feed stream to a maximum 8.3 mol % while still resulting in isobutylene yields of 70-80% of theoretical. See Liu et al., 2013, *Applied Catalysis A* 467: 91-97, which is herein incorporated by reference in its entirety for all purposes. Accordingly, a process to convert ethanol at high molar concentrations is necessary for the conversion process.

In 2012, Mizuno et al. described the use of indium-oxide ($In_2O_3$) catalysts to produce propylene and isobutylene with a sum carbon selectivity of 58.1% (34.1% to propylene and 24% to isobutylene) from ethanol in the absence of exogenously added hydrogen. See Mizuno et al., 2012, *Chemical Letters* 41: 892-894, which is herein incorporated by reference in its entirety for all purposes. While the teachings of Sun et al. and Mizuno et al. make the direct conversion of bioethanol to isobutylene and/or propylene possible, enhancing the selectivity to these functionalized lower hydrocarbons beyond levels previously achieved (~55-58% carbon selectivity) can help reduce production costs for bioethanol-derived hydrocarbons. In addition, the methods of Sun et al. and Mizuno et al. are less than optimal because they either utilize a carbon template method for catalyst preparation (Sun) or rely on an expensive element, indium, which is not readily available on a large scale (Mizuno). Accordingly, a more industrially relevant catalyst is necessary for the conversion process.

Previous methods for conversion of ethanol to acetone are disclosed by Murthy et al, 1988, *J. Catalysis*, 109: 298-302, incorporated herein by reference in its entirety for all purposes, in which a calcium oxide, zinc oxide, or manganese promoted iron oxide catalyst was used. Murthy and colleagues were able to achieve acetone yields as high as 83% of theoretical from ethanol feed at relatively low molar concentrations of ethanol (10 mol % ethanol or 22 wt % ethanol in water). Increasing the ethanol molar ratio to 33% (56 wt % ethanol in water) resulted in only trace amounts of acetone formation. Additionally, the conversion of ethanol to acetone is disclosed by Nakajima et al, 1987, *J. Chem Soc, Chem Comm.*, 6: 394-395, incorporated herein by reference in its entirety for all purposes, in which mixed metal oxides (ZnO, ZnO/CaO, $ZnO/Na_2O$, ZnO/MgO, etc) were used. Nakajima and colleagues were able to achieve acetone yields as high as 91% of theoretical from ethanol fed at low molar concentrations of ethanol (reactor feed comprised of saturated nitrogen generated via bubbling nitrogen through a water/ethanol mixture). Accordingly, both a more industrially relevant catalyst and a process to convert high molar concentrations of ethanol are needed.

SUMMARY OF DISCLOSURE

The present application stems from the inventors' surprising discovery that high selectivity to functionalized lower hydrocarbons can be achieved despite high concentrations of ethanol in the feed stream. In addition, the inventors have also found that the use of high ethanol concentrations in the feed stream results in a product profile with favorable economics relative to the product profiles obtained with prior methods.

As described herein, the present inventors have developed methods which allow for the highly selective production of functionalized lower hydrocarbons from increased concentrations of ethanol in the feed stream. As further described herein, the present inventors have discovered new catalysts and (in some embodiments) new catalyst preparation methods to employ with increased concentrations of ethanol in the feed to afford processes for the highly selective production, and in some embodiments high yield and/or purity, of functionalized lower hydrocarbons from higher concentrations of ethanol in the feed stream. By virtue of the process described herein, the conversion of ethanol to functionalized lower hydrocarbons and subsequent downstream hydrocarbon products becomes more cost-competitive with petroleum-derived products.

In various aspects, the present application stems from the inventors' unexpected finding that the highly selective conversion of ethanol to functionalized lower hydrocarbons can be achieved at molar concentrations of ethanol in the feed stream exceeding 14%. Indeed, the Applicants' have observed functionalized lower hydrocarbon yields of nearly 70% of the maximum theoretical, e.g., utilizing a $Zn_xZr_yA_vQ_sMn_wO_z$ mixed oxide catalyst prepared via a hard-template method, a co-precipitation method, or a impregnated method, at ethanol feed concentrations exceeding those tested by Liu et al. This discovery provides important benefits commercially, as increasing the concentration of ethanol in the feed stream while maintaining high selectivity to a particular functionalized lower hydrocarbon can significantly reduce capital and energy costs.

Thus, in a first aspect, the application relates to a process for preparing isobutylene, comprising: (a) feeding to a reactor a reactor feed comprising ethanol at a molar concentration of at least about 14%; and (b) contacting the ethanol with a $Zn_xZr_yO_z$ mixed oxide catalyst in the reactor, whereby ethanol is converted to isobutylene at a yield of at least about 30%. In certain embodiments, the process may further comprise step (c) of recovering the isobutylene.

The highly selective production of isobutylene from increased concentrations of ethanol in the feed stream is described in Examples 1B-1E. Notably, isobutylene yields of nearly 70% are obtained from the direct conversion of ethanol at molar concentrations in the feed stream exceeding 14%. And, as shown in Examples 1B-1D, 1G, and 1I, the process of the present application also generates more of the higher-value co-products as compared to previously described processes. Specifically, valuable co-products such as propylene, phenol, meta-cresol and 3,5-xylenol are generated in higher quantities than seen with previously described ethanol to isobutylene conversion methods. Accordingly, the method described herein enables a process that generates isobutylene from high concentrations of ethanol and concomitantly results in the production of higher-value co-products.

Various aspects of the present application stems from the inventors' unexpected finding that the highly selective conversion of ethanol to high purity isobutylene can be achieved at molar concentrations of ethanol in the feed stream equal to or exceeding 14% at steam to carbon (S/C) ratios of 0.05 to 3.0 utilizing a $Zn_xZr_yO_z$ mixed oxide catalyst prepared by a co-precipitation method for the selective conversion of ethanol to isobutylene. Indeed, the inventors' have observed isobutylene yields of nearly 70% of the maximum theoretical at ethanol feed concentrations exceeding those tested by Liu et al, and with isobutylene purities meeting or exceeding the requirements necessary for high purity isobutylene (>99.75%). In addition, levels of co-products (e.g., propylene, phenols, methane, etc.) relative to isobutylene are reduced relative to $Zn_xZr_yO_z$ mixed oxide catalysts prepared via the hard template, impregnation, or inverse co-precipitation techniques.

Thus, in a second aspect, the application relates to a process for preparing isobutylene, comprising: (a) feeding to a reactor a reactor feed comprising ethanol at a molar concentration of at least about 14%; and (b) contacting the ethanol with a co-$Zn_xZr_yO_z$ mixed oxide catalyst prepared via co-precipitation technique in the reactor, whereby ethanol is converted to isobutylene at a yield of at least about 30%. In certain embodiments, the process may further comprise step (c) of recovering the isobutylene.

The highly selective production of high purity isobutylene from increased concentrations of ethanol in the feed stream is described in Examples 2B-C. Notably, isobutylene yields of nearly 80% are obtained from the direct conversion of ethanol at molar concentrations in the feed stream equal to or exceeding 14%. And, as shown in Examples 2B-C, the process of the present application generates a high purity isobutylene with improved selectivity to isobutylene relative to other potential co-products. Accordingly, the method described herein enables a process that generates high purity isobutylene from high concentrations of ethanol.

In various aspects, the present application stems from the inventors' unexpected finding that the highly selective conversion of ethanol to high purity propylene can be achieved at molar concentrations of ethanol in the feed stream equal to or exceeding 14% at steam to carbon (S/C) ratios of 0.05 to 3.0 utilizing a $Zn_xZr_yO_z$ mixed oxide catalyst prepared by a novel co-precipitation method in the presence of carbon black. Indeed, the inventors' have observed propylene yields in some cases as high as 90% of the maximum theoretical at ethanol feed concentrations exceeding those tested by Liu et al, and with propylene purities meeting or exceeding the requirements necessary for polymer grade propylene (minimum 99.50% with <0.5% propane). In addition, levels of co-products (e.g., isobutylene, phenols, methane, etc.) relative to propylene are reduced relative to $Zn_xZr_yO_z$ mixed oxide catalysts prepared via the hard template, impregnation, or inverse co-precipitation techniques.

Thus, in a third aspect, the application relates to a process for preparing propylene, comprising: (a) feeding to a reactor a reactor feed comprising ethanol at a molar concentration of at least about 14%; and (b) contacting the ethanol with a $Zn_xZr_yO_z$ mixed oxide catalyst prepared via co-precipitation technique in the reactor, whereby ethanol is converted to propylene at a yield of at least about 30%. In some embodiments, $Zn_xZr_yO_z$ mixed oxide catalyst used in step (b) is prepared via co-precipitation method in the presence of carbon black. In certain embodiments, the process may further comprise step (c) of recovering the propylene.

The highly selective production of high purity propylene from increased concentrations of ethanol in the feed stream is described in Examples 3A-B. Notably, propylene yields of nearly 85% are obtained from the direct conversion of ethanol at molar concentrations in the feed stream equal to or exceeding 14%. And, as shown in Example 3B, the process of the present application generates a high purity propylene with improved selectivity to propylene relative to other potential co-products. Accordingly, the method described herein enables a process that generates high purity propylene from high concentrations of ethanol.

In various aspects, the present application stems from the inventors' surprising discovery that high selectivity and yield to isobutylene can be achieved despite high concentrations of ethanol at lower steam to carbon ratios than previously reported in the feed stream with a $Zn_xZr_yMn_wO_z$ mixed oxide catalyst prepared via impregnation method for the selective conversion of ethanol to isobutylene.

In a fourth aspect, the disclosure relates to a process for preparing isobutylene, comprising: (a) feeding to a reactor a reactor feed comprising ethanol at a molar concentration of at least about 14%; and (b) contacting the ethanol with a $Zn_xZr_yMn_wO_z$ mixed oxide catalyst prepared via impregnation technique in the reactor, whereby ethanol is converted to isobutylene at a yield of at least about 30%. In certain embodiments, the process may further comprise step (c) of recovering the isobutylene.

The highly selective production of isobutylene from increased concentrations of ethanol in the feed stream is described in Examples 4B-C. Notably, isobutylene yields of nearly 80% are obtained from the direct conversion of ethanol at molar concentrations in the feed stream equal to or exceeding 14%. And, as shown in Examples 4B-C, the process of the present application generates high yields to isobutylene with improved selectivity to isobutylene relative to other potential co-products. Accordingly, the method described herein enables a process that generates high yields to isobutylene from high concentrations of ethanol.

Other aspects of the present application stems from the inventors' unexpected finding that the highly selective conversion of ethanol to high purity propylene can be achieved at molar concentrations of ethanol in the feed stream equal to or exceeding 14% at steam to carbon (S/C) ratios of 0.05 to 3.0 utilizing a $Zn_xZr_yA_vQ_sMn_wO_z$ (A is Si, Q is Al, and W is 0; A is Si, S is 0, and W is 0; A is Al, S is 0, and W is 0) mixed oxide catalyst prepared by a novel co-precipitation method in the presence of carbon black. The introduction of the silicon dioxide component or aluminum dioxide component results in a more stable catalyst, as measured by increased on-stream time before propylene selectivity begins to decrease thus requiring catalyst regeneration less frequently, and additionally allows for higher reaction temperatures while maintaining excellent propylene selectivity. Indeed, the inventors' have observed propylene yields in some cases approaching 90% of the maximum theoretical at ethanol feed concentrations exceeding those tested by Liu et al., and with propylene purities meeting or exceeding the requirements necessary for polymer grade propylene (minimum 99.50% with <0.5% propane). In addition, levels of co-products (e.g., isobutylene, phenols, ethylene, methane, etc.) relative to propylene are reduced relative to $Zn_xZr_yO_z$ mixed oxide catalysts prepared via the hard template, impregnation, or inverse co-precipitation techniques.

Thus, in a fifth aspect, the application relates to a process for preparing propylene, comprising: (a) feeding to a reactor a reactor feed comprising ethanol at a molar concentration of at least about 14%; and (b) contacting the ethanol with a $Zn_xZr_ySi_vO_z$, $Zn_xZr_yAl_vO_z$, or $Zn_xZr_yAl_vSi_sO_z$ mixed oxide catalyst prepared via co-precipitation technique in the reactor, whereby ethanol is converted to propylene at a yield of at least about 30%. In some embodiments, $Zn_xZr_ySi_vO_z$, $Zn_xZr_yAl_vO_z$, or $Zn_xZr_yAl_vSi_sO_z$ mixed oxide catalyst used in step (b) is prepared via co-precipitation method in the presence of carbon black. In certain embodiments, the process may further comprise step (c) of recovering the propylene.

The highly selective production of high purity propylene from increased concentrations of ethanol in the feed stream with novel co-precipitated $Zn_xZr_ySi_vO_z$ is described in Example 5A-B. Notably, propylene yields of nearly 85% are obtained from the direct conversion of ethanol at molar concentrations in the feed stream equal to or exceeding 14%. And, as shown in Examples 5A-B, the process of the present application generates high purity propylene with improved selectivity to propylene relative to other potential co-products. Accordingly, the method described herein enables a process that generates high purity propylene from high concentrations of ethanol.

The highly selective production of high purity propylene from increased concentrations of ethanol in the feed stream with novel co-precipitated $Zn_xZr_yAl_wO_z$ is described in Examples 6A-B. Notably, propylene yields of nearly 85% are obtained from the direct conversion of ethanol at molar concentrations in the feed stream equal to or exceeding 14%. And, as shown in Examples 6A-B, the process of the present application generates high purity propylene with improved selectivity to propylene relative to other potential co-products, and allows for on-stream times that significantly exceed previously reported mixed metal oxides catalyst on-stream times before in-situ catalyst regeneration is required. Accordingly, the method described herein enables a process that generates high purity propylene from high concentrations of ethanol.

The highly selective production of high purity propylene from increased concentrations of ethanol in the feed stream with novel co-precipitated $Zn_xZr_yAl_wSi_sO_z$ is described in Examples 7A-B. Notably, propylene yields of nearly 75.5% are obtained from the direct conversion of ethanol at molar concentrations in the feed stream equal to or exceeding 37%. And, as shown in Examples 7A-B, the process of the present application generates propylene with improved selectivity to propylene relative to other potential co-products, and allows for on-stream times that significantly exceed previously reported mixed metal oxides catalyst on-stream times before in-situ catalyst regeneration is required. Accordingly, the method described herein enables a process that generates high purity propylene from high concentrations of ethanol.

Various aspects of the present application stems from the inventors' surprising discovery that high selectivity to acetone can be achieved despite high concentrations of ethanol with a $Zn_xMg_yZr_yO_z$ or $Zn_xCu_yZr_yO_z$ mixed oxide catalyst prepared by a co-precipitation method, or a quaternary mixed metal oxide catalyst comprised of a $Zn_xMg_yMn_wZr_yO_z$ or $Zn_xCu_yMn_wZr_yO_z$ prepared by an impregnation method, for the selective conversion of ethanol to acetone.

Thus, further aspects of the present application stems from the inventors' unexpected finding that the highly selective conversion of ethanol to acetone can be achieved at molar concentrations of ethanol in the feed stream equal to or exceeding 14% (29 wt % ethanol) at steam to carbon (S/C) ratios of 0.05 to 3.0 utilizing a $Zn_xMg_yZr_yO_z$ or $Zn_xCu_yZr_yO_z$ mixed oxide catalyst prepared by a co-precipitation method, or utilizing a $Zn_xMg_yMn_wZr_yO_z$ or $Zn_xCu_yMn_wZr_yO_z$ mixed oxide catalyst prepared by an impregnation method, for the selective conversion of ethanol to acetone. Indeed, the inventors' have observed acetone yields of nearly 90% of the maximum theoretical at ethanol feed concentrations exceeding those tested by Murthy and Nakajima et al. In addition, co-products levels (e.g., propylene, isobutylene, ethylene, phenols, methane, etc.) relative to acetone are reduced relative to previously used mixed oxide catalysts.

Thus, in a six aspect, the application relates to a process for preparing acetone, comprising: (a) feeding to a reactor a reactor feed comprising ethanol at a molar concentration of at least about 14%; and (b) contacting the ethanol with a $Zn_xMg_yZr_yO_z$ or $Zn_xCu_yZr_yO_z$ mixed oxide catalyst prepared via co-precipitation technique or $Zn_xMg_yMn_wZr_yO_z$ or $Zn_xCu_yMn_wZr_yO_z$ mixed oxide catalyst prepared by an impregnation method in the reactor, whereby ethanol is converted to acetone in yield of at least about 60%. In certain embodiments, the process may further comprise step (c) of recovering the acetone.

The highly selective production of acetone from increased concentrations of ethanol via a co-precipitated $Zn_xMg_yZr_yO_z$ or $Zn_xCu_yZr_yO_z$ mixed oxide catalyst is described in Example 8C-D. Notably, acetone yields of nearly 90% are obtained from the direct conversion of ethanol at molar concentrations in the feed stream equal to or exceeding 14%. Accordingly, the method described herein enables a process that generates acetone in high yield from high concentrations of ethanol.

The highly selective production of acetone from increased concentrations of ethanol in the feed stream via an impregnated $Zn_xMg_yMn_wZr_yO_z$ or $Zn_xCu_yMn_wZr_yO_z$ mixed oxide catalyst is described in Example 9C-D. Notably, acetone yields of nearly 90% are obtained from the direct conversion of ethanol at molar concentrations in the feed stream equal to or exceeding 14%. Accordingly, the method described herein enables a process that generates acetone in high yield from high concentrations of ethanol.

To our knowledge, this is the first report of a ternary mixed metal oxide catalyst comprised of $Zn_xMg_yZr_yO_z$ or $Zn_xCu_yZr_yO_z$, and a quaternary mixed metal oxide catalyst comprised of a $Zn_xMg_yMn_wZr_yO_z$ or $Zn_xCu_yMn_wZr_yO_z$, resulting in high yields of acetone from ethanol utilizing a water/ethanol feed at ethanol concentrations at or above 50 wt %.

In various other aspects, the present application stems from the identification of catalysts and associated processes enabling higher carbon selectivities to functionalized lower hydrocarbon (e.g., isobutylene and/or propylene) than previously disclosed methods. Accordingly, the catalysts and processes described herein support an industrially relevant process with improved yields of functionalized lower hydrocarbons (e.g., isobutylene and/or propylene) from ethanol which lowers the cost of goods in order to directly compete with petro-based products.

As described herein, the present application provides a highly selective process which allows for the direct conversion of ethanol to isobutylene and/or propylene at a total functionalized lower hydrocarbons olefin carbon selectivity (i.e., isobutylene+propylene) exceeding 60%. By virtue of the catalysts and processes described herein, the conversion of ethanol to isobutylene and/or propylene, as well as subsequent downstream hydrocarbon products becomes more cost-competitive with petroleum-derived products.

Thus, in a seventh aspect, the application relates to a process for preparing at least one functionalized lower olefin, comprising: (a) feeding to a reactor a reactor feed comprising ethanol; and (b) contacting the ethanol in the reactor with a bifunctional heterogeneous catalyst comprising acid and base functionality, whereby ethanol is converted to at least one functionalized lower olefin, wherein the bifunctional heterogeneous catalyst comprises a basic component selected from one or more of the following: (i) Ca, Fe, Zn, Ce, Sn, K, Ba, U, Hf, Mn, Sb, Al, Nb, Sc, In, V, Cr, Mo, Ni, Co, Cu, Na, Cs, Rb, B, Mg, Sr, Cd, La, Y, hydrotalcite, zincaluminate, phosphate, and combinations thereof; (ii) oxides from the group of Ti, V, Nb, Ta, Mo, Cr, W, Mn, Re, Al, Ga, Fe, Co, Ir, Ni, Si, Cu, Sn, Cd, P, Pd, Pt, and combinations thereof; and (iii) combinations of (i) and (ii), and wherein the bifunctional heterogeneous catalyst comprises an acid component selected from at least one of Zr, Ti, Si, Ce, Co, Sn, Al, and oxides thereof, zeolites, and amorphous silica alumina. In certain embodiments, the process may further comprise step (c) of recovering the functionalized lower hydrocarbon. In exemplary embodiments, the functionalized lower hydrocarbon is selected from propylene and isobutylene.

Inventive bifunctional heterogeneous catalysts for the conversion of ethanol to at least one functionalized lower hydrocarbon are described in Examples 10A-C.

In yet another aspect, the present disclosure provides methods for converting isobutylene produced by the methods of the present invention into high-value, beneficial hydrocarbons. In some embodiments, the beneficial hydrocarbons are selected from the group consisting of paraxylene, jet fuel blendstocks, gasoline oxygenates, isooctane, methacrolein, methyl methacrylate, and butyl rubber.

Accordingly, disclosed herein, in some embodiments, is a process for preparing a functionalized lower hydrocarbon, comprising: (a) feeding to a reactor a reactor feed comprising ethanol at a concentration of at least about 14 mol %; and (b) contacting the ethanol with a mixed oxide catalyst in the reactor, the mixed oxide catalyst having the formula $Zn_xZr_yA_vQ_sMn_wO_z$, whereby the ethanol is converted to at least one functionalized lower hydrocarbon at a yield of at least about 30% of the maximum theoretical molar yield, wherein X is 1 to 10, wherein Y is 1 to 100, wherein A is Al, Si, Mg, or Cu, and V is 0 to 100, wherein Q is Al, Si, Mg, or Cu, and S is 0 to 100, wherein W is 0 to 30, and wherein Z is 5 to 250. In some embodiments, the functionalized lower hydrocarbon is isobutylene. In some embodiments, the functionalized lower hydrocarbon is propylene. In some embodiments, the functionalized lower hydrocarbon is acetone.

In further embodiments, the process further comprises the step (c) of recovering at least one of the functionalized lower hydrocarbons. In some embodiments, the functionalized lower hydrocarbon recovered in step (c) is isobutylene. In other embodiments, the functionalized lower hydrocarbon recovered in step (c) is propylene. In still other embodiments, the functionalized lower hydrocarbon recovered in step (c) is acetone.

In some embodiments, the ethanol is bio-based ethanol. In one such embodiment, at least about 60 wt % of the bio-based ethanol is derived from a non-petroleum feedstock. In another embodiment, at least about 70 wt % of the bio-based ethanol is derived from a non-petroleum feedstock. In yet another embodiment, at least about 80 wt % of the bio-based ethanol is derived from a non-petroleum feedstock. In still another embodiment, at least about 90 wt % of the bio-based ethanol is derived from a non-petroleum feedstock. In yet another embodiment, at least about 95 wt % of the bio-based ethanol is derived from a non-petroleum feedstock. In such embodiments, the ethanol is produced in an ethanol bio-refinery via the fermentation of sugars by yeast.

In some embodiments, the ethanol is obtained from biomass-generated syngas. In other embodiments, the ethanol is obtained from syngas that has been derived from natural gas, coal, or a combination of natural gas and coal. In still other embodiments, the ethanol is obtained from a combination of biomass-generated syngas and syngas that has been derived from natural gas, coal, or a combination of natural gas and coal.

In some embodiments, the ethanol is petroleum-based ethanol. In further embodiments, the petroleum-based ethanol is synthesized from ethylene. In other embodiments, the ethanol is fuel-grade ethanol.

In some embodiments, the reactor feed is an azeotropic ethanol-water mixture obtained from an ethanol production plant. In other embodiments, the azeotropic ethanol-water mixture is obtained from an ethanol production plant prior to dehydration of the azeotropic ethanol-water mixture. In still other embodiments, the molar concentration of ethanol in the ethanol-water mixture is about 80%, 81%, 82%, 83%, 84%, 85%, 86%, 87%, 88%, 89%, 90%, 91%, 92%, 93%, 94%, or 95% ethanol.

In some embodiments, the reactor feed comprises at least about 15 mol % ethanol. In other embodiments, the reactor feed comprises at least about 20 mol % ethanol. In still other embodiments, the reactor feed comprises ethanol at a molar concentration of at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%.

In some embodiments, the reactor feed comprises ethanol and at least one constituent selected from water, methanol, one or more fusel alcohols, one or more diluents, and combinations thereof. In other embodiments, the reactor feed comprises ethanol and water. In some embodiments, the reactor feed comprises water at a molar concentration of less than about 85%. In still other embodiments, wherein the reactor feed comprises water at a molar concentration of less than about 75%. In yet other embodiments, wherein the reactor feed comprises water at a molar concentration of less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, or less than about 5%.

In one embodiment, the reactor feed consists of ethanol and water. In another embodiment, the reactor feed consists of ethanol, water, and methanol. In still another embodiment, the reactor feed consists essentially of ethanol, water, methanol, and one or more fusel alcohols.

In some embodiments, the fusel alcohol is selected from 1-propanol, isobutanol, 2-methyl-1-butanol, and isopentanol. In other embodiments, the reactor feed comprises at least one diluent. In such embodiments, the diluent is selected from carbon dioxide, nitrogen, methane, ethane, propane, and mixtures thereof.

In some embodiments, the reactor feed comprises nitrogen at a molar concentration of less than about 10%. In other embodiments, the reactor feed comprises nitrogen at a molar concentration of less than about 5%. In still other embodiments, the reactor feed comprises nitrogen at a molar concentration of less than about 2%, less than about 1%, less than about 0.5%, or less than about 0.1%. In yet another embodiments, the reactor feed is substantially free of nitrogen.

In some embodiments, the ethanol is contacted with the $Zn_xZr_yA_vQ_sMn_wO_z$ mixed oxide catalyst at a temperature falling within the range of about 300° C. to about 600° C. In an embodiment, the ethanol is contacted with the $Zn_xZr_yA_vQ_sMn_wO_z$ mixed oxide catalyst at a temperature of about 460° C. In another embodiment, the ethanol is contacted with the $Zn_xZr_yA_vQ_sMn_wO_z$ mixed oxide catalyst at a temperature of about 470° C. In still another embodiment, the ethanol is contacted with the $Zn_xZr_yA_vQ_sMn_wO_z$ mixed oxide catalyst at a temperature of about 485° C. In yet another embodiment, the ethanol is contacted with the $Zn_xZr_yA_vQ_sMn_wO_z$ mixed oxide catalyst at a temperature of about 490° C.

In some embodiments, the ethanol is contacted with the $Zn_xZr_yA_vQ_sMn_wO_z$ mixed oxide catalyst at a weight hourly space velocity range of about 0.1 $hr^{-1}$ to about 2.0 $hr^{-1}$. In other embodiments, the ethanol is contacted with the $Zn_xZr_yA_vQ_sMn_wO_z$ mixed oxide catalyst at a weight hourly space velocity of about 1.1 hr$^{-1}$. In still other embodiments, the ethanol is contacted with the $Zn_xZr_yA_vQ_sMn_wO_z$ mixed oxide catalyst at a weight hourly space velocity of about 0.6 hr$^{-1}$.

In some embodiments, the $Zn_xZr_yA_vQ_sMn_wO_z$ mixed oxide catalyst is prepared using a hard-template method, a co-precipitation method, or an impregnated method.

In some embodiments, V is 0, S is 0, and W is 0. In such embodiments, the ratio of Zn/Zr (x:y) in the $Zn_xZr_yO_z$ mixed oxide catalyst is about 1:1 to about 1:100. In another embodiment, the ratio of Zn/Zr (x:y) in the $Zn_xZr_yO_z$ mixed oxide catalyst is about 1:2 to about 1:50. In yet another embodiment, the ratio of Zn/Zr (x:y) in the $Zn_xZr_yO_z$ mixed oxide catalyst is about 1:5 to about 1:25. In still another embodiment, the ratio of Zn/Zr (x:y) in the $Zn_xZr_yO_z$ mixed oxide catalyst is from about 1:8 to about 1:20. In an exemplary embodiment, the ratio of Zn/Zr (x:y) in the $Zn_xZr_yO_z$ mixed oxide catalyst is about 1:12. In another exemplary embodiment, the ratio of Zn/Zr (x:y) in the $Zn_xZr_yO_z$ mixed oxide catalyst is about 1:25. In some embodiments, the ratio of Zn/Zr (x:y) in the $Zn_xZr_yO_z$ mixed oxide catalyst is about 1:20.

In an exemplary embodiment, when the ratio of the Zn/Zr (x:y) in the $Zn_xZr_yO_z$ mixed oxide catalyst is about 1:20, the $Zn_xZr_yO_z$ mixed oxide catalyst is prepared using a hard-template method. In one such exemplary embodiment, the functionalized lower hydrocarbon is isobutylene. In another embodiment, the yield of the isobutylene is at least about 45% of the maximum theoretical molar yield. In yet another embodiment, wherein the isobutylene is at least about 96% pure. In another exemplary embodiment, the molar concentration of the ethanol in the reactor feed about 14.8%. In one such embodiment, the functionalized lower hydrocarbon includes isobutylene, propylene, and acetone. In another embodiment, the isobutylene is produced at a yield of about 45% of the maximum theoretical molar yield, the propylene is produced at a yield of about 8% of the maximum theoretical molar yield, and the acetone is produced at a yield of about 14% of the maximum theoretical molar yield. In yet another exemplary embodiment, the molar concentration of the ethanol in the reactor feed about 25%. In one such embodiment, the functionalized lower hydrocarbon includes isobutylene, propylene, and acetone. In still another embodiment, the isobutylene is produced at a yield of about 46% of the maximum theoretical molar yield, the propylene is produced at a yield of about 14% of the maximum theoretical molar yield, and the acetone is produced at a yield of about 3% of the maximum theoretical molar yield. In some embodiments, a carbon support for the mixed oxide catalyst is utilized. In further embodiments, the carbon support is a carbon black support.

In some embodiments, when the ratio of Zn/Zr (x:y) in the $Zn_xZr_yO_z$ mixed oxide catalyst is about 1:25, the $Zn_xZr_yO_z$ mixed oxide catalyst is prepared using a co-precipitation method. In one such embodiment, the functionalized lower hydrocarbon is isobutylene. In another embodiment, the yield of the isobutylene is at least about 50% of the maximum theoretical molar yield. In still another embodiment, the isobutylene is at least about 99.7% pure. In an exemplary embodiment, the molar concentration of the ethanol in the reactor feed is about 25%. In such embodiments, the functionalized lower hydrocarbon produced by the process includes isobutylene, propylene, and acetone. In another embodiment, the isobutylene is produced at a yield of about 50% of the maximum theoretical molar yield, the propylene is produced at a yield of about 10% of the maximum theoretical molar yield, and the acetone is produced at yield of about 2% of the maximum theoretical value.

In some embodiments, when the ratio of Zn/Zr (x:y) in the $Zn_xZr_yO_z$ mixed oxide catalyst is about 1:20, the $Zn_xZr_yO_z$ mixed oxide catalyst is prepared using a co-precipitation method. In such embodiments, the functionalized lower hydrocarbon is propylene. In another embodiment, the yield of the propylene at least about 60% of the maximum theoretical molar yield. In yet another embodiment, the propylene is at least 99.5% pure. In an exemplary embodiment, the molar concentration of the ethanol in the reactor feed is at least about 25%. In such embodiments, the functionalized lower hydrocarbon includes isobutylene, propylene, and acetone. In another embodiment, the isobutylene is produced at a yield of about 5% of the maximum theoretical molar yield, the propylene is produced at a yield of about 63% of the maximum theoretical molar yield, and the acetone is produced at a yield of about 1% of the maximum theoretical molar yield.

In some embodiments, V is 0, S is 0, and wherein W is greater than or equal to about 1. In such an embodiment, the ratio of Zn/Zr/Mn (x:y:w) in the $Zn_xZr_yMn_wO_z$ mixed oxide catalyst is from about 1:1:1 to about 1:100:30. In another embodiment, the ratio of Zn/Zr/Mn (x:y:w) in the $Zn_xZr_yMn_wO_z$ mixed oxide catalyst is from about 1:2:30 to about 1:50:30. In still another embodiment, the ratio of Zn/Zr/Mn (x:y:w) in the $Zn_xZr_yMn_wO_z$ mixed oxide catalyst is from about 1:5:1 to about 1:25:30. In yet another embodiment, the ratio of Zn/Zr/Mn (x:y:w) in the $Zn_xZr_yMn_wO_z$ mixed oxide catalyst is from about 1:8:1 to about 1:20:30. In an exemplary embodiment, the ratio of Zn/Zr/Mn (x:y:w) in the $Zn_xZr_yMn_wO_z$ mixed oxide catalyst is from about 1:8:1. In such an embodiment, the $Zn_xZr_yMn_wO_z$ mixed oxide catalyst is prepared using an impregnation method. In another embodiment, the functionalized lower hydrocarbon is isobutylene. In still another embodiment, the yield of the isobutylene is at least about 50% of the maximum theoretical molar yield. In yet another embodiment, the isobutylene is at least 97% pure. In another exemplary embodiment, the molar concentration of the ethanol in the reactor feed is at least 25% or greater. In such embodiments, the functionalized lower hydrocarbon includes isobutylene, propylene, and acetone. In still other embodiments, the isobutylene is produced at a yield of about 50% of the maximum theoretical molar yield, the propylene is produced at a yield of about 10% of the maximum theoretical molar yield, and the acetone is produced at a yield of about 2% of the maximum theoretical molar yield.

In some embodiments, A is Si or Al and V is greater than or equal to about 1, W is 0, and S is 0.

In another embodiment, A is Si and V is greater than or equal to about 1, W is 0, and S is 0. In some embodiments, the ratio of Zn/Zr/Si (x:y:v) in the $Zn_xZr_ySi_vO_z$ mixed oxide catalyst is from about 1:1:1 to about 1:100:100. In other embodiments, the ratio of Zn/Zr/Si (x:y:v) in the $Zn_xZr_ySi_vO_z$ mixed oxide catalyst is from about 1:2:2 to about 1:50:50. In still other embodiments, the ratio of Zn/Zr/Si(x:y:v) in the $Zn_xZr_ySi_vO_z$ mixed oxide catalyst is from about 1:5:5 to about 1:25:25. In yet other embodiments, the ratio of Zn/Zr/Si (x:y:v) in the $Zn_xZr_ySi_vO_z$ mixed oxide catalyst is from about 1:8:8 to about 1:20:20. In an exemplary embodiment, the ratio of Zn/Zr/Si (x:y:v) in the $Zn_xZr_ySi_vO_z$ mixed oxide catalyst is about 1:12:12. In such an embodiment, the $Zn_xZr_ySi_vO_z$ mixed oxide catalyst is prepared using a co-precipitation method. In a further embodiment, the functionalized lower hydrocarbon is propylene. In another embodiment, the yield of the propylene is at least about 60%. In still another embodiment, the propylene is about 99.5% pure. In an exemplary embodiment, the molar concentration of the ethanol in the reactor feed is about 25%. In such an embodiment, the functionalized lower hydrocarbon includes isobutylene, propylene, and acetone. In another embodiment, the isobutylene is produced at a yield of about 8% of the maximum theoretical molar yield, the propylene is produced at a yield of about 60% of the maximum theoretical molar yield, and the acetone is produced at a yield of about 0.1% of the maximum theoretical molar yield.

In another embodiment, A is Al and V is greater than or equal to about 1, W is 0 and S is 0. In one embodiment, the ratio of Zn/Zr/Al (x:y:v) in the $Zn_xZr_yAl_vO_z$ mixed oxide catalyst is from about 1:1:1 to about 1:100:100. In another embodiment, the ratio of Zn/Zr/Al (x:y:v) in the $Zn_xZr_yAl_vO_z$ mixed oxide catalyst is from about 1:2:2 to about 1:50:50. In yet another embodiment, the ratio of Zn/Zr/Al (x:y:v) in the $Zn_xZr_yAl_vO_z$ mixed oxide catalyst is from about 1:5:5 to about 1:25:25. In still another embodiment, the ratio of Zn/Zr/Al (x:y:v) in the $Zn_xZr_yAl_vO_z$ mixed oxide catalyst is from about 1:8:8 to about 1:20:20. In an exemplary embodiment, the ratio of Zn/Zr/Al (x:y:v) in the $Zn_xZr_yAl_vO_z$ mixed oxide catalyst is about 1:12:1. In one such embodiment, the $Zn_xZr_yAl_vO_z$ mixed oxide catalyst is prepared using a co-precipitation method. In another embodiment, the functionalized lower hydrocarbon is propylene. In yet another embodiment, the yield of the propylene is at least about 59% of the maximum theoretical molar yield. In still another embodiment, the propylene has a purity of at least about 99.5%. In an exemplary embodiment, the molar concentration of the ethanol in the reactor feed is about 37%. In such embodiment, the functionalized lower hydrocarbon includes isobutylene, propylene, and acetone. In another embodiment, the isobutylene is produced at a yield of about 9% of the maximum theoretical molar yield, the propylene is produced at a yield of about 59% of the maximum theoretical molar yield, and the acetone is produced at a yield of about 0.7% of the maximum theoretical molar yield.

In some embodiments, A is Al, and V is greater than or equal to 1, Q is Si and S is greater than or equal to about 1, and W is 0. In such embodiments, the ratio of Zn/Zr/Al/Si (x:y:v:s) in the $Zn_xZr_yAl_vSi_sO_z$ mixed oxide catalyst is from about 1:1:1:1 to about 1:100:100:100. In other embodiments, the ratio of Zn/Zr/Al/Si (x:y:v:s) in the $Zn_xZr_yAl_v$-$Si_sO_z$ mixed oxide catalyst is from about 1:2:2:2 to about 1:50:50:50. In yet other embodiments, the ratio of Zn/Zr/Al/Si (x:y:v:s) in the $Zn_xZr_yAl_vSi_sO_z$ mixed oxide catalyst is from about 1:5:5:5 to about 1:25:25:25. In still other embodiments, the ratio of Zn/Zr/Al/Si (x:y:v:s) in the $Zn_x$-$Zr_yAl_vSi_sO_z$ mixed oxide catalyst is from about 1:8:8:8 to about 1:20:20:20. In an exemplary embodiment, the ratio of Zn/Zr/Al/Si (x:y:v:s) in the $Zn_xZr_yAl_vSi_sO_z$ mixed oxide catalyst is about 1:12:2:2. In one such embodiment, the $Zn_xZr_yAl_vSi_sO_z$ mixed oxide catalyst is prepared using a co-precipitation method. In another embodiment, the functionalized lower hydrocarbon is propylene. In yet another embodiment, the yield of the propylene is at least about 70% of the maximum theoretical molar yield. In another exemplary embodiment, the molar concentration of the ethanol in the reactor feed is about 37%. In such an embodiment, the functionalized lower hydrocarbon includes isobutylene, propylene, and acetone. In another embodiment, the isobutylene is produced at a yield of about 27% of the maximum theoretical molar yield, the propylene is produced at a yield of about 75.5% of the maximum theoretical molar yield, and the acetone is produced at a yield of about 0.01% of the maximum theoretical molar yield.

In some embodiments, A is Mg or Cu, V is greater than or equal to about 1, W is 0, and S is 0. In such embodiments, the ratio of Zn/Mg/Zr or Zn/Cu/Zr (x:v:y) in the $Zn_xMg_vZr_yO_z$ or $Zn_xCu_vZr_yO_z$ mixed oxide catalyst is from about 1:1:1 to about 1:10:100. In other embodiments, the ratio of Zn/Mg/Zr or Zn/Cu/Zr (x:v:y) in the $Zn_xMg_vZr_yO_z$ or $Zn_x$-$Cu_vZr_yO_z$ mixed oxide catalyst is from about 1:1:2 to about 1:5:50. In still other embodiments, the ratio of Zn/Mg/Zr or Zn/Cu/Zr (x:v:y) in the $Zn_xMg_vZr_yO_z$ or $Zn_xCu_vZr_yO_z$ mixed oxide catalyst is from about 1:1:5 to about 1:1:25. In yet another embodiment, the ratio of Zn/Mg/Zr or Zn/Cu/Zr (x:v:y) in the $Zn_xMg_vZr_yO_z$ or $Zn_xCu_vZr_yO_z$ mixed oxide catalyst is from about 1:1:8 to about 1:5:20. In an exemplary embodiment, the ratio of Zn/Mg/Zr or Zn/Cu/Zr (x:v:y) in the $Zn_xMg_vZr_yO_z$ or $Zn_xCu_vZr_yO_z$ mixed oxide catalyst is from about 1:1:25. In such an embodiment, the $Zn_xMg_vZ$-$r_yO_z$ or $Zn_xCu_vZr_yO_z$ mixed oxide catalyst is prepared using a co-precipitation method. In some embodiments, the functionalized lower hydrocarbon is acetone. In yet another embodiment, the yield of the acetone is at least about 54% of the maximum theoretical molar yield. In still other embodiments, the acetone has a purity of at least 96%. In another exemplary embodiment, the molar concentration of the ethanol in the reactor feed is at least about 25% or greater. In such embodiments, the functionalized lower hydrocarbon includes isobutylene, propylene, and acetone. In other embodiments, the isobutylene is produced at a yield of about 8% of the maximum theoretical molar yield, the propylene is produced at a yield of about 2% of the maximum theoretical molar yield, and the acetone is produced at a yield of about 54% of the maximum theoretical molar yield.

In some embodiments, A is Mg or Cu, V is greater than or equal to about 1, W is greater than or equal to about 1, and S is 0. In such embodiments, the ratio of Zn/Mg/Mn/Zr (x:v:w:y) or Zn/Cu/Mn/Zr (x:v:w:y) in the $Zn_xMg_vMn_wZ$-$r_yO_z$ or $Zn_xCu_vMn_wZr_yO_z$ mixed oxide catalyst is from about 1:1:1:10 to about 1:10:10:100. In other embodiments, the ratio of Zn/Mg/Mn/Zr (x:v:w:y) or Zn/Cu/Mn/Zr (x:v:w:y) in the $Zn_xMg_vMn_wZr_yO_z$ or $Zn_xCu_vMn_wZr_yO_z$ mixed oxide catalyst is from about 1:1:1:2 to about 1:5:5:50. In still other embodiments, the ratio of Zn/Mg/Mn/Zr (x:v:w:y) or Zn/Cu/Mn/Zr (x:v:w:y) in the $Zn_xMg_vMn_wZr_yO_z$ or $Zn_xCu_vMn_wZ$-$r_yO_z$ mixed oxide catalyst is from about 1:1:1:5 to about 1:5:5:25. In yet other embodiments, the ratio of Zn/Mg/Mn/Zr (x:v:w:y) or Zn/Cu/Mn/Zr (x:v:w:y) in the $Zn_xMg_vMn_w$-$Zr_yO_z$ or $Zn_xCu_vMn_wZr_yO_z$ mixed oxide catalyst is from about 1:1:1:8 to about 1:5:5:20. In an exemplary embodiment, the ratio of Zn/Mg/Mn/Zr (x:v:w:y) or Zn/Cu/Mn/Zr (x:v:w:y) in the $Zn_xMg_vMn_wZr_yO_z$ or $Zn_xCu_vMn_wZr_yO_z$ mixed oxide catalyst is from about 1:1:5:15. In such an embodiment, the $Zn_xMg_vMn_wZr_yO_z$ or $Zn_xCu_vMn_wZr_yO_z$ mixed oxide catalyst is prepared using an impregnation method. In some embodiments, the functionalized lower hydrocarbon is acetone. In another embodiment, the yield of the acetone is at least about 60% of the maximum theoretical molar yield. In yet another embodiment, the acetone is at least about 96% pure. In another exemplary embodiment, the molar concentration of the ethanol in the reactor feed is about 33%. In another embodiment, the functionalized lower hydrocarbon includes isobutylene, propylene, and acetone. In still another embodiment, the isobutylene is produced at a yield of about 10% of the maximum theoretical molar yield, the propylene is produced at a yield of about 1% of the maximum theoretical molar yield, and the acetone is produced at a yield of about 62%, of the maximum theoretical molar yield.

In some embodiments, at least one promoter is utilized. In further embodiments, the promoter is selected from tin, copper, rhenium, ruthenium, gold, silver, manganese, magnesium, scandium, nickel, and combinations thereof.

In some embodiments, the yield of the functionalized lower hydrocarbon is at least about 35% of the maximum theoretical molar yield. In other embodiments, the yield of the functionalized lower hydrocarbon is at least about 40% of the maximum theoretical molar yield. In still other embodiments, the yield of the functionalized lower hydrocarbon is at least about 45%, 50%, 55%, 60%, 65%, 70%, 75%, 80%, 85%, or 90% of the maximum theoretical molar yield.

In some embodiments, isobutylene is recovered using distillation. In other embodiments, isobutylene is recovered using acid extraction. In some embodiments, propylene is recovered using distillation. In other embodiments, the acetone is recovered using distillation.

In some embodiments, residual water generated as by-product during the conversion of ethanol to a functionalized hydrocarbon is isolated. In other embodiments, the isolated residual water is recycled back to the front end of the reactor.

In some embodiments, the $Zn_xZr_yA_vQ_sMn_wO_z$ mixed oxide catalyst is regenerated in situ. In other embodiments, the $Zn_xZr_yA_vQ_sMn_wO_z$ mixed oxide catalyst is regenerated in situ by switching the process feed to an oxygen-rich stream while maintaining catalyst reaction temperatures.

In some embodiments, the reactor is selected from a fixed-bed, adiabatic, fluid-bed, transport bed, and moving bed reactor. In other embodiments, wherein the reactor is a fixed-bed reactor. In still other embodiments, the reactor bed length-to-diameter ratio is at least about 5. In some embodiments, the reactor bed length-to-diameter ratio is at least about 10. In yet another embodiment, the reactor bed length-to-diameter ratio is at least about 100. In still yet another embodiment, the reactor bed length-to-diameter ratio is at least about 1000.

In some embodiments, at least one co-product selected propylene, isobutylene, acetone, hydrogen, carbon dioxide, methane, phenol, 2-pentanone, mesityl oxide, methyl isobutylketone, 3-methyl-2-butanone, 2-methyl phenol, 3-methyl phenol (meta-cresol), 2,5-dimethyl phenol, 3,5-dimethyl phenol (3,5-xylenol), 2,3-dimethyl phenol, and 3,4-dimethyl phenol is produced during the conversion of ethanol to the functionalized lower hydrocarbon. In some embodiments, the co-product is propylene. In further embodiments, the propylene is recovered. In other embodiments, the propylene is recovered by pressure swing adsorption. In some embodiments, the propylene is generated from ethanol at a yield of at least about 5% of the maximum theoretical molar yield. In other embodiments, the propylene is generated from ethanol at a yield of at least about 10% of the maximum theoretical molar yield. In some embodiments, the co-product is isobutylene. In other embodiments, the isobutylene is recovered. In further embodiments, the isobutylene is recovered by pressure swing adsorption. In some embodiments, the isobutylene is generated from ethanol at a yield of at least about 5% of the maximum theoretical molar yield. In other embodiments, the isobutylene is generated from ethanol at a yield of at least about 10% of the maximum theoretical molar yield. In some embodiments, the co-product is acetone. In other embodiments, the acetone is recovered. In some embodiments, the functionalized lower hydrocarbon includes acetone, wherein at least a fraction of the acetone is recycled back to the reactor feed to convert acetone to isobutylene. In some embodiments, the acetone is converted to isobutylene by contacting it with a $Zn_xZr_yA_vQ_sMn_wO_z$ mixed oxide catalyst. In other embodiments, the acetone is converted to isobutylene by contacting it with a zeolite catalyst. In further embodiments, the zeolite catalyst is an alkali metal ion-exchanged BEA zeolite catalyst or a β-zeolite catalyst.

In some embodiments, the co-product is hydrogen. In other embodiments, the hydrogen is recovered. In still other embodiments, the hydrogen is recovered using a hydrogen recovery system that comprises one or more units configured for condensation, amine scrubbing, pressure swing adsorption, cryogenic purification, flow of gaseous waste stream through a hydrogen-permeable membrane, flow of gaseous waste stream through a palladium membrane, flow of gaseous waste stream through a hydrocarbon absorption medium, flow of gaseous waste stream through a gas expansion unit, flow of the gaseous waste stream through a water gas shift chemical converter unit, or combinations thereof.

In other embodiments, the co-product is carbon dioxide. In some embodiments, the carbon dioxide is recovered. In other embodiments, the carbon dioxide is recovered by pressure swing adsorption, temperature swing adsorption, cryogenic purification, membrane separation, or combinations thereof.

In some embodiments, the co-product is methane. In other embodiments, the methane is recovered. In still other embodiments, the methane is recovered by pressure swing adsorption, temperature swing adsorption, cryogenic purification, membrane separation, or combinations thereof.

In other embodiments, wherein the co-product is selected from phenol, 2-methyl phenol, 3-methyl phenol (meta-cresol), 2,5-dimethyl phenol, 3,5-dimethyl phenol (3,5-xylenol), 2,3-dimethyl phenol, and 3,4-dimethyl phenol. In another embodiment, each of the phenol, 2-methyl phenol, 3-methyl phenol (meta-cresol), 2,5-dimethyl phenol, 3,5-dimethyl phenol (3,5-xylenol), 2,3-dimethyl phenol, and 3,4-dimethyl phenol is produced. In some embodiments, the co-product is recovered by distillation.

In some embodiments, a functionalized lower hydrocarbon is prepared by the process of any process disclosed herein. In other embodiments, at least one product selected from propylene, acetone, hydrogen, carbon dioxide, methane, 2-pentanone, mesityl oxide, methyl isobutylketone, 3-methyl-2-butanone, phenol, 2-methyl phenol, 3-methyl phenol (meta-cresol), 2,5-dimethyl phenol, 3,5-dimethyl phenol (3,5-xylenol), 2,3-dimethyl phenol, and 3,4-dimethyl phenol is prepared by a process disclosed herein.

In some embodiments, a process for preparing a functionalized lower hydrocarbon, comprises: (a) feeding to a reactor a reactor feed comprising ethanol; and (b) contacting the ethanol in the reactor with a bifunctional heterogeneous catalyst comprising an acid functionality and a base functionality, whereby ethanol is converted to the functionalized lower hydrocarbon. The basic functionality is selected from one or more of the following: (i) Ca, Fe, Zn, Ce, Sn, K, Ba, U, Hf, Mn, Sb, Al, Nb, Sc, In, V, Cr, Mo, Ni, Co, Cu, Na, Cs, Rb, B, Mg, Sr, Cd, La, Y, hydrotalcite, zinc-aluminate, phosphate, and combinations thereof; (ii) oxides from the group of Ti, V, Nb, Ta, Mo, Cr, W, Mn, Re, Al, Ga, Fe, Co, Ir, Ni, Si, Cu, Sn, Cd, P, Pd, Pt, and combinations thereof; and (iii) combinations of (i) and (ii). The acid functionality is selected from one or more of Zr, Ti, Si, Ce, Co, Sn, Al; oxides thereof; zeolites; and amorphous silica alumina. In some embodiments, the functionalized lower hydrocarbon is isobutylene. In other embodiments, the functionalized lower hydrocarbon is propylene. In some embodiments, the process further comprises step (c) of recovering the functionalized lower hydrocarbon. In some embodiments, the functionalized lower hydrocarbon recovered in step (c) is isobutylene. In some embodiments, the functionalized lower hydrocarbon recovered in step (c) is propylene.

In some embodiments, the ethanol is bio-based ethanol. In some embodiments, the reactor feed comprises ethanol at a molar concentration of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%. In some embodiments, the reactor feed comprises ethanol and at least one constituent selected from water, methanol, one or more fusel alcohols, one or more diluents, and combinations thereof. In some embodiments, the reactor feed comprises ethanol and water. In some embodiments, the reactor feed comprises at least one diluent. In some embodiments, the diluent is selected from carbon dioxide, nitrogen, methane, ethane, propane, hydrogen, carbon monoxide, and mixtures thereof.

In some embodiments, the ethanol is contacted with the bifunctional heterogeneous catalyst at a temperature in the range of about 300° C. to about 600° C. In some embodiments, the ethanol is contacted with the bifunctional heterogeneous catalyst at a weight hourly space velocity range of about 0.1 hr$^{-1}$ to about 2.0 hr$^{-1}$.

In some embodiments, the acid functionality is provided by one or more metal oxides in the bifunctional heterogeneous catalyst in the reactor. In some embodiments, the acid functionality is selected from zirconia, titania, silica, and combinations thereof.

In some embodiments, at least one promoter is utilized. In other embodiments, the promoter is selected from tin, copper, rhenium, ruthenium, gold, silver, and combinations thereof.

In some embodiments, the isobutylene is recovered using distillation. In other embodiments, the isobutylene is recovered using acid extraction.

In some embodiments, the residual water generated as a by-product during the conversion of ethanol to isobutylene is isolated. In other embodiments, the isolated residual water is recycled back to the front end of the reactor.

In some embodiments, the bifunctional heterogeneous catalyst is regenerated in situ. In some embodiments, the reactor is selected from a fixed-bed, adiabatic, fluid-bed, transport bed, and moving bed reactor. In other embodiments, the reactor is a fixed-bed reactor.

In some embodiments, at least one co-product selected from acetone, hydrogen, carbon dioxide, methane, phenol, 2-methyl phenol, 3-methyl phenol (meta-cresol), 2,5-dimethyl phenol, 3,5-dimethyl phenol (3,5-xylenol), 2,3-dimethyl phenol, and 3,4-dimethyl phenol is produced during the conversion of ethanol to the functionalized lower hydrocarbon. In some embodiments, a functionalized lower hydrocarbon selected from isobutylene and propylene is prepared by a process disclosed herein.

In some embodiments, a process for preparing a jet fuel or jet fuel blendstock, comprises: (a) preparing isobutylene by a process disclosed herein; and (b) converting said isobutylene into a jet fuel or jet fuel blendstock.

In some embodiments, a process for preparing isooctane comprises: (a) preparing isobutylene by a process disclosed herein; and (b) converting said isobutylene into isooctane.

In some embodiments, a process for preparing para-xylene comprises: (a) preparing isobutylene by a process disclosed herein; and (b) converting said isobutylene into para-xylene.

In some embodiments, a process for preparing methacrolein comprises: (a) preparing isobutylene by a process disclosed herein; and (b) converting said isobutylene into methacrolein.

In some embodiments, a process for preparing methylmethacrylate comprises: (a) preparing isobutylene by a process disclosed herein; (b) converting said isobutylene into methacrolein; (c) oxidizing the methacrolein of (b) into methacrylic acid; and (e) esterifying the methacrylic acid of (c) into methylmethacrylate.

In some embodiments, a process for preparing butyl rubber comprises: (a) preparing isobutylene by a process disclosed herein; and (b) converting said isobutylene into butyl rubber.

DETAILED DESCRIPTION

Definitions

Figure 1:
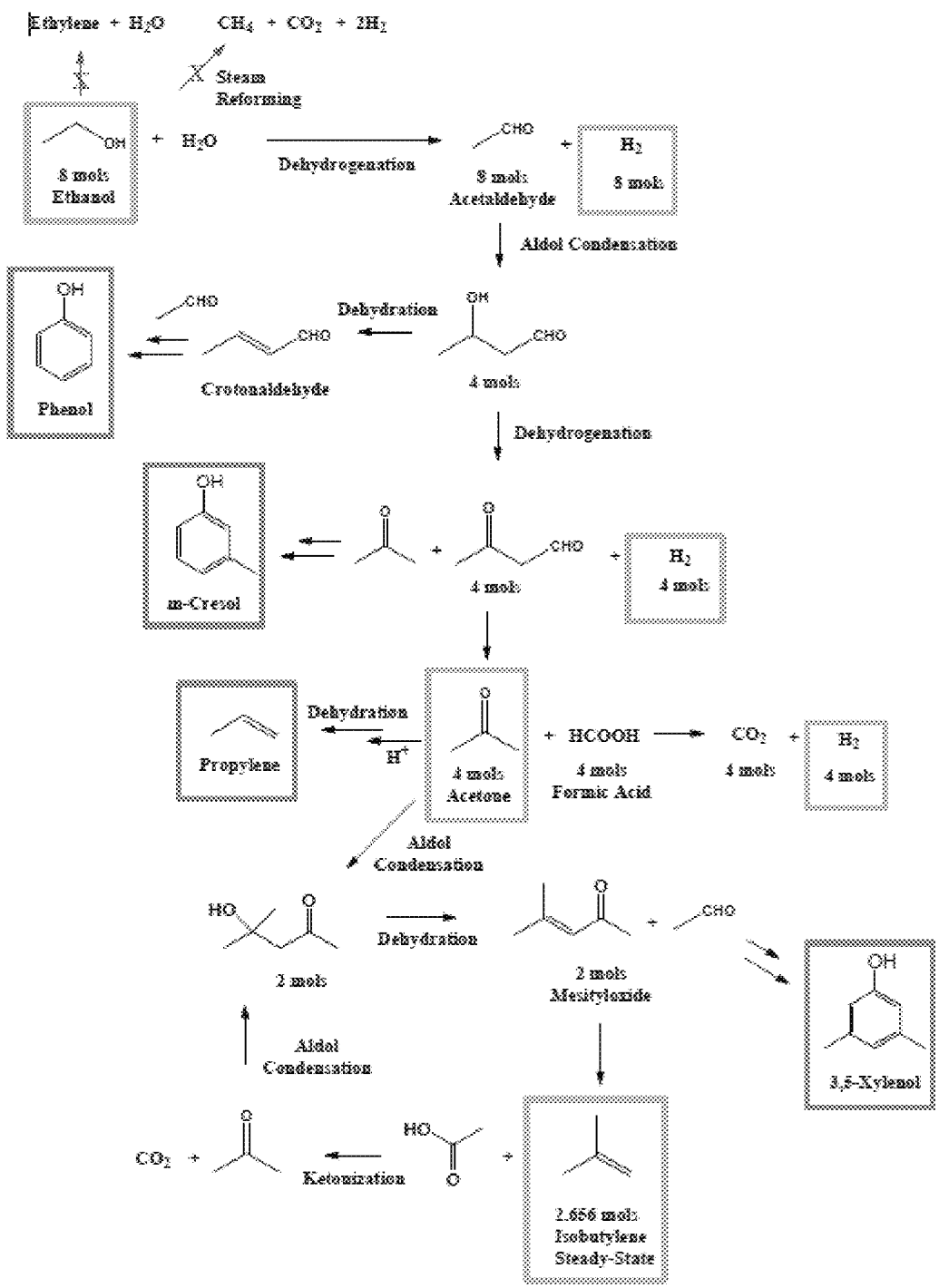
FIG. 1 illustrates the reaction scheme by which the inventive process and/or the inventive catalyst converts ethanol into isobutylene, propylene, phenol, meta-cresol, 3,5-xylenol, acetone, and hydrogen.

As used throughout the specification, "a" can include referents to the singular or plural. Accordingly, a functionalized lower hydrocarbon can include one or more than one functionalized hydrocarbon as defined below.

Throughout the present specification, the terms "about" and/or "approximately" can be used in conjunction with numerical values and/or ranges. The term "about" is understood to mean those values near to a recited value. For example, "about 40 [units]" can mean within ±25% of 40 (e.g., from 30 to 50), within ±20%, ±15%, ±10%, ±9%, ±8%, ±7%, ±6%, ±5%, ±4%, ±3%, ±2%, ±1%, less than ±1%, or any other value or range of values therein or therebelow. Furthermore, the phrases "less than about [a value]" or "greater than about [a value]" should be understood in view of the definition of the term "about" provided herein. The terms "about" and "approximately" can be used interchangeably.

Throughout the present specification, the terms "functionalized lower hydrocarbon" is used to indicate the product or products of a process described herein. Functionalized lower hydrocarbons include linear, branched, and cyclic molecules having up to about 10 carbons. The terms include either a homologated (one carbon added relative to the carbon number of the starting material) or lengthened (two or more carbons added relative to the carbon number of the starting material) alkane, or a product with the same or greater carbon number relative to the starting material but with some sort of functionalization introduced (e.g., a carbonyl, a hydroxyl, and/or a degree of unsaturation, e.g., a double bond), and mixtures thereof. Non-limiting examples of functionalized lower hydrocarbons produced by a process disclosed herein include propylene, isobutylene, and acetone.

The terms also include co-products produced by a catalytic reaction of the present application. For example, co-products include a product obtained from the reaction of at least one reactant with at least one intermediate, or a product obtained from the reaction of multiple intermediates. Co-products include linear, branched, cyclic molecules having up to about 10 carbons. Co-products also includes non-hydrocarbon molecules generated by a process of converting starting material. Non-limiting examples of co-produced produced by a process disclosed herein include, isobutylene, acetone, hydrogen, carbon dioxide, methane, phenol, 2-pentanone, mesityl oxide, methyl isobutylketone, 3-methyl-2-butanone, 2-methyl phenol, 3-methyl phenol (meta-cresol), 2,5-dimethyl phenol, 3,5-dimethyl phenol (3,5-xylenol), 2,3-dimethyl phenol, and 3,4-dimethyl phenol.

Throughout the present specification, the terms "carbon selectivity" or "selectivity" is used to indicate the selectivity of the process to produce a particular functionalized lower hydrocarbon. In some embodiments, the catalyst, preparation of the catalyst, and reaction parameters, e.g., superficial velocity, influence the yield of a particular functionalized lower hydrocarbon.

As used herein, the phrases "molar concentration" and/or "mole concentration" are used to characterize the mole percent of a particular stream constituent, e.g., ethanol, water, etc. The molar concentration is calculated by dividing the number of moles of a particular stream constituent, e.g., ethanol, by the total number of moles in the process stream. See, e.g., page 34 of Felder, R. M and Rousseau, R. W., 1978, Elementary Principles of Chemical Processes, by John Wiley & Sons, Inc.

As used herein, the term "yield" in reference to a yield of a functionalized lower hydrocarbon, e.g., isobutylene, is expressed as a percentage of the maximum theoretical yield, which defines the maximum amount of the functionalized lower hydrocarbon, e.g., isobutylene, that can be generated per a given amount of ethanol as dictated by the stoichiometry of the catalytic reaction used to make the functionalized lower hydrocarbon, e.g., isobutylene. For example, the theoretical yield for the catalytic reaction described herein is 33.3%, i.e., 1 mol of isobutylene produced per every 3 mols of ethanol substrate in the reactor feed. As such, if 24% of the ethanol carbon substrate is converted to isobutylene, the yield, as used herein, would be expressed as 72%, which is obtained by taking a 24% conversion to isobutylene divided by a potential 33.3% maximum theoretical yield. In another example, the theoretical yield for the catalytic reaction described herein is 50%, i.e., 1 mol of propylene produced per every 2 mols of ethanol substrate in the reactor feed. As such, if 40% of the ethanol carbon substrate is converted to propylene, the yield, as used herein, would be expressed as 80.0%, which is obtained by taking a 40% conversion to propylene divided by a potential 50% maximum theoretical yield. Conversely, on a carbon atom basis, the theoretical yield to propylene is 75%, which is expressed as 3 carbon atoms in propylene (1 mol) divided by 4 carbon atoms from ethanol (2 mols). For the conversion of ethanol to acetone, the theoretical yield for the catalytic reaction described herein is 50%, i.e., 1 mol of acetone produced per every 2 mols of ethanol substrate in the reactor feed.

Ethanol to Functionalized Lower Hydrocarbon Conversion

This application relates to the production of functionalized lower hydrocarbons and more particularly to the process of converting ethanol to functionalized lower hydrocarbons, e.g., isobutylene, propylene, and/or acetone. In particular embodiments, the ethanol to be converted is present at molar concentrations in the reactor feed equal to or exceeding 14%. In other particular embodiments, catalysts used in the process of converting of ethanol to functionalized lower hydrocarbons enables high carbon selectivities, high purity, and/or improved yields.

As noted above, aspects of the present application are directed to a process for preparing functionalized lower hydrocarbons, comprising: (a) feeding to a reactor a reactor feed comprising ethanol at a molar concentration; and (b) contacting the ethanol with a catalyst (e.g., a $Zn_xZr_yA_vQ_sM$-$n_wO_z$ mixed oxide catalyst or a bifunctional heterogeneous catalyst) in the reactor, whereby ethanol is converted to the functionalized lower hydrocarbons. In one such embodiment, the ethanol is covered to at least one functionalized lower hydrocarbon at a yield of at least about 30%. In another embodiment, the ethanol is converted to at least one functionalized lower hydrocarbon at a yield of at least 60%. In one embodiment, the reactor feed comprises ethanol at a molar concentration of at least about 5%. In one embodiment, the reactor feed comprises ethanol at a molar concentration of at least about 10%. In one embodiment, the reactor feed comprises ethanol at a molar concentration of at least about 14%. In one embodiment, the reactor feed comprises ethanol at a molar concentration of at least about 15%. In one embodiment, the reactor feed comprises ethanol at a molar concentration of at least about 20%. In another embodiment, the reactor feed comprises ethanol at a molar concentration of at least about 25%. In yet another embodiment, the reactor feed comprises ethanol at a molar concentration of at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%. In an exemplary embodiment, the reactor feed is the azeotropic composition of an ethanol-water water mixture obtained from an ethanol production plant prior to dehydration has an ethanol molar concentration of between about 80% and about 95%. In additional exemplary embodiments, the reactor feed comprises ethanol at a molar concentration selected from the group consisting of 14.8%, 25.3% and higher, 33.6% or higher, 37% or higher, and higher with approximate steam to carbon ratios of 0.4 to 1.3 or of 0.05 to 3.0.

In another aspect, the present application is directed to a process for preparing at least one functionalized lower hydrocarbon, comprising: (a) feeding to a reactor a reactor feed comprising ethanol at a molar concentration of at least about 14%; and (b) contacting the ethanol with a $Zn_xZr_yA_vQ_sMn_wO_z$ mixed oxide catalyst in the reactor, whereby ethanol is converted to at least one functionalized hydrocarbon at a yield of at least about 30%. In one embodiment, the reactor feed comprises ethanol at a molar concentration of at least about 20%. In another embodiment, the reactor feed comprises ethanol at a molar concentration of at least about 25%. In yet another embodiment, the reactor feed comprises ethanol at a molar concentration of at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%. In an exemplary embodiment, the reactor feed is the azeotropic composition of an ethanol-water mixture obtained from an ethanol production plant prior to dehydration and has an ethanol molar concentration of between about 80% and about 95%. In additional exemplary embodiments, the reactor feed comprises ethanol at a molar concentration selected from the group consisting of about 14.8% and higher, about 25% and higher, about 33.6% and higher, and about 37% and higher, with approximate steam to carbon ratios of 0.4 to 1.3, or 0.05 to 3.0, respectively.

As noted above, in a second aspect, the application relates to a process for preparing at least one functionalized lower hydrocarbon, comprising: (a) feeding to a reactor a reactor feed comprising ethanol; and (b) contacting the ethanol in the reactor with a bifunctional heterogeneous catalyst comprising acid and base functionality, whereby ethanol is converted to at least one functionalized lower hydrocarbon. In some embodiments, the reactor feed comprises ethanol at a molar concentration of at least about 5%. In one embodiment, the reactor feed comprises ethanol at a molar concentration of at least about 10%. In another embodiment, the reactor feed comprises ethanol at a molar concentration of at least about 14%. In another embodiment, the reactor feed comprises ethanol at a molar concentration of at least about 15%. In yet another embodiment, the reactor feed comprises ethanol at a molar concentration of at least about 20%. In yet another embodiment, the reactor feed comprises ethanol at a molar concentration of at least about 25%. In yet another embodiment, the reactor feed comprises ethanol at a molar concentration of at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%. In an exemplary embodiment, the reactor feed is the azeotropic composition of an ethanol-water water mixture obtained from an ethanol production plant prior to dehydration and has an ethanol molar concentration of between about 80% and about 95%.

Ethanol is a 2-carbon alcohol available from a variety of sources. Ethanol may be produced both as a petrochemical, through the hydration of ethylene, and via biological processes, such as the fermentation of sugars with yeast. Which process is more economical depends on prevailing prices of petroleum and grain feed stocks. In addition, ethanol can be produced from biomass-generated syngas, which involves first converting biomass, e.g., prairie grasses, wood chips, paper wastes, agricultural wastes, etc., to syngas via a process called gasification. The syngas can then be converted to ethanol and hydrogen using either a microbial catalyst, e.g., bacteria, or a metal catalyst In addition to biomass, a number of other feedstocks can be used to produce syngas including natural gas and coal.

As described above, this application provides a process for converting ethanol to at least one functionalized lower hydrocarbon. In certain embodiments, this application provides for a process of converting ethanol at molar concentrations equal to or exceeding 14% to at least one functionalize lower hydrocarbon. In certain embodiments, the ethanol to be converted to a functionalized lower hydrocarbon is obtained from the fermentation of biomass. The term "biomass" as used herein refers primarily to the stems, leaves, and starch-containing portions of green plants, and is mainly comprised of starch, lignin, cellulose, hemicellulose, and/or pectin. Biomass can be decomposed by either chemical or enzymatic treatment to the monomeric sugars and phenols of which it is composed. This resulting material, called biomass hydrolysate, is neutralized and treated to remove trace amounts of organic material that may adversely affect the biocatalyst, and is then used as a feedstock for fermentations using a biocatalyst. Exemplary sources of biomass include corn and sugar cane. Additional sources include agriculture and municipal waste, which may consist primarily of lignocellulosic biomass.

In exemplary embodiments described herein, the ethanol to be converted to a functionalized lower hydrocarbon is bio-based ethanol, i.e., bio-ethanol. The term "bio-based" as used herein in reference to a particular compound or product means at least about 50 wt % of the compound or product is derived from a non-petroleum feedstock. In one embodiment, at least about 50 wt % of the ethanol is derived from a non-petroleum feedstock. In another embodiment, at least about 60 wt % of the ethanol is derived from a non-petroleum feedstock. In yet additional embodiments, at least about 70 wt %, at least about 80 wt %, at least about 90%, or at least about 95 wt % of the ethanol is derived from a non-petroleum feedstock. In one exemplary embodiment, all or substantially all of the ethanol to be converted to a functionalized lower hydrocarbon is derived from a non-petroleum feedstock. In some embodiments, the ethanol to be converted to a functionalized lower hydrocarbon is produced in an ethanol bio-refinery via the fermentation of sugars by yeast.

In certain embodiments, the ethanol to be converted to a functionalized lower hydrocarbon is obtained from biomass-generated syngas. In certain other embodiments, the ethanol to be converted to a functionalized lower hydrocarbon is obtained from syngas that has been derived from natural gas, coal, or a combination of natural gas and coal. In still other embodiments, the ethanol to be converted to a functionalized lower hydrocarbon is obtained from a combination of biomass-generated syngas and syngas that has been derived from natural gas, coal, or a combination of natural gas and coal.

In certain other embodiments, the ethanol to be converted to a functionalized lower hydrocarbon is petroleum-based ethanol. In one embodiment, the petroleum-based ethanol is synthesized from ethylene. To produce ethanol by chemical synthesis, petroleum-derived ethylene may be hydrolyzed using a catalyst such as sulfuric acid.

In some embodiments, the ethanol to be converted to a functionalized lower hydrocarbon is fuel-grade ethanol. As used herein, fuel-grade ethanol is ethanol that meets all the criteria for the standard ASTM specification of D4806-13a, provided, however, that the fuel-grade ethanol as described herein and used in the process of the present application may or may not comprise denaturants.

In an exemplary embodiment, the reactor feed is the azeotropic composition of an ethanol-water mixture obtained from an ethanol production plant prior to dehydration using conventional methods such as sieves. The ethanol-water mixture will typically comprise ethanol, water, and small amounts of fusel alcohols. The azeotropic composition of an ethanol-water mixture obtained from an ethanol production plant prior to dehydration may have a molar concentration of about 80%, 81%, 82%, 83%, 84%, 85%, 86%, 87%, 88%, 89%, 90%, 91%, 92%, 93%, 94%, or 95% ethanol. In an exemplary embodiment, the azeotropic composition of an ethanol-water water mixture obtained from an ethanol production plant prior to dehydration has a molar concentration of about 88%.

In certain embodiments, the reactor feed comprises minor amounts of compounds in addition to the ethanol, such as water, methanol, fusel alcohols, diluents, and combinations thereof. Thus, in some embodiments, the reactor feed comprises ethanol and at least one additional constituent selected from water, methanol, one or more fusel alcohols, and a diluent.

In one embodiment, the reactor feed comprises ethanol and water. In various embodiments described herein, the reactor feed comprises water at a molar concentration of less than about 85%. In one embodiment, the reactor feed comprises water at a molar concentration of less than about 75%. In another embodiment, the reactor feed comprises water at a molar concentration of less than about 65%. In yet another embodiment, the reactor feed comprises water at a molar concentration of less than about 60%, less than about 55%, less than about 50%, less than about 45%, less than about 40%, less than about 35%, less than about 30%, less than about 25%, less than about 20%, or less than about 15%. In an exemplary embodiment, the reactor feed comprises water at a molar concentration of less than about 12%. In another exemplary embodiment, the reactor feed comprises water at a molar concentration of less than about 10%. In yet another exemplary embodiment, the reactor feed comprises water at a molar concentration of less than about 5%.

In some embodiments, the reactor feed consists of ethanol and water. In certain other embodiments, the reactor feed consists of ethanol, water, and methanol. In yet certain other embodiments, the reactor feed consists of ethanol, water, methanol, and trace amounts of fusel alcohols, such as 1-propanol, isobutanol, 2-methyl-1-butanol, and isopentanol. In further embodiments, additional reactor feed stream constituents may be added, including diluents. In some embodiments, additional diluents, aside from nitrogen, may be selected from carbon dioxide, methane, ethane, propane, and mixtures thereof.

In further embodiments, the reactor feed is preferably free or substantially free of nitrogen. In one embodiment, the reactor feed comprises nitrogen at a molar concentration of less than about 10%. In another embodiment, the reactor feed comprises nitrogen at a molar concentration of less than about 5%. In yet another embodiment, the reactor feed comprises nitrogen at a molar concentration of less than about 2%, less than about 1%, less than about 0.5%, or less than about 0.1%. In an exemplary embodiment, the reactor feed is free of nitrogen.

As described herein, the temperature, catalyst, reactor configuration, weight hourly space velocity, superficial gas velocity, and pressure are all parameters that can affect the conversion and selectivity. The relationships among these parameters may be adjusted to effect the desired conversion, reaction rate, and selectivity in the reaction of the process.

In certain embodiments, ethanol is contacted with a $Zn_xZr_yA_vQ_sMn_wO_z$ mixed oxide catalyst or a bifunctional heterogeneous catalyst at a temperature range of about 400° C. to about 600° C. In a more specific embodiment, ethanol is contacted with a $Zn_xZr_yA_vQ_sMn_wO_z$ mixed oxide catalyst or a bifunctional heterogeneous catalyst mixed oxide catalyst at a temperature range of about 440° C. to about 500° C. In an exemplary embodiment, ethanol is contacted with a $Zn_xZr_yA_vQ_sMn_wO_z$ mixed oxide catalyst or a bifunctional heterogeneous catalyst mixed oxide catalyst at a temperature of or about 440° C. In another exemplary embodiment, ethanol is contacted with a $Zn_xZr_yA_vQ_sMn_wO_z$ mixed oxide catalyst or a bifunctional heterogeneous catalyst mixed oxide catalyst at a temperature of or about 450° C. In yet another exemplary embodiment, ethanol is contacted with a $Zn_xZr_yA_vQ_sMn_wO_z$ mixed oxide catalyst or a bifunctional heterogeneous catalyst mixed oxide catalyst at a temperature of or about 460° C. In still another exemplary embodiment, ethanol is contacted with a $Zn_xZr_yA_vQ_sMn_wO_z$ mixed oxide catalyst or a bifunctional heterogeneous catalyst mixed oxide catalyst at a temperature of or about 485° C.

In certain additional embodiments, ethanol is contacted with a $Zn_xZr_yA_vQ_sMn_wO_z$ mixed oxide catalyst or a bifunctional heterogeneous catalyst at a weight hourly space velocity range of about 0.1 hr$^{-1}$ to about 2.5 hr$^{-1}$. In a more specific embodiment, ethanol is contacted with a $Zn_xZr_yA_vQ_sMn_wO_z$ mixed oxide catalyst or a bifunctional heterogeneous catalyst at a weight hourly space velocity range of about 0.2 hr$^{-1}$ to about 1 hr$^{-1}$. In a further embodiment, ethanol is contacted with a $Zn_xZr_yA_vQ_sMn_wO_z$ mixed oxide catalyst or a bifunctional heterogeneous catalyst at a weight hourly space velocity range of about 0.3 hr$^{-1}$ to about 1.1 hr$^{-1}$. In yet another embodiment, ethanol is contacted with a $Zn_xZr_yA_vQ_sMn_wO_z$ mixed oxide catalyst or the bifunctional heterogeneous catalyst at a weight hourly space velocity range of about 0.4 hr$^{-1}$ to about 0.8 hr$^{-1}$. In yet another embodiment, ethanol is contacted with a $Zn_xZr_yA_vQ_sMn_wO_z$ mixed oxide catalyst or the bifunctional heterogeneous catalyst at a weight hourly space velocity range of about 0.55 hr$^{-1}$ to about 0.75 hr$^{-1}$. In an exemplary embodiment, ethanol is contacted with a $Zn_xZr_yA_vQ_sMn_wO_z$ mixed oxide catalyst or a bifunctional heterogeneous catalyst at a weight hourly space velocity of or about 1.1 hr$^{-1}$.

In some embodiments, the ethanol to functionalized lower hydrocarbon reaction is carried out at a residence time range of about 0.5 g·s·STP mL$^{-1}$ to about 4.0 g·s·STP mL$^{-1}$. In a more specific embodiment, the ethanol to functionalized lower hydrocarbon reaction is carried out at a residence time range of about 1.0 g·s·STP mL$^{-1}$ to about 3.0 g·s·STP mL$^{-1}$. In a further embodiment, the ethanol to functionalized lower hydrocarbon reaction is carried out at a residence time range of about 1.5 g·s·STP mL$^{-1}$ to about 2.5 g·s·STP mL$^{-1}$.

One skilled in the art will recognize that longer on-stream times and less regeneration cycles increase catalyst life and lower overall production costs due to less process downtime.

Mixed Oxide Catalyst

In some embodiments, a $Zn_xZr_yA_vQ_sMn_wO_z$ mixed oxide catalyst is used in the process to convert ethanol to functionalized lower hydrocarbons. In some embodiments, X is a value from is 1 to 10, including all values and subranges therein. In some embodiments, Y is a value from 1 to 100, including all values and subranges therein. In other embodiments, A is Al, Si, Mg, or Cu, Ti, and V is a value from 0 to 100, including all values and subranges therein. In further embodiments, Q is Al, Si, Mg, or Cu, Ti, and V is a value from 0 to 100, including all values and subranges therein. In still other embodiments, W is a value from 0 to 30, including all values and subranges therein. In yet other embodiments, Z is a value from 5 to 250, including all values and subranges therein.

In one embodiment of the present disclosure, the process for preparing functionalized lower hydrocarbons (e.g., isobutylene or propylene) involves $Zn_xZr_yO_z$ mixed oxide catalyst wherein the ratio of Zn/Zr (x:y) in a $Zn_xZr_yO_z$ mixed oxide catalyst is in a range of about 1:1 to about 1:100, of about 1:2 to about 1:50, of about 1:5 to about 1:25, or of about 1:8 to about 1:36. In a more specific exemplary embodiment, the ratio of Zn/Zr (x:y) in the $Zn_xZr_yO_z$ mixed oxide catalyst used in the ethanol to isobutylene conversion is about 1:12. In another specific exemplary embodiment, the ratio of Zn/Zr (x:y) in the $Zn_xZr_yO_z$ mixed oxide catalyst used in the ethanol to isobutylene conversion is about 1:18. In yet another specific exemplary embodiment, the ratio of Zn/Zr (x:y) in the $Zn_xZr_yO_z$ mixed oxide catalyst used in the ethanol to isobutylene conversion is about 1:25.

In some embodiment, V is 0 and S is 0. In some such embodiments, the ratio of Zn/Zr/Mn (x:y:w) in the $Zn_xZr_yMn_wO_z$ mixed oxide catalyst is in a range of about 1:1:1 to about 1:100:30. In a more specific embodiment, the ratio of Zn/Zr/Mn (x:y:w) in the $Zn_xZr_yMn_wO_z$ mixed oxide catalyst is in a range of about 1:2:30 to about 1:50:30. In a further embodiment, the ratio of Zn/Zr/Mn (x:y:w) in the $Zn_xZr_yMn_wO_z$ mixed oxide catalyst is in a range of about 1:5:1 to about 1:25:30. In another embodiment, the ratio of Zn/Zr/Mn (x:y:w) in the $Zn_xZr_yMn_wO_z$ mixed oxide catalyst is in a range of about 1:8:1 to about 1:20:30. In one exemplary embodiment, the ratio of Zn/Zr/Mn (x:y:w) in the $Zn_xZr_yMn_wO_z$ mixed oxide catalyst is about 1:8:1.

In some embodiments, A is Si, V is greater than or equal to 1, S is 0, and W is 0. In some such embodiments, the ratio of Zn/Zr/Si (x:y:v) in the $Zn_xZr_ySi_vO_z$ mixed oxide catalyst is in a range of about 1:1:1 to about 1:100:100. In a more specific embodiment, the ratio of Zn/Zr/Si (x:y:v) in the $Zn_xZr_ySi_vO_z$ mixed oxide catalyst is in a range of about 1:2:2 to about 1:50:50. In a further embodiment, the ratio of Zn/Zr/Si (x:y:v) in the $Zn_xZr_ySi_vO_z$ mixed oxide catalyst is in a range of about 1:5:5 to about 1:25:25. In another embodiment, the ratio of Zn/Zr/Si (x:y:v) in the $Zn_xZr_ySi_vO_z$ mixed oxide catalyst is in a range of about 1:8:8 to about 1:25:25. In one exemplary embodiment, the ratio of Zn/Zr/Si (x:y:v) in the $Zn_xZr_ySi_vO_z$ mixed oxide catalyst is about 1:12:2.

In some embodiments, A is Al, S is 0, and W is 0. In one embodiment, the ratio of Zn/Zr/Al (x:y:v) in te $Zn_xZr_yAl_vO_z$ mixed oxide catalyst is in a range of about 1:1:1 to about 1:100:100, about 1:2:2 to about 1:50:50, about 1:5:5 to about 1:25:25, or about 1:8:8 to about 1:20:20. In one exemplary embodiment, the process for preparing high purity propylene involves $Zn_xZr_yAl_vO_z$ mixed oxide catalyst wherein the ratio of Zn/Zr/Al (x:y:v) is about 1:12:1.

In some embodiments, A is Al, V is greater than or equal to 1, Q is Si, S is greater than or equal to 1, and W is 0. In one embodiment, the ratio of Zn/Zr/Al/Si (x:y:v:s) in the $Zn_xZr_yAl_vSi_sO_z$ mixed oxide catalyst is in a range of about 1:1:1:1 to about 1:100:100:100. In other embodiments, the ratio of Zn/Zr/Al/Si (x:y:v:s) in the $Zn_xZr_yAl_vSi_sO_z$ mixed oxide catalyst is in a range of about 1:2:2:2 to about 1:50:50:50. In still other embodiments, the ratio of Zn/Zr/Al/Si (x:y:v:s) in the $Zn_xZr_yAl_vSi_sO_z$ mixed oxide catalyst is in a range of about 1:5:5:5 to about 1:25:25:25. In yet other embodiments, the ratio of Zn/Zr/Al/Si (x:y:v:s) in the $Zn_xZr_yAl_vSi_sO_z$ mixed oxide catalyst is in a range of about 1:8:8:8 to about 1:20:20:20. In an exemplary embodiment, the ratio of Zn/Zr/Al/Si (x:y:v:s) in the $Zn_xZr_yAl_vSi_sO_z$ mixed oxide catalyst is about 1:12:2:2.

In some embodiments, A is Mg or Cu, V is greater than or equal to 1, W is 0, and S is 0. In some embodiments, the ratio of Zn/Mg/Zr or Zn/Cu/Zr (x:v:y) in the $Zn_xMg_vZr_yO_z$ or $Zn_xCu_vZr_yO_z$ mixed oxide catalyst is in a range of about 1:1:1 to about 1:1:100. In a more specific embodiment, the ratio of Zn/Mg/Zr or Zn/Cu/Zr (x:v:y) in the $Zn_xMg_vZr_yO_z$ or $Zn_xCu_vZr_yO_z$ mixed oxide catalyst is in a range of about 1:1:2 to about 1:1:50. In a further embodiment, the ratio of Zn/Mg/Zr or Zn/Cu/Zr (x:v:y) in the $Zn_xMg_vZr_yO_z$ or $Zn_xCu_vZr_yO_z$ mixed oxide catalyst is in a range of about 1:1:5 to about 1:1:36. In another embodiment, the ratio of Zn/Mg/Zr or Zn/Cu/Zr (x:v:y) in the $Zn_xMg_vZr_yO_z$ or $Zn_xCu_vZr_yO_z$ mixed oxide catalyst is in a range of about 1:1:12 to about 1:1:25. In one exemplary embodiment, the ratio of Zn/Mg/Zr or Zn/Cu/Zr (x:v:y) in the $Zn_xMg_vZr_yO_z$ or $Zn_xCu_vZr_yO_z$ mixed oxide catalyst is about 1:1:25.

In some embodiments, A is Mg, V is greater than or equal to 1, W is equal to about 1 or greater, and S is 0. In some such embodiments, the ratio of Zn/Mg/Mn/Zr (x:v:w:y) or Zn/Cu/Mn/Zr (x:v:w:y) in the $Zn_xMg_vMn_wZr_yO_z$ or $Zn_xCu_vMn_wZr_yO_z$ mixed oxide catalyst is in a range of about 1:1:1:15 to about 1:10:10:100. In a more specific embodiment, the ratio of Zn/Mg/Mn/Zr (x:v:w:y) or Zn/Cu/Mn/Zr (x:v:w:y) in $Zn_xMg_vMn_wZr_yO_z$ or $Zn_xCu_vMn_wZr_yO_z$ mixed oxide catalyst is in a range of about 1:1:2:2 to about 1:5:5:50. In a further embodiment, the ratio of Zn/Mg/Mn/Zr (x:v:w:y) or Zn/Cu/Mn/Zr (x:v:w:y) in the $Zn_xMg_vMn_wZr_yO_z$ or $Zn_xCu_vMn_wZr_yO_z$ mixed oxide catalyst is in a range of about 1:1:10:5 to about 1:10:10:36. In another embodiment, the ratio of Zn/Mg/Mn/Zr (x:v:w:y) or Zn/Cu/Mn/Zr (x:v:w:y) in the $Zn_xMg_vMn_wZr_yO_z$ or $Zn_xCu_vMn_wZr_yO_z$ mixed oxide catalyst is in a range of about 1:1:2:15 to about 1:10:10:25. In one exemplary embodiment, the ratio of Zn/Mg/Mn/Zr (x:v:w:y) or Zn/Cu/Mn/Zr (x:v:w:y) in the $Zn_xMg_vMn_wZr_yO_z$ or $Zn_xCu_vMn_wZr_yO_z$ mixed oxide catalyst is about 1:1:4:15.

As a person skilled in the art will appreciate, the oxidation states of manganese and copper can be variable, as such the manganese and copper can be present in one or more of a variety of oxidation states within the catalyst materials (e.g. Mn(0), Mn(II), Mn(III), Mn(IV), Cu(I), Cu(II), Cu(III)). The variable oxidation states of Mn and Cu, coupled with the presence of $ZrO_2$, ZnO, MgO, $Al_2O_3$ and a percentage of oxygen vacancies in addition to oxygen bridging between metal oxides makes the exact oxygen ratio per catalyst variable. However, based on the metal oxide ranges defined above one can reasonably expect atomic oxygen ranges to be between about 5 and about 250.

Thus, in some embodiments, z is from about 5 to about 250. In some embodiments, z is from about 5 to about 10, from about 10 to about 15, from about 15 to about 20, from about 20 to about 25, from about 25 to about 30, from about 30 to about 35, from about 35 to about 40, from about 40 to about 45, from about 45 to about 50, from about 50 to about 55, from about 55 to about 60, from about 60 to about 65, from about 65 to about 70, from about 70 to about 75, from about 75 to about 80, from about 80 to about 85, from about 85 to about 90, from about 90 to about 95, from about 95 to about 100, from about 105 to about 110, from about 110 to about 115, from about 115 to about 120, from about 120 to about 125, from about 125 to about 130, from about 130 to about 135, from about 135 to about 140, from about 140 to about 145, from about 145 to about 150, from about 150 to about 155, from about 155 to about 160, from about 160 to about 165, from about 165 to about 170, from about 170 to about 175, from about 175 to about 180, from about 180 to about 185, from about 185 to about 190, from about 190 to about 195, from about 195 to about 200, from about 205 to about 210, from about 210 to about 215, from about 215 to about 220, from about 220 to about 225, from about 225 to about 230, from about 230 to about 235, from about 235 to about 240, from about 240 to about 245, from about 245 to about 250, or any other value or range of values therein.

In some embodiments, the mixed oxide catalyst disclosed used for the conversion of ethanol to functionalized lower hydrocarbons can be prepared by the hard-template method, the co-precipitation method, or the impregnated method.

Hard-Template Method

In some embodiments, a $Zn_xZr_yA_vQ_sMn_wO_z$ mixed oxide catalyst can be prepared by the hard-template method. In a particular embodiment, the $Zn_xZr_yO_z$ mixed oxide catalyst is prepared by the hard-template method.

In some embodiments, a $Zn_xZr_yO_z$ mixed oxide catalyst is prepared using a modified hard-template method. See Jacobsen et al., 2000, *J. Am. Chem. Soc.* 122: 7116-7117. In one embodiment, a conventional carbon support, e.g., a carbon black support is utilized. Carbon black is a form of paracrystalline carbon that has a high surface area-to-volume ratio. Several commercially available carbon black species are known in the art, such as Black Pearl 2000, VXC-200, Vulcan XC-72, Elftex, Mogul, Monarch, Regal, Spheron, Sterling, CSX, CRX, IRX, United, Machem, Shoblack, DL, and Propel from Cabot Corp., and Ketjen Black, commercialized by Akzo Nobel. In an exemplary embodiment, the carbon black utilized is Black Pearl 2000, i.e., BP-2000. In further embodiments, precursor metal salts are added to deionized water to produce an appropriate zinc to zirconium ratio. In additional embodiments, the zinc and zirconium nitrate mixture may be sonicated to produce a clear solution. In further additional embodiments, the sonicated zinc and zirconium nitrate mixture is added to the carbon support, e.g., a carbon black support. In further additional embodiments, the impregnated carbon support, e.g., a carbon black support, may be dried and calcinated at a temperature between 400° C. and 550° C. In an exemplary embodiment, calcination occurs at a first temperature of 400° C. for a first period of time and a second temperature of 550° C. for a second period of time.

In one such embodiment, the catalyst may be prepared by first depositing a soluble zirconium precursor on a conventional carbon support, e.g., a carbon black template, followed by a first calcination step to prepare a zirconium oxide and then deposition of the zinc salt onto the prepared zirconium oxide, followed by second calcination step to prepare the final $Zn_xZr_yO_z$ mixed oxide catalyst.

In some embodiments, the ratio of Zn/Zr (x:y) in a $Zn_xZr_yO_z$ mixed oxide catalyst prepared using the hard-template method is in a range of about 1:1 to about 1:100. In a more specific embodiment, the ratio of Zn/Zr (x:y) in a $Zn_xZr_yO_z$ mixed oxide catalyst prepared using the hard-template method is in a range of about 1:2 to about 1:50. In a further embodiment, the ratio of Zn/Zr (x:y) in a $Zn_xZr_yO_z$ mixed oxide catalyst prepared using the hard-template method is in a range of about 1:8 to about 1:36. In an exemplary embodiment, the ratio of Zn/Zr (x:y) in a $Zn_xZr_yO_z$ mixed oxide catalyst prepared using the hard-template method is in a range of about 1:25.

Co-Precipitation Method

In some embodiments, the $Zn_xZr_yA_vQ_sMn_wO_z$ mixed oxide catalyst can be prepared by the co-precipitation method. In exemplary embodiments, the mixed oxide catalyst prepared by the co-precipitation method is $Zn_xZr_yO_z$. In other exemplary embodiments, the $Zn_xZr_yA_vQ_sMn_wO_z$ mixed oxide catalyst prepared by the co-precipitation method is $Zn_xZr_ySi_sO_z$. In other exemplary embodiments, the $Zn_xZr_yA_vQ_sMn_wO_z$ mixed oxide catalyst prepared by the co-precipitation method is $Zn_xZr_yAl_vO_z$. In other exemplary embodiments, the $Zn_xZr_yA_vQ_sMn_wO_z$ mixed oxide catalyst prepared by the co-precipitation method is $Zn_xZr_yAl_vSi_wO_z$. In still other exemplary embodiments, the $Zn_xZr_yA_vQ_sMn_wO_z$ mixed oxide catalyst prepared by the co-precipitation method is $Zn_xMg_yZr_yO_z$ or $Zn_xCu_vZr_yO_z$.

Based on acidity characterization measurements, via pyridine thermal desorption technique, a $Zn_xZr_yA_vQ_sMn_wO_z$ mixed oxide catalyst prepared via co-precipitation technique has a more pronounced bimodal distribution exhibiting lower levels of weaker acid sites with higher levels of stronger acid sites in comparison to the hard templated, the impregnated, and inverse co-precipitated catalysts. In addition, the unique morphology of the co-precipitated catalyst demands a significantly different $Zn_xZr_yO_z$ mixed oxide ratio to afford good ethanol conversion to functionalized lower hydrocarbons. As a non-limiting example, selective ethanol to isobutylene conversion is achieved via a co-precipitated $Zn_xZr_yO_z$ with a Zn/Zr (x:y) ratio of 1:20, whereas selective ethanol to propylene conversion is achieved via a co-precipitated $Zn_xZr_yO_z$ with a Zn/Zr (x:y) ratio of 1:12.

Typically, the formation of isobutylene includes low levels of linear butenes that result from acid catalyzed isomerization. However, for the $Zn_xZr_yO_z$ mixed oxide catalyst prepared via the co-precipitation technique isomerization is surprisingly minimized to the extent that the isobutylene as produced meets high purity isobutylene specifications without further purification. This discovery provides important benefits commercially, as enhancing the concentration of ethanol in the feed stream while maintaining high selectivities and high purity of isobutylene can significantly reduce capital and energy costs.

In some embodiments, the precursor metal salts are added to deionized water to produce an appropriate zinc to zirconium ratio. In additional embodiments, to produce the appropriate ratios for the quaternary mixed oxide catalysts, the zinc and zirconium nitrate mixture may be sonicated to produce a clear solution. In further additional embodiments, the sonicated zinc and zirconium nitrate mixture is added to the flask and precipitated, via dropwise addition of 20 wt % NaOH, LiOH, or KOH, at room temperature, or a slightly elevated temperatures, with vigorous stirring until a final pH of 7.0-9.0 is attained. In an exemplary embodiments, the sonicated zinc and zirconium nitrate mixture is precipitated by attaining a final pH of 7.0-7.5 via dropwise addition of 20 wt % NaOH, LiOH, or KOH at room temperature. Afterwards, the precipitated slurry is allowed to stir at room temperature for an additional 60 minutes. In further additional embodiments, the co-precipitated $Zn_xZr_yA_vQ_sMn_wO_z$ mixed oxide catalyst may be dried at 140° C., and calcinated at a temperature between 400° C. and 550° C. In an exemplary embodiment, calcination occurs at a temperature of 500° C. for a period of 4 hours.

In an exemplary embodiment, the final ratio of Zn/Zr (x:y) in the $Zn_xZr_yO_z$ mixed oxide catalyst is in a range of about 1:8 to about 1:36. In a more specific exemplary embodiment, the ratio of Zn/Zr (x:y) in the $Zn_xZr_yO_z$ mixed oxide catalyst used in the ethanol to high purity isobutylene conversion is about 1:25. In another specific embodiment, the ratio of Zn/Zr (x:y) in the $Zn_xZr_yO_z$ mixed oxide catalyst is about 1:20. In another specific exemplary embodiment, the ratio of Zn/Zr (x:y) in the $Zn_xZr_yO_z$ mixed oxide catalyst used in the ethanol to high purity propylene conversion is about 1:12.

In a further embodiment, the $Zn_xZr_yA_vQ_sMn_wO_z$ mixed oxide catalyst may be co-precipitated with carbon black. In one such embodiment, the $Zn_xZr_yA_vQ_sMn_wO_z$ mixed oxide catalyst co-precipitated with carbon black may be used to prepare high purity propylene by a process disclosed herein.

In another exemplary embodiment, the $Zn_xZr_ySi_vO_z$ mixed oxide catalyst may be prepared via the co-precipitation method with carbon black. In one such embodiment, precursor metal salts are added to deionized water to produce an appropriate zinc to zirconium ratio. In additional embodiments, the zinc and zirconium nitrate mixture may be sonicated to produce a clear solution, or heated to 60 C until a clear solution is produced. In further additional embodiments, the sonicated or heated zinc and zirconium nitrate mixture is added to the flask followed by addition of carbon black. The heterogeneous mixture is stirred for 5-10 minutes to assure complete wetting of carbon black and afterwards the appropriate amount of silicon dioxide is added followed by stirring for an additional 5-10 minutes. The resulting mixture is precipitated, via dropwise addition of 20 wt % NaOH, LiOH, or KOH, at room temperature with vigorous stirring until a final pH of 6.0-8.0 is attained. Afterwards, the precipitated slurry is allowed to stir at room temperature for an additional 60 minutes. In further additional embodiments, the co-precipitated $Zn_xZr_ySi_vO_z$ mixed oxide catalyst may be dried at 140° C., and calcinated at a temperature between 400° C. and 550° C. In an exemplary embodiment, calcination occurs at a temperature of 500° C. for a period of 4 hours. In an exemplary embodiment, the final ratio of Zn/Zr/Si (x:y:v) in the $Zn_xZr_ySi_vO_z$ mixed oxide catalyst is in a range of about 1:8:1 to about 1:36:4. In a more specific exemplary embodiment, the ratio of Zn/Zr/Si (x:y:v) in the $Zn_xZr_ySi_vO_z$ mixed oxide catalyst is about 1:12:2.

In an exemplary embodiment, the $Zn_xZr_yAl_vO_z$ mixed oxide catalyst may be prepared via the co-precipitation method with carbon black. In one such embodiment, precursor metal salts are added to deionized water to produce an appropriate zinc to zirconium ratio. In additional embodiments, the zinc and zirconium nitrate mixture may be sonicated to produce a clear solution, or heated to 60 C until a clear solution is produced. In further additional embodiments, the sonicated or heated zinc and zirconium nitrate mixture is added to the flask followed by addition of finely ground $Al_2O_3$ and carbon black. The heterogeneous mixture is stirred for 5-10 minutes to assure complete wetting of carbon black. The resulting mixture is precipitated, via dropwise addition of 20 wt % NaOH, LiOH, or KOH, at room temperature with vigorous stirring until a final pH of 7.0-8.0 is attained. Afterwards, the precipitated slurry is allowed to stir at room temperature for an additional 60 minutes. In further additional embodiments, the co-precipitated $Zn_xZr_yAl_vO_z$ mixed oxide catalyst may be dried at 140° C., and calcinated at a temperature between 400° C. and 550° C. In an exemplary embodiment, calcination occurs at a temperature of 500° C. for a period of 4 hours. In a specific exemplary embodiment, the ratio of Zn/Zr/Al (x:y:v) in the $Zn_xZr_yAl_vO_z$ mixed oxide catalyst is about 1:12:1.

In an exemplary embodiment, the $Zn_xZr_yAl_vSi_sO_z$ mixed oxide catalyst is prepared using the co-precipitation method with carbon black. In one such embodiment, precursor metal salts are added to deionized water to produce an appropriate zinc to zirconium ratio. In additional embodiments, the zinc and zirconium nitrate mixture may be sonicated to produce a clear solution, or heated to 60 C until a clear solution is produced. In further additional embodiments, the sonicated or heated zinc and zirconium nitrate mixture is added to the flask followed by addition of finely ground $Al_2O_3$, $SiO_2$, and carbon black. The resulting mixture is precipitated, via dropwise addition of 20 wt % NaOH, at room temperature with vigorous stirring until a final pH of 7.0-8.0 is attained. Afterwards, the precipitated slurry is allowed to stir at room temperature for an additional 60 minutes. In further additional embodiments, the co-precipitated $Zn_xZr_yAl_vSi_sO_z$ mixed oxide catalyst may be dried at 140° C., and calcinated at a temperature between 400° C. and 550° C. In an exemplary embodiment, calcination occurs at a temperature of 500° C. for a period of 4 hours. In a specific exemplary embodiment, the ratio of Zn/Zr/Al/Si (x:y:v:s) in the $Zn_xZr_yAl_vSi_sO_z$ mixed oxide catalyst is about 1:12:2:2.

In another exemplary embodiment, the $Zn_xMg_vZr_yO_z$ or $Zn_xCu_vZr_yO_z$ mixed oxide catalyst may be prepared via the co-precipitation method. In one such embodiment, precursor metal salts are added to deionized water to produce an appropriate zinc to zirconium ratio. In additional embodiments, the zinc, magnesium, and zirconium salt mixture may be sonicated to produce a clear solution. In further additional embodiments, the sonicated zinc, magnesium, zirconium salt mixture is added to the flask and precipitated, via dropwise addition of 20 wt % NaOH, LiOH, or KOH, at room temperature with vigorous stirring until a final pH of 7.0-9.0 is attained. Afterwards, the precipitated slurry is allowed to stir at room temperature for an additional 60 minutes. In further additional embodiments, the co-precipitated $Zn_xMg_vZr_yO_z$ or $Zn_xCu_vZr_yO_z$ mixed oxide catalyst, may be dried at 140° C., and calcinated at a temperature between 400° C. and 550° C. In an exemplary embodiment, calcination occurs at a temperature of 500° C. for a period of 4 hours. In an exemplary embodiment, the final ratio of Zn/Mg/Zr or Zn/Cu/Zr (x:v:y) in the $Zn_xMg_vZr_yO_z$ or $Zn_xCu_vZr_yO_z$ mixed oxide catalyst is in a range of about 1:1:12 to about 1:1:36. In a more specific exemplary embodiment, the ratio of Zn/Mg/Zr (x:v:y) or Zn/Cu/Zr (x:v:y) in the $Zn_xMg_vZr_yO_z$ or $Zn_xCu_vZr_yO_z$ mixed oxide catalyst is about 1:1:25.

In some embodiments, levels of co-products (e.g., propylene, phenols, methane, etc.) relative to the functional lower hydrocarbon produced by the disclosed process, (e.g., isobutylene) are reduced relative to $Zn_xZr_yA_vMn_wO_z$ mixed oxide catalysts prepared via the hard template, impregnation, or inverse co-precipitation techniques. Based on acidity characterization measurements, via pyridine thermal desorption technique, the catalyst prepared via co-precipitation technique has a more pronounced bimodal distribution exhibiting lower levels of weaker acid sites with higher levels of stronger acid sites in comparison to the hard-templated, the impregnated, and inverse co-precipitated catalysts. In addition, the unique morphology of the co-precipitated catalyst demands a significantly different $Zn_xZr_yA_vQ_sMn_wO_z$ mixed oxide ratio to afford good ethanol conversion to functionalized lower hydrocarbons.

For example, the formation of isobutylene typically includes low levels of linear butenes that result from acid catalyzed isomerization. However, for the $Zn_xZr_yA_vQ_sMn_wO_z$ mixed oxide catalyst prepared via the co-precipitation technique isomerization is surprisingly minimized to the extent that the functionalized lower hydrocarbon as produced meets high purity specifications, e.g., of isobutylene, propylene, or acetone, without further purification. This discovery provides important benefits commercially, as enhancing the concentration of ethanol in the feed stream while maintaining high selectivities and high purity of isobutylene can significantly reduce capital and energy costs.

Impregnation Method

In some embodiments, the $Zn_xZr_yA_vQ_sMn_wO_z$ mixed oxide catalyst was prepared via an impregnation method. In exemplary embodiments, the impregnated $Zn_xZr_yA_vQ_sMn_wO_z$ mixed oxide catalyst is $Zn_xZr_yMn_wO_z$. In another exemplary embodiment, the impregnated $Zn_xZr_yA_vMn_wO_z$ mixed oxide catalyst is $Zn_xMg_vMn_wZr_yO_z$ or $Zn_xCu_vMn_wZr_yO_z$.

In some embodiments, to prepare impregnated $Zn_xZr_yA_vQ_sMn_wO_z$ mixed oxide catalyst, precursor zinc metal salts are added to deionized water to produce an appropriate zinc to zirconium to manganese ratio. In additional embodiments, the zinc salt may be sonicated to produce a clear solution. In further additional embodiments, the sonicated zinc salt is added to the commercial Zr/Mn catalyst as per incipient wetness technique via dropwise addition. Afterwards, the impregnated $Zn_xZr_yMn_wO_z$ paste may be dried at 140° C., and calcinated at a temperature between 400° C. and 550° C. In an exemplary embodiment, calcination occurs at a temperature of 500° C. for a period of 4 hours. In an exemplary embodiment, the final ratio of Zn/Zr/Mn (x:y:w) in the $Zn_xZr_yMn_wO_z$ mixed oxide catalyst is in a range of about 1:8:1 to about 1:36:1. In a more specific exemplary embodiment, the ratio of Zn/Zr/Mn (x:y:w) in the $Zn_xZr_yMn_wO_z$ mixed oxide catalyst is about 1:8:1.

In some embodiments, to generate the quaternary mixed oxide catalysts, precursor metal salts of zinc and magnesium or zinc and copper, are added to deionized water to produce the appropriate zinc to magnesium to manganese to zirconium ratio, or the appropriate zinc to copper to manganese to zirconium ratio. In additional embodiments, the zinc, magnesium, and/or zinc, copper salt mixture may be sonicated to produce a clear solution. In further additional embodiments, the sonicated zinc, magnesium, or zinc, copper salt mixture is added dropwise to the manganese/zirconium solids via incipient wetness technique, and the resultant solid may be dried at 140° C., and calcined at a temperature between 400° C. and 550° C. In an exemplary embodiment, calcination occurs at a temperature of 500° C. for a period of 4 hours. In an exemplary embodiment, the final ratio of Zn/Mg/Mn/Zr (x:v:w:y) or Zn/Cu/Mn/Zr (x:v:w:y) in the $Zn_xMg_vMn_wZr_yO_z$ or $Zn_xCu_vMn_wZr_yO_z$ mixed oxide catalyst is in a range of about 1:1:4:12 to about 1:5:4:12. In a more specific exemplary embodiment, the ratio of Zn/Mg/Mn/Zr (x:v:w:y) or Zn/Cu/Mn/Zr (x:v:w:y) in the $Zn_xMg_vMn_wZr_yO_z$ or $Zn_xCu_vMn_wZr_yO_z$ mixed oxide catalyst is about 1:1:5:12.

Bifunctional Catalyst

Embodiments of the present application stem from the identification of catalysts and associated processes enabling higher carbon selectivities to functionalized lower hydrocarbons than previously disclosed methods. Accordingly, the catalysts and processes described herein support an industrially relevant process with improved yields of isobutylene and/or propylene from ethanol which lowers the cost of goods in order to directly compete with petro-based products.

The present application describes the use of bifunctional heterogeneous catalysts comprising acid and base functionality for the conversion of ethanol to functionalized lower hydrocarbons. As used herein, "acid functionality" or "acidic functionality" for the catalysts can refer to either Bronsted or Lewis acid acidity. For Bronsted acidity, the catalyst is capable of donating protons (designed as $H^+$) to perform the catalytic reaction, under the conditions present in the catalytic reactor. Acidic ion exchange resins, phosphoric acid present as a liquid phase on a support, are two examples. Metal oxides such as silica, silica-aluminas, promoted zirconia or titania can provide protons $H^+$ associated with Bronsted acidity in the presence of water or water vapor. Lewis acidity entails ability to accept an electron pair, and most typically is obtained via the presence of metal cations in a mixed metal-oxide framework such as silica-alumina or zeolite. Determination of acidic properties can be done via adsorption of a base such as ammonia, use of indictors, or via use of a probe reaction such as dehydration of an alcohol to an olefin, which is acid catalyzed. "Base functionality" or "basic functionality" for the catalysts can refer to either Bronsted or Lewis basicity. For Bronsted basicity, hydroxide anion is supplied by the catalyst, which may be present as an ion exchange resin, or supported liquid phase catalyst, mixed metal oxide with promoter such as alkali, calcium, or magnesium, or in free solution. Lewis base catalysis refers to the conditions where Lewis base catalysis is the process by which an electron pair donor increases the rate of a given chemical reaction by interacting with an acceptor atom in one of the reagents or substrate (see Scott E. Denmark and Gregory L. Beutner, Lewis Base Catalysis in Organic Synthesis, Angew. Chem. Int. Ed. 2008, 47, pp. $1560^{-1}638$). Presence and characterization of basic sites for a heterogeneous catalyst may be determined via sorption of an acidic component, use of probe reactions, or use of indicators, (see K. Tanabe, M. Misono, Y. Ono, H. Hattori (Eds.), New Solid Acids and Bases, Kodansha/Elsevier, Tokyo/Amsterdam, 1989, pp. 260-267). Catalysts such as mixed metal oxides may be "amphoteric", or capable of acting as acidic or basic catalysts depending on process conditions (pH, water concentration), or exhibit both acidic and basic properties under specific operating conditions, as a result of surface structures generated during formulation, or in situ during use to effect catalytic reactions.

As described herein, the reaction converting ethanol to functionalized lower hydrocarbons is performed using a bifunctional catalyst having both acid and base functionality. In one embodiment, the bifunctional catalyst includes at least one of Ca, Fe, Zn, Ce, Sn, K, Ba, Li, Hf, Mn, Sb, Al, Nb, Sc, In, V, Cr, Mo, Ni, Co, Cu, Na, Cs, Rb, B, Mg, Sr, Cd, La, Y, hydrotalcite, zinc-aluminate, phosphate, and combinations thereof. In an exemplary embodiment, the bifunctional catalyst includes at least one of Ca, Fe, Ce, Sn, K, Ba, Li, Hf, Mn, Sb, Al, Nb, Sc, In, V, Cr, Mo, Ni, Co, Cu, and combinations thereof. In another embodiment, the bifunctional catalyst includes at least one oxide from the group of Ti, V, Nb, Ta, Mo, Cr, W, Mn, Re, Al, Ga, Fe, Co, Ir, Ni, Si, Cu, Sn, Cd, P, Pd, Pt, and combinations thereof. The bifunctional catalyst may also include a hydroxyapatite (HAP) combined with any one or more of the above metals.

In some embodiments, the bifunctional catalyst may be self-supporting or adhered to an inert support. In these embodiments, the acidic functionality may be provided by at least one of Zr, Ti, Si, Ce, Co, Sn, Al, and oxides thereof, zeolites, and amorphous silica alumina.

In exemplary embodiments, however, the acidic functionality may be provided by one or more supports. Accordingly, the bifunctional catalyst may comprise a support containing an acidic functionality selected from zirconia, titania, silica, tin, aluminum, cerium, cobalt, oxides, heteropolyacids, alloys and mixtures thereof, as well as zeolites and amorphous silica alumina.

One exemplary support providing the acidic functionality is zirconia. The zirconia may be produced via precipitation of zirconium hydroxide from zirconium salts, through sol-gel processing, or any other method. The zirconia is preferably present in a crystalline form achieved through calcination of the precursor material at temperatures exceeding 400° C. and may include both tetragonal and monoclinic crystalline phases. A promoter may be added to improve the textural or catalytic properties of the zirconia. Such promoters include, without limitation, sulfate, tungstenate, phosphate, titania, silica, and oxides of Group IIIB metals, especially Ce, La, or Y. In one embodiment, the catalyst comprises silica modified zirconia, with Ni, Ru, Cu, Fe, Rh, Re, alloys and combinations thereof.

Another exemplary support providing the acidic functionality is titania. The titania may be produced via precipitation from titanium salts, through sol-gel processing, or any other method. The titania is preferably present in a crystalline form and may include both anatase and rutile crystalline phases. A promoter may be added to improve the textural or catalytic properties of the titania. Such promoters include, without limitation, sulfate, silica, and oxides of Group IIIB metals, especially Ce, La, or Y. In one embodiment, the catalyst system consists of Ru on a primarily rutile phase titania, with the Ru being further alloyed or admixed with Ge, Bi, B, Ni, Sn, Cu, Fe, Re, Rh, Pt, alloys and combinations thereof.

Yet another exemplary support providing the acidic functionality is silica. The silica may be optionally combined with alumina to form a silica-alumina material. In one embodiment, the catalyst system is further alloyed or admixed with Ni, Ru, Cu, Fe, Rh, Re, alloys and combinations thereof. In another embodiment, the catalyst system is Ni on silica-alumina or silica, with the nickel being further alloyed or admixed with Sn, Ge, Bi, Bu, Cu, Re, Ru, Fe, alloys and combinations thereof.

In some embodiments, the catalyst may include zeolites and other microporous supports that contain Group IA compounds, such as Li, Na, K, Cs and Rb. Preferably, the Group IA material is present in an amount less than that required to neutralize the acidic nature of the support. A metal function may also be provided by the addition of group VIIIB metals, or Cu, Ga, In, or Sn.

In one embodiment, the catalyst is derived from the combination of MgO and $Al_2O_3$ to form a hydrotalcite material. Another preferred material contains a combination of MgO and $ZrO_2$, or a combination of ZnO and $Al_2O_3$. Each of these materials may also contain an additional metal function provided by copper or a Group VIIIB metal, such as Ni, Pd, Pt, or combinations of the foregoing.

If a Group IIB, VIIB, VIIB, VIIIB, IIA or IVA metal is included, the loading of the metal is in the range of 0.10 wt % to 30 wt %, with weight percentages of 0.10% and 0.05% increments between, such as 1.00%, 1.10%, 1.15%, 2.00%, 2.50%, 5.00% and 7.50%, 10%, 15%, 20%, 25%, etc. If a second metal is included, the preferred atomic ratio of the second metal is in the range of 0.25-to-1 to 5-to-1, including ratios there between, such as 0.50, 1.00, 2.50 and 5.00-to-1.

In various embodiments above, the catalyst systems include a support suitable for suspending the catalyst in the feedstock solution. The support should be one that provides a stable platform for the chosen catalyst and the reaction conditions. The support may take any form which is stable at the chosen reaction conditions to function at the desired levels, and specifically stable in aqueous feedstock solutions. Such supports include, without limitation, zirconia, titania, silica, cerium, cobalt, heteropolyacids, alloys and mixtures thereof, as well as amorphous silica alumina. Nanoporous supports such as zeolites may also be used.

The support may also be treated or modified to enhance its properties. For example, the support may be treated, as by surface-modification, to modify surface moieties, such as hydrogen and hydroxyl. Surface hydrogen and hydroxyl groups can cause local pH variations that affect catalytic efficiency. The support may also be modified, for example, by treating it with sulfates, phosphates, tungstenates, silanes, lanthanides, alkali compounds or alkali earth compounds. For carbon supports, the carbon may be pretreated with steam, oxygen (from air), inorganic acids or hydrogen peroxide to provide more surface oxygen sites. The preferred pretreatment would be to use either oxygen or hydrogen peroxide. The pretreated carbon may also be modified by the addition of oxides of Group IVB and Group VB. It is preferred to use oxides of Ti, V, Zr and mixtures thereof.

The catalyst systems, whether alone or mixed together, may be prepared using conventional methods known to those in the art. Such methods include incipient wetting, evaporative impregnation, chemical vapor deposition, washcoating, magnetron sputtering techniques, and the like. The method chosen to fabricate the catalyst is not particularly critical to the function of the invention, with the proviso that different catalysts will yield different results, depending upon considerations such as overall surface area, porosity, etc.

In some embodiments, the ratio of the basic component (e.g., Ca, Fe, Ce, Sn, K, Ba, Li, Hf, Mn, Sb, Al, Nb, Sc, In, V, Cr, Mo, Ni, Co, Cu, etc.) to the acidic component (e.g., Zr, Si, Ti, etc.) in the bifunctional catalyst is in a range of about 100:1 to about 1:100. In a more specific embodiment, the ratio of the basic component to the acidic component in the bifunctional catalyst is in a range of about 10:1 to about 1:50. In a further embodiment, the ratio of the basic component to the acidic component in the bifunctional catalyst is in a range of about 1:1 to about 1:25. In another embodiment, the ratio of the basic component to the acidic component in the bifunctional catalyst is in a range of about 1:5 to about 1:20.

Catalytic Promoters

In some embodiments, at least one promoter may be used to affect the reaction, for example, by increasing activity and catalyst lifetime of a $Zn_xZr_yA_vQ_sMn_wO_z$ mixed oxide or bifunctional heterogeneous catalyst. Without limitation, promoters such as tin, copper, rhenium, ruthenium, gold, silver, manganese, magnesium, scandium, nickel, and combinations thereof may be used to enhance catalyst performance.

In an exemplary embodiment, promoters which can be used to enhance catalyst performance of the hard-templated $Zn_xZr_yO_z$ mixed oxide catalyst in the ethanol to isobutylene include, without limitation, tin, copper, rhenium, ruthenium, gold, silver and combinations thereof.

In an exemplary embodiment, promoters which may be used to enhance catalyst performance of the co-precipitated $Zn_xZr_yO_z$ mixed oxide catalyst, with the ratio of Zn/Zr (x:y) of about 1:25, in the ethanol to isobutylene conversion include, without limitation, promoters such as manganese, magnesium, nickel, and combinations thereof.

In an exemplary embodiment, promoters which may be used to enhance catalyst performance of the co-precipitated $Zn_xZr_yO_z$ mixed oxide catalyst, with the ratio of Zn/Zr (x:y) of about 1:12, in the ethanol to propylene conversion include, without limitation, promoters such as manganese, scandium, nickel, and combinations.

In an exemplary embodiment promotes may be used to enhance catalytic performance with impregnated $Zn_xZr_yMn_wO_z$ mixed oxide catalyst, with the ratio of Zn/Zr/Mn (x:y:w) of about 1:8:1, in the ethanol to isobutylene include, without limitation, magnesium, nickel, and combinations thereof.

In an exemplary embodiment, promoters which can be used to enhance catalyst performance with the co-precipitated $Zn_xZr_ySi_vO_z$ mixed oxide catalyst ratio of Zn/Zr/Si (x:y:v) of about 1:12:2 in the ethanol to propylene conversion include, without limitation, manganese, scandium, nickel, and combinations thereof.

In an exemplary embodiment, promoters which can be used to enhance catalyst performance with the co-precipitated $Zn_xZr_yAl_vO_z$ mixed oxide catalyst with the ratio of Zn/Zr/Al (x:y:v) of about 1:12:1 in the ethanol to propylene conversion include, without limitation, manganese, scandium, hafnium, lanthanum, titanium, silicon and combinations thereof.

In an exemplary embodiments, promoters which can be used to enhance catalyst performance with the co-precipitated $Zn_xZr_yAl_vSi_sO_z$ mixed oxide catalyst with the ratio of Zn/Zr/Al/Si (x:y:v:s) of about 1:12:2:2 in the ethanol to propylene conversion include, without limitation, tin, copper, rhenium, ruthenium, gold, silver, manganese, magnesium, scandium, nickel, and combinations thereof.

Ethanol to Isobutylene Conversion

As noted above, in one aspect, the present application is directed to a process for preparing isobutylene, comprising: (a) feeding to a reactor a reactor feed comprising ethanol at a molar concentration of at least about 14 mol %; and (b) contacting the ethanol with a $Zn_xZr_yO_z$ mixed oxide catalyst in the reactor, whereby ethanol is converted to isobutylene at a yield of at least about 30% of the maximum theoretical molar yield. A reaction scheme by which the inventive process converts ethanol into isobutylene and co-products such as propylene, phenol, meta-cresol, 3,5-xylenol, acetone, and hydrogen is illustrated in FIG. 1. In certain embodiments, the process may further comprise step (c) of recovering the isobutylene.

In one embodiment, ethanol is converted to isobutylene at a yield of at least about 30% of the maximum theoretical molar yield. In another embodiment, ethanol is converted to isobutylene at a yield of at least about 35% of the maximum theoretical molar yield. In yet another embodiment, ethanol is converted to isobutylene at a yield of at least about 40% of the maximum theoretical molar yield. In yet another embodiment, ethanol is converted to isobutylene at a yield of at least about 45%, 50%, 55%, or 60% of the maximum theoretical molar yield. In an exemplary embodiment, ethanol is converted to isobutylene at a yield of at least about 65% of the maximum theoretical molar yield. In another exemplary embodiment, ethanol is converted to isobutylene at a yield of at least about 70% of the maximum theoretical molar yield. In yet another exemplary embodiment, ethanol is converted to isobutylene at a yield of at least about 75% of the maximum theoretical molar yield.

In one embodiment of the present disclosure, the process for preparing isobutylene involves $Zn_xZr_yO_z$ mixed oxide catalyst prepared via the hard-templated method wherein the ratio of Zn/Zr (x:y) in the hard-templated $Zn_xZr_yO_z$ mixed oxide catalyst is in a range of about 1:1 to about 1:100. In an exemplary embodiment, the final ratio of Zn/Zr (x:y) in the hard-templated $Zn_xZr_yO_z$ mixed oxide catalyst is in a range of about 1:8 to about 1:20. In a more specific exemplary embodiment, the ratio of Zn/Zr (x:y) in the hard-templated $Zn_xZr_yO_z$ mixed oxide catalyst is about 1:12.

In an exemplary embodiment, ethanol is converted to isobutylene by the process via a hard-templated $Zn_xZr_yO_z$ mixed oxide catalyst at a yield of at least about 30% of the maximum theoretical molar yield. In one such exemplary embodiment, ethanol is converted to isobutylene at a yield of at least 45% of the maximum theoretical molar yield. In one embodiment, the isobutylene produced by the process is at least about 96% pure. In one embodiment, the functionalized lower hydrocarbons produced by the process include isobutylene, propylene, and acetone. For example, in one embodiment, the molar concentration of the ethanol in the reactor feed is at least 14.8%, the functionalized lower hydrocarbons produced by the process include isobutylene, propylene, and acetone. In such an exemplary embodiment, the isobutylene is produced at a yield of about 45% of the maximum theoretical molar yield, the propylene is produced at a yield of about 8% of the maximum theoretical molar yield, and the acetone is produced at a yield of about 14% of the maximum theoretical molar yield. In another exemplary embodiment, the molar concentration of the ethanol in the reactor feed is at least 25.3% or greater. In such an exemplary embodiment, the functionalized lower hydrocarbons produced by the process include isobutylene, propylene, and acetone. In a further exemplary embodiment, the isobutylene is produced at a yield of about 46% of the maximum theoretical molar yield, the propylene is produced at a yield of about 14% of the maximum theoretical molar yield, and the acetone is produced at a yield of about 3% of the maximum theoretical molar yield.

In some embodiments, at least one promoter may be used to affect the reaction, for example, by increasing activity and catalyst lifetime of the $Zn_xZr_yO_z$ mixed oxide catalyst prepared using the hard-templated method to convert ethanol to isobutylene. Without limitation, promoters such as tin, copper, rhenium, ruthenium, gold, silver and combinations thereof may be used to enhance catalyst performance.

Ethanol to High Purity Isobutylene Conversion

As noted above, in one aspect, the present application is directed to a process for preparing high purity isobutylene, comprising: (a) feeding to a reactor a reactor feed comprising ethanol at a molar concentration of at least about 14 mol %; and (b) contacting the ethanol with a co-precipitated $Zn_xZr_yO_z$ mixed oxide catalyst in the reactor, whereby ethanol is converted to isobutylene at a yield of at least about 30% of the maximum theoretical molar yield, and isobutylene purity of at least about 99.7%. In certain embodiments, the process may further comprise step (c) of recovering the isobutylene.

In one embodiment of the present disclosure, the process for preparing high purity isobutylene involves $Zn_xZr_yO_z$ mixed oxide catalyst prepared via the co-precipitated method wherein the ratio of Zn/Zr (x:y) in the co-precipitated $Zn_xZr_yO_z$ mixed oxide catalyst is in a range of about 1:1 to about 1:100. In a more specific embodiment, the ratio of Zn/Zr (x:y) in the co-precipitated $Zn_xZr_yO_z$ mixed oxide catalyst to prepare high purity isobutylene is in a range of about 1:2 to about 1:50. In a further embodiment, the ratio of Zn/Zr (x:y) in the co-precipitated $Zn_xZr_yO_z$ mixed oxide catalyst to prepare high purity isobutylene is in a range of about 1:5 to about 1:25. In another embodiment, the ratio of Zn/Zr (x:y) in the co-precipitated $Zn_xZr_yO_z$ mixed oxide catalyst to prepare high purity isobutylene is in a range of about 1:8 to about 1:25. In one exemplary embodiment, the ratio of Zn/Zr (x:y) in the co-precipitated $Zn_xZr_yO_z$ mixed oxide catalyst to prepare high purity isobutylene is about 1:25. In some embodiments, the co-precipitated $Zn_xZr_yO_z$ mixed oxide catalyst improves carbon selectivity of the process and increases purity of the isobutylene produced by the process.

In one embodiment, ethanol is converted via a co-precipitated $Zn_xZr_yO_z$ mixed oxide catalyst to high purity isobutylene at a yield of at least about 35% of the maximum theoretical molar yield. In another embodiment, ethanol is converted via a co-precipitated $Zn_xZr_yO_z$ mixed oxide catalyst to high purity isobutylene at a yield of at least about 40% of the maximum theoretical molar yield. In yet another embodiment, ethanol is converted via a co-precipitated $Zn_xZr_yO_z$ mixed oxide catalyst to high purity isobutylene at a yield of at least about 45%, 50%, 55%, or 60% of the maximum theoretical molar yield. In an exemplary embodiment, ethanol is converted via a co-precipitated $Zn_xZr_yO_z$ mixed oxide catalyst to high purity isobutylene at a yield of at least about 65% of the maximum theoretical molar yield. In another exemplary embodiment, ethanol is converted via a co-precipitated $Zn_xZr_yO_z$ mixed oxide catalyst to high purity isobutylene at a yield of at least about 70% of the maximum theoretical molar yield. In yet another exemplary embodiment, ethanol is converted via a co-precipitated $Zn_xZr_yO_z$ mixed oxide catalyst to high purity isobutylene at a yield of at least about 75% of the maximum theoretical molar yield.

In some embodiments, high purity isobutylene is prepared according to the process described herein. Specifically, the process disclosed herein is capable of producing substantially pure isobutylene containing no or relatively small amounts of linear butenes such as n-butene and 2-butene, or higher oligomer by-products. In one embodiment, the isobutylene produced by the process disclosed herein is at least about 96% pure. In another embodiment, the isobutylene produced by the process disclosed herein is at least about 97% pure. In yet another embodiment, the isobutylene produced by the process disclosed herein is at least about 98% pure. In yet another embodiment, the isobutylene produced by the process disclosed herein is at least about 99% pure. In yet another embodiment, the isobutylene produced by the process disclosed herein is at least about 99.5% pure. In yet another embodiment, the isobutylene produced by the process disclosed herein is at least about 99.7% pure. In yet another embodiment, the isobutylene produced by the process disclosed herein is at least about 99.9% pure.

In an exemplary embodiment, isobutylene is produced by the process via a co-precipitated $Zn_xZr_yO_z$ mixed oxide catalyst at a yield of at least about 30% is isobutylene. In one such embodiment, ethanol is converted to isobutylene at a yield of at least 50% of the maximum theoretical molar yield. In a further embodiment, the isobutylene is at least 99.7% pure. In another exemplary embodiment, the molar concentration of the ethanol in the reactor feed is at least 25% or greater. In such an exemplary embodiment, the functionalized lower hydrocarbons produced by the process include isobutylene, propylene, and acetone. In still another embodiment, the isobutylene is produced at a yield of about 50% of the maximum theoretical molar yield, the propylene is produced at a yield of about 10% of the maximum theoretical molar yield, and the acetone is produced at yield of about 2% of the maximum theoretical value.

In some embodiment, promoters may be used to enhance catalyst performance of the co-precipitated $Zn_xZr_yO_z$ mixed oxide catalyst, with the ratio of Zn/Zr (x:y) of about 1:25, in the ethanol to isobutylene conversion. Non-limiting examples of promoters which may be used to enhance catalytic performance include manganese, magnesium, nickel, and combinations thereof.

Ethanol to High Yield Isobutylene

As noted above, in another aspect, the present application is directed to a process for preparing high yield and selectivity isobutylene, comprising: (a) feeding to a reactor a reactor feed comprising ethanol at a molar concentration of at least about 14 mol % and (b) contacting the ethanol with an impregnated $Zn_xZr_yMn_wO_z$ mixed oxide catalyst in the reactor, whereby ethanol is converted to isobutylene at a yield of at least about 30% of the maximum theoretical molar yield. In some embodiments, the isobutylene has a purity of at least about 98%. In some embodiments, the impregnated $Zn_xZr_yMn_wO_z$ mixed oxide catalyst improves carbon selectivity of the process and increases purity of the isobutylene produced by the process relative to a $Zn_xZr_yMn_wO_z$ mixed oxide catalyst prepared by using the hard-template method or the co-precipitation method. In certain embodiments, the process may further comprise step (c) of recovering the isobutylene.

In one embodiment of the present disclosure, the process for preparing high yield isobutylene involves $Zn_xZr_yMn_wO_z$ mixed oxide catalyst prepared via the impregnated method wherein the ratio of Zn/Zr (x:y) in the impregnated $Zn_xZr_yO_z$ mixed oxide catalyst is in a range of about 1:1:1 to about 1:100:30. In a more specific embodiment, the ratio of Zn/Zr/Mn (x:y:w) in the impregnated $Zn_xZr_yMn_wO_z$ mixed oxide catalyst to prepare high yield isobutylene is in a range of about 1:2:30 to about 1:50:30. In a further embodiment, the ratio of Zn/Zr/Mn (x:y:w) in the impregnated $Zn_xZr_yMn_wO_z$ mixed oxide catalyst to prepare high yield isobutylene is in a range of about 1:5:1 to about 1:25:30. In another embodiment, the ratio of Zn/Zr/Mn (x:y:w) in the impregnated $Zn_xZr_yMn_wO_z$ mixed oxide catalyst to prepare high yield isobutylene is in a range of about 1:8:1 to about 1:20:30. In one exemplary embodiment, the ratio of Zn/Zr/Mn (x:y:w) in the impregnated $Zn_xZr_yMn_wO_z$ mixed oxide catalyst to prepare high yield isobutylene is about 1:8:1.

In one embodiment, ethanol is converted via the impregnated $Zn_xZr_yMn_wO_z$ mixed oxide catalyst to isobutylene at a yield of at least about 35% of the maximum theoretical molar yield. In another embodiment, ethanol is converted via the impregnated $Zn_xZr_yMn_wO_z$ mixed oxide catalyst to high yield and selectivity to isobutylene at a yield of at least about 40% of the maximum theoretical molar yield. In yet another embodiment, ethanol is converted via the impregnated $Zn_xZr_yMn_wO_z$ mixed oxide catalyst to isobutylene at a yield of at least about 45%, 50%, 55%, or 60% of the maximum theoretical molar yield. In an exemplary embodiment, ethanol is converted via the impregnated $Zn_xZr_yMn_wO_z$ mixed oxide catalyst to isobutylene at a yield of at least about 65% of the maximum theoretical molar yield. In another exemplary embodiment, ethanol is converted via the impregnated $Zn_xZr_yMn_wO_z$ mixed oxide catalyst to isobutylene at a yield of at least about 70% of the maximum theoretical molar yield. In yet another exemplary embodiment, ethanol is converted via the impregnated $Zn_xZr_yMn_wO_z$ mixed oxide catalyst to isobutylene at a yield of at least about 75% of the maximum theoretical molar yield.

In an exemplary embodiment, isobutylene is produced via impregnated $Zn_xZr_yMn_wO_z$ mixed oxide catalyst at a yield of at least about 30% of the maximum theoretical molar yield. In one such embodiment, the yield of the isobutylene at least about 50% of the maximum theoretical molar yield. In a further embodiment, the isobutylene is at least 99.7% pure. In another exemplary embodiment, In one such exemplary embodiment, the molar concentration of the ethanol in the reactor feed is at least 25% or greater. In one such embodiment, the functionalized lower hydrocarbon includes isobutylene, propylene, and acetone. In one such embodiment, wherein the isobutylene is produced at a yield of about 50% of the maximum theoretical molar yield, the propylene is produced at a yield of about 10% of the maximum theoretical molar yield, and the acetone is produced at a yield of about 2% of the maximum theoretical molar yield.

In some embodiments, at least one promoter may be used to affect the reaction, for example, by increasing activity and catalyst lifetime of the impregnated $Zn_xZr_yO_z$ mixed oxide catalyst. Without limitation, promoters such as magnesium, nickel, and combinations thereof may be used to enhance catalyst performance.

Ethanol to High Purity Propylene Conversion

As noted above, in one aspect, the present application is directed to a process for preparing high purity propylene, comprising: (a) feeding to a reactor a reactor feed comprising ethanol at a molar concentration of at least about 14 mol %; and (b) contacting the ethanol with a co-precipitated $Zn_xZr_yA_vQ_sMn_wO_z$ mixed oxide catalyst in the reactor, whereby ethanol is converted to propylene at a yield of at least about 30%. In one embodiment, the propylene has a purity of at least about 98%. In exemplary embodiments, the co-precipitated $Zn_xZr_yA_vQ_sMn_wO_z$ mixed oxide used in the conversion of ethanol to high purity propylene is $Zn_xZr_yO_z$, $Zn_xZr_ySi_vO_z$, or $Zn_xZr_yAl_vO_z$, or $Zn_xZr_yAl_vSi_sO_z$. In certain embodiments, the process may further comprise step (c) of recovering the polypropylene.

In one embodiment of the present disclosure, the process for preparing high purity propylene involves $Zn_xZr_yO_z$ mixed oxide catalyst prepared via the co-precipitated method wherein the ratio of Zn/Zr (x:y) in the $Zn_xZr_yO_z$ mixed oxide catalyst is in a range of about 1:8 to about 1:36. In a more specific exemplary embodiment, the ratio of Zn/Zr (x:y) in the co-precipitated $Zn_xZr_yO_z$ mixed oxide catalyst to prepare high purity propylene is about 1:12. In some embodiments, the co-precipitated $Zn_xZr_yO_z$ mixed oxide catalyst improves carbon selectivity of the process and increases purity of the propylene produced by the process.

In an exemplary embodiment, propylene is produced by the process via a co-precipitated $Zn_xZr_yO_z$ mixed oxide catalyst at a yield of at least about 30% of the maximum theoretical molar yield. In one such embodiment, ethanol is converted to propylene at a yield of at least 60% of the maximum theoretical molar yield. In a further embodiment, the isobutylene produced by the process is at least 99.5% pure. In one another exemplary embodiment, the molar concentration of the ethanol in the reactor feed is about 25% or greater. In another exemplary embodiment, the functionalized lower hydrocarbon includes isobutylene, propylene, and acetone. In one such embodiment, wherein the isobutylene is produced at a yield of about 5% of the maximum theoretical molar yield, the propylene is produced at a yield of about 63% of the maximum theoretical molar yield, and the acetone is produced at a yield of about 1% of the maximum theoretical molar yield.

In some embodiments, at least one promoter may be used to affect the reaction, for example, by increasing activity and catalyst lifetime of the co-precipitated $Zn_xZr_yO_z$ mixed oxide catalyst, with a ratio of Zn/Zr (x:y) of about 1:12, in the conversion of ethanol to propylene. Without limitation, promoters such as manganese, scandium, nickel, and combinations thereof may be used to enhance catalyst performance.

In one embodiment of the present disclosure, the process for preparing high purity propylene involves $Zn_xZr_ySi_vO_z$ mixed oxide catalyst wherein the ratio of Zn/Zr/Si (x:y:v) in the co-precipitated $Zn_xZr_ySi_vO_z$ mixed oxide catalyst is in a range of about 1:1:1 to about 1:100:100. In a more specific embodiment, the ratio of Zn/Zr/Si (x:y:w) in the co-precipitated $Zn_xZr_ySi_vO_z$ mixed oxide catalyst to prepare high purity propylene is in a range of about 1:2:2 to about 1:50:50. In a further embodiment, the ratio of Zn/Zr/Si (x:y:v) in the co-precipitated $Zn_xZr_ySi_vO_z$ mixed oxide catalyst to prepare high purity propylene is in a range of about 1:5:5 to about 1:25:25. In another embodiment, the ratio of Zn/Zr/Si (x:y:v) in the co-precipitated $Zn_xZr_ySi_vO_z$ mixed oxide catalyst to prepare high purity propylene is in a range of about 1:8:8 to about 1:25:25. In one exemplary embodiment, the ratio of Zn/Zr/Si (x:y:v) in the co-precipitated $Zn_xZr_ySi_vO_z$ mixed oxide catalyst to prepare high purity propylene is about 1:12:2. In some embodiments, the co-precipitated $Zn_xZr_ySi_vO_z$ mixed oxide catalyst improves carbon selectivity of the process and increases purity of the isobutylene produced by the process.

In some embodiments, at least one promoter may be used to affect the reaction, for example, by increasing activity and catalyst lifetime of the co-precipitated $Zn_xZr_ySi_vO_z$ mixed oxide catalyst to prepare high purity propylene. Without limitation, promoters such as manganese, scandium, nickel, and combinations thereof may be used to enhance catalyst performance.

In one embodiment of the present disclosure, the process for preparing high purity propylene involves co-precipitated $Zn_xZr_yAl_vO_z$ mixed oxide catalyst wherein the ratio of Zn/Zr/Al (x:y:v) is in a range of about 1:1:1 to about 1:100:100, about 1:2:2 to about 1:50:50, about 1:5:5 to about 1:25:25, or about 1:8:8 to about 1:20:20. In some embodiments, the process for preparing high purity propylene involves co-precipitated $Zn_xZr_yAl_vO_z$ mixed oxide catalyst to prepare high purity propylene wherein the ratio of Zn/Zr/Al (x:y:v) is about 1:12:1. In some embodiments, the co-precipitated $Zn_xZr_yAl_vO_z$ mixed oxide catalyst improves carbon selectivity of the process and increases purity of the isobutylene produced by the process.

In some embodiments, at least one promoter may be used to affect the reaction, for example, by increasing activity and catalyst lifetime of the co-precipitated $Zn_xZr_yAl_vO_z$ mixed oxide catalyst, with a ratio of Zn/Zr/Al (x:y:v) of about 1:12:1, to prepare high purity propylene. Without limitation, promoters such as manganese, scandium, hafnium, lanthanum, titanium, silicon and combinations thereof may be used to enhance catalyst performance.

In one embodiment, ethanol is converted via a co-precipitated $Zn_xZr_ySi_vO_z$ or $Zn_xZr_yAl_vO_z$ mixed oxide catalyst to high purity propylene at a yield of at least about 35%. In another embodiment, ethanol is converted a co-precipitated $Zn_xZr_ySi_vO_z$ or $Zn_xZr_yAl_vO_z$ mixed oxide catalyst to high purity propylene at a yield of at least about 40%. In yet another embodiment, ethanol is converted a co-precipitated $Zn_xZr_ySi_vO_z$ or $Zn_xZr_yAl_vO_z$ mixed oxide catalyst to high purity propylene at a yield of at least about 45%, 50%, 55%, or 60%. In an exemplary embodiment, ethanol is converted a co-precipitated $Zn_xZr_ySi_vO_z$ or $Zn_xZr_yAl_vO_z$ mixed oxide catalyst to high purity propylene at a yield of at least about 65%. In another exemplary embodiment, ethanol is converted a co-precipitated $Zn_xZr_ySi_vO_z$ or $Zn_xZr_yAl_wO_z$ mixed oxide catalyst to high purity propylene at a yield of at least about 70%. In yet another exemplary embodiment, ethanol is converted a co-precipitated $Zn_xZr_ySi_vO_z$ or $Zn_xZr_yAl_vO_z$ mixed oxide catalyst to high purity propylene at a yield of at least about 75%.

In an exemplary embodiment, isobutylene is produced by the process via a co-precipitated $Zn_xZr_ySi_vO_z$ or $Zn_xZr_yAl_vO_z$ mixed oxide catalyst at a yield of at least about 30% of the maximum theoretical molar yield. In one such embodiment, ethanol is converted to isobutylene via a co-precipitated $Zn_xZr_ySi_vO_z$ mixed oxide catalyst at a yield of at least 60% of the maximum theoretical molar yield. In a further embodiment the isobutylene is at least 99.7% pure. In another exemplary embodiment, the molar concentration of the ethanol in the reaction feed is about 25% or greater. In such an embodiment, the functionalized lower hydrocarbon includes isobutylene, propylene, and acetone. In a further embodiment, the isobutylene is produced at a yield of about 8% of the maximum theoretical molar yield, the propylene is produced at a yield of about 60% of the maximum theoretical molar yield, and the acetone is produced at a yield of about 0.1% of the maximum theoretical molar yield.

In another exemplary embodiment, ethanol is converted to isobutylene via a co-precipitated $Zn_xZr_yAl_vO_z$ mixed oxide catalyst at a yield of at least 59% of the maximum theoretical molar yield. In one such embodiment, the isobutylene is at least 99.7% pure. In another exemplary embodiment, the molar concentration of the ethanol in the reaction feed is about 33% or greater. In one such exemplary embodiment, the functionalized lower hydrocarbon includes isobutylene, propylene, and acetone. In another embodiment, the isobutylene is produced at a yield of about 9% of the maximum theoretical molar yield, the propylene is produced at a yield of about 59% of the maximum theoretical molar yield, and the acetone is produced at a yield of about 0.7% of the maximum theoretical molar yield.

In some embodiments, high purity propylene is prepared according to the process described herein. Specifically, the process disclosed herein is capable of producing substantially pure propylene containing no or relatively small amounts of propane. In one embodiment, the propylene is at least about 96% pure. In another embodiment, the propylene is at least about 97% pure. In yet another embodiment, the propylene is at least about 98% pure. In yet another embodiment, the propylene is at least about 99% pure. In yet another embodiment, the propylene is at least about 99.5% pure. In yet another embodiment, the propylene is at least about 99.9% pure.

Ethanol to High Selectivity to Propylene

As noted above, in one aspect, the present application is directed to a process for preparing high purity propylene, comprising: (a) feeding to a reactor a reactor feed comprising ethanol at a molar concentration of at least about 14 mol %; and (b) contacting the ethanol with a co-precipitated $Zn_xZr_yAl_vSi_sO_z$ mixed oxide catalyst in the reactor, whereby ethanol is converted to propylene at a yield of at least about 30%. In one embodiment, the propylene has a yield of about 75% of the maximum theoretical molar yield. In certain embodiments, the process may further comprise step (c) of recovering the polypropylene.

In some embodiments, A is Al, and V is greater than or equal to 1, Q is Si and S is greater than or equal to about 1, and W is 0. In one such embodiment, the ratio of the Zn/Zr/Al/Si (x:y:v:s) in the co-precipitated $Zn_xZr_yAl_bSi_sO_z$ mixed oxide catalyst is from about 1:1:1:1 to about 1:100:100:100, from about 1:2:2:2 to about 1:50:50:50, from about 1:5:5:5 to about 1:25:25:25, or from about 1:8:8:8 to about 1:20:20:20. In an exemplary embodiment, the ratio of Zn/Zr/Al/Si (x:y:v:s) in the co-precipitated $Zn_xZr_yAl_vSi_sO_z$ mixed oxide catalyst is about 1:12:2:2.

In some embodiments, the yield of the propylene is at least about 30%, at least about 40%, at least about 50%, at least about 60%, or at least about 70%, of the maximum theoretical yield. In one such embodiment, the yield of the isobutylene is about 75.5% of the maximum theoretical yield.

The one exemplary embodiment, the molar concentration of the ethanol in the reactor feed is about 37% or greater. In one such embodiment, the functionalized lower hydrocarbon includes isobutylene, propylene, and acetone. In a further exemplary embodiment, the isobutylene is produced at a yield of about 27% of the maximum theoretical molar yield, the propylene is produced at a yield of about 75.5% of the maximum theoretical molar yield, and the acetone is produced at a yield of about 0.01% of the maximum theoretical molar yield.

Ethanol to Acetone Conversion

As discussed above, in one aspect, the application relates to a process for preparing acetone, comprising: (a) feeding to a reactor a reactor feed comprising ethanol at a molar concentration of at least about 14 mol %; and (b) contacting the ethanol with a, $Zn_xMg_vZr_yO_z$ or $Zn_xCu_vZr_yO_z$ mixed oxide catalyst prepared via a co-precipitation method, or $Zn_xMg_vMn_wZr_yO_z$ or $Zn_xCu_vMn_wZr_yO_z$ mixed oxide catalyst prepared via an impregnation technique in the reactor, whereby ethanol is converted to acetone in yield of at least about 30% of the maximum theoretical molar yield. In certain embodiments, the process may further comprise step (c) of recovering the acetone. In some embodiments, the co-precipitated $Zn_xMg_vZr_yO_z$ or $Zn_xCu_vZr_yO_z$ mixed oxide catalyst improves carbon selectivity of the process. In certain embodiments, the process may further comprise step (c) of recovering the acetone. In some embodiments, the co-precipitated $Zn_xMg_vZr_yO_z$ or $Zn_xCu_vZr_yO_z$ mixed oxide catalyst or the impregnated $Zn_xMg_vMn_wZr_yO_z$ or $Zn_xCu_vMn_wZr_yO_z$ mixed oxide catalyst improves purity of the process.

In one embodiment, ethanol is converted to acetone at a yield of at least about 35% of the maximum theoretical molar yield. In another embodiment, ethanol is converted to acetone at a yield of at least about 40% of the maximum theoretical molar yield. In yet another embodiment, ethanol is converted to acetone at a yield of at least about 45%, 50%, 55%, or 60% of the maximum theoretical molar yield. In an exemplary embodiment, ethanol is converted to acetone at a yield of at least about 65% of the maximum theoretical molar yield. In another exemplary embodiment, ethanol is converted to acetone at yield of at least about 70% of the maximum theoretical molar yield. In yet another exemplary embodiment, ethanol is converted to acetone at a yield of at least about 75% of the maximum theoretical molar yield.

In some embodiments, A is Mg or Cu, V is greater than or equal to about 1, W is 0, and S is 0. Accordingly, in one embodiment of the present disclosure, the process for preparing acetone with improved carbon selectivity involves $Zn_xMg_vZr_yO_z$ or $Zn_xCu_vZr_yO_z$ prepared via the co-precipitated method, wherein the ratio of Zn/Mg/Zr or Zn/Cu/Zr (x:v:y) in the co-precipitated $Zn_xMg_vZr_yO_z$ or $Zn_xCu_vZr_yO_z$ mixed oxide catalyst is in a range of about 1:1:1 to about 1:1:100. In a more specific embodiment, the ratio of Zn/Mg/Zr or Zn/Cu/Zr (x:v:y) in the co-precipitated $Zn_xMg_vZr_yO_z$ or $Zn_xCu_vZr_yO_z$ mixed oxide catalyst to prepare acetone is in a range of about 1:1:2 to about 1:1:50. In a further embodiment, the ratio of Zn/Mg/Zr or Zn/Cu/Zr (x:v:y) in the co-precipitated $Zn_xMg_vZr_yO_z$ or $Zn_xCu_vZr_yO_z$ mixed oxide catalyst to prepare acetone is in a range of about 1:1:5 to about 1:1:36. In another embodiment, the ratio of Zn/Mg/Zr or Zn/Cu/Zr (x:v:y) in the co-precipitated $Zn_xMg_vZr_yO_z$ or $Zn_xCu_vZr_yO_z$ mixed oxide catalyst to prepare acetone is in a range of about 1:1:12 to about 1:1:25. In one exemplary embodiment, the ratio of Zn/Mg/Zr or Zn/Cu/Zr (x:v:y) in the co-precipitated $Zn_xMg_vZr_yO_z$ or $Zn_xCu_vZr_yO_z$ mixed oxide catalyst to prepare acetone is about 1:1:25.

In an exemplary embodiment, acetone is produced by the process via a co-precipitated $Zn_xMg_vZr_yO_z$ or $Zn_xCu_vZr_yO_z$ mixed oxide catalyst at a yield of at least about 30% of the maximum theoretical molar yield. In one such embodiment, the yield of the ethanol is at least 54% of the maximum theoretical molar yield. In a further embodiment, the acetone is at least 96% pure. In another exemplary embodiment, the molar concentration of the ethanol in the reactor feed is about 25% or greater. In another exemplary embodiment, the functionalized lower hydrocarbon includes isobutylene, propylene, and acetone. In such an embodiment, the isobutylene is produced at a yield of about 8% of the maximum theoretical molar yield, the propylene is produced at a yield of about 2% of the maximum theoretical molar yield, and the acetone is produced at a yield of about 54% of the maximum theoretical molar yield.

In some embodiments, A is Mg or Cu, V is greater than or equal to 1, W is greater than or equal to about 1, and S is 0. In one embodiment of the present disclosure, the process for preparing acetone with improved carbon selectivity involves $Zn_xMg_vMn_wZr_yO_z$ or $Zn_xCu_vMn_w Zr_yO_z$ mixed oxide catalyst prepared via the impregnated method, wherein the ratio of Zn/Mg/Mn/Zr (x:v:w:y) or Zn/Cu/Mn/

Zr (x:v:w:y) is in a range of about 1:1:1:1 to about 1:1:10:100, about 1:2:2:2 to about 1:10:10:50, about 1:1:1:5 to about 1:10:10:25, or about 1:2:2:8 to about 1:15:15:20. In some embodiments, the process for preparing acetone with improved carbon selectivity involves $Zn_xMg_yMn_wZr_yO_z$ or $Zn_xCu_yMn_wZr_yO_z$ mixed oxide catalyst wherein the ratio of Zn/Mg/Mn/Zr (x:v:w:y) or Zn/Cu/Mn/Zr (x:v:w:y) is about 1:1:5:15.

In an exemplary embodiment, acetone is produced by the process via an impregnated $Zn_xMg_yMn_wZr_yO_z$ or $Zn_xCu_yMn_wZr_yO_z$ mixed oxide catalyst at a yield of at least about 30% of the maximum theoretical molar yield. In one such embodiment, ethanol is converted to acetone at a yield of at least 60% of the maximum theoretical molar yield. In one embodiment, the acetone is at least 96% pure. In another exemplary embodiment, the molar concentration of the ethanol in the reactor feed is at least 33% or greater. In one such embodiment, the functionalized lower hydrocarbon includes isobutylene, propylene, and acetone. In one such embodiment, the isobutylene is produced at a yield of about 10% of the maximum theoretical molar yield, the propylene is produced at a yield of about 1% of the maximum theoretical molar yield, and the acetone is produced at a yield of about 62%, of the maximum theoretical molar yield.

Recovery of Functionalized Lower Hydrocarbons

In certain embodiments, the process of the present application may further comprise step (c) of recovering the functionalized lower hydrocarbon. In exemplary embodiments, the functionalized lower hydrocarbon recovered is selected from isobutylene, propylene, and acetone, and combinations thereof.

In certain embodiments, the process of the present application may further comprise step (c) of recovering the isobutylene. For example, isobutylene may be recovered by a variety of processes which are well-known and conventional in the art, e.g., by distillation and acid extraction with compounds such as polybasic mineral acids, particularly sulfuric acid in the range of about 55 to 70 weight percent. See, e.g., U.S. Pat. Nos. 2,981,767, 3,073,874, and 4,163,697, which are herein incorporated by reference in its entirety for all purposes.

In certain embodiments, the process of the present application may further comprise step (c) of recovering the propylene. Propylene may be recovered by a variety of processes which are well-known and conventional in the art, e.g., by distillation.

In certain embodiments, the process of the present application may further comprise step (c) of recovering the acetone. Acetone may be recovered by a variety of processes which are well-known and conventional in the art, e.g., by distillation.

Unreacted Water

In certain embodiments, any unreacted water remaining from the conversion of ethanol to isobutylene is isolated. In a further embodiment, the isolated water is recycled back to the front end of the reactor to minimize waste water. In another embodiment, the isolated water is contacted with an organic solvent immiscible with water to preferentially extract phenolic compounds for subsequent isolation via distillation. The organic solvent may then subsequently be recovered for recycle in a closed loop process system. Examples of preferred water immiscible organic solvents include, but are not limited to, ethyl acetate, toluene, mixed xylenes, and methyl-t-butyl ether. The resulting extracted water phase can be recycled to the front end of the process and mixed with ethanol.

Catalyst Regeneration

In certain embodiments, the $Zn_xZr_yA_vQ_sMn_wO_z$ mixed oxide catalyst or the bifunctional heterogeneous catalyst used the process disclosed herein is regenerated in situ. In a specific embodiment, the $Zn_xZr_yA_vQ_sMn_wO_z$ mixed oxide catalyst and the bifunctional heterogeneous catalyst is regenerated in situ by switching the process feed to an oxygen-containing stream while maintaining catalyst reaction temperatures as described herein to burn carbonaceous deposits.

Reactor

Suitable reactors include fixed-bed, adiabatic, fluid-bed, transport bed, and moving bed. In an exemplary embodiment, the reactor is a fixed bed reactor. In one embodiment, the catalyst bed length-to-diameter ratio is at least about 5 and preferably at least about 10, 100, or even 1000.

The catalytic conversion of ethanol to the reaction product can be run in batch, sequential batch (i.e., a series of batch reactors), or in continuous mode as described, for example, in H. Scott Fogler, (Elements of Chemical Reaction Engineering, 2nd Edition, (1992) Prentice-Hall Inc, CA). The processes and/or conversion may be carried out in any of the equipment customarily employed for batch, sequential batch, or in continuous mode processes. The condensate water formed as a product of the reaction may be removed by separation methods customarily employed for such separations.

Co-Product Formation and Recovery

In certain embodiments, functionalized hydrocarbons produced by the process (e.g., isobutylene, propylene, or acetone) includes the generation of one or more co-products during the catalytic reaction of the present application.

In some embodiments, co-products generated during the conversion of ethanol to isobutylene or propylene may include, without limitation, propylene (e.g., in the production of isobutylene), isobutylene (e.g., in the production of propylene), acetone (e.g., in the production of isobutylene and propylene), hydrogen, carbon dioxide, methane, and phenolic compounds such as phenol, 2-methyl phenol, 3-methyl phenol (meta-cresol), 2,5-dimethyl phenol, 3,5-dimethyl phenol (3,5-xylenol), 2,3-dimethyl phenol, and 3,4-dimethyl phenol. In some embodiments, one or more of the co-products may be produced.

Co-products generated during the conversion of ethanol to acetone may include, without limitation, in some embodiments, at least one phenolic compound selected from phenol, 2-methyl phenol, 3-methyl phenol (meta-cresol), 2,5-dimethyl phenol, 3,5-dimethyl phenol (3,5-xylenol), 2,3-dimethyl phenol, and 3,4-dimethyl phenol is generated during the conversion of ethanol to acetone. In one embodiment, each of the phenolic compounds selected from phenol, 2-methyl phenol, 3-methyl phenol (meta-cresol), 2,5-dimethyl phenol, 3,5-dimethyl phenol (3,5-xylenol), 2,3-dimethyl phenol, and 3,4-dimethyl phenol are generated during the conversion of ethanol to acetone. In some embodiments, at least one phenolic compound selected from phenol, 2-methyl phenol, 3-methyl phenol (meta-cresol), 2,5-dimethyl phenol, 3,5-dimethyl phenol (3,5-xylenol), 2,3-dimethyl phenol, and 3,4-dimethyl phenol is recovered following the conversion of ethanol to acetone. In one embodiment, each of the phenolic compounds selected from phenol, 2-methyl phenol, 3-methyl phenol (meta-cresol), 2,5-dimethyl phenol, 3,5-dimethyl phenol (3,5-xylenol), 2,3-dimethyl phenol, and 3,4-dimethyl phenol are recovered following the conversion of ethanol to acetone.

One or more of the phenolic compounds may be recovered by a variety of processes which are well-known and conventional in the art, e.g., by distillation techniques, including, but not limited to, vacuum distillation. In some embodiments, isolated unreacted water may be separated from phenolic compounds using a single stage flash, followed by distillation of the phenolic rich stream to remove any remaining water.

In some embodiments, propylene is generated during the ethanol to functionalized lower hydrocarbon (e.g., isobutylene) conversion. In one embodiment, the propylene generated during the ethanol to functionalized lower hydrocarbon conversion is recovered. In a more specific embodiment, the propylene is recovered via a pressure swing adsorption unit to result in high purity propylene, e.g., high purity bio-propylene, which may be used for, e.g., the manufacture of polymer grade polypropylene. In one embodiment, propylene is generated from ethanol at a yield of at least about 5%. In another embodiment, propylene is generated from ethanol at a yield of at least about 10%.

In some embodiments, isobutylene is generated during the ethanol to functionalized lower hydrocarbon (e.g., propylene) conversion. In one embodiment, the isobutylene generated during the ethanol to propylene conversion is recovered. In a more specific embodiment, the isobutylene is recovered via a pressure swing adsorption unit to result in high purity isobutylene, e.g., high purity bio-isobutylene, which may be used for, e.g., the manufacture of methyl methacrylate. In one embodiment, isobutylene is generated from ethanol at a yield of at least about 5%. In another embodiment, isobutylene is generated from ethanol at a yield of at least about 10%.

In some embodiments, acetone is generated during the ethanol to functionalized lower hydrocarbon conversion. In one embodiment, the acetone generated during the ethanol to functionalized lower hydrocarbon conversion is recovered. In a further embodiment, the acetone is recovered subsequent to the removal of excess water by condensation. In another embodiment, the acetone is collected using a selective adsorbent material and recovered with appropriate adsorbent regeneration steps.

In certain embodiments, the whole or a concentration of the acetone product stream from the ethanol to functionalized lower hydrocarbon reaction is recycled back to the reactor feed to convert residual acetone. In one embodiment, the recovered residual acetone is recycled back to the front end of the reactor and converted to isobutylene using a $Zn_xZr_yA_vQ_sMn_wO_z$ mixed oxide catalyst prepared utilizing either of the hard-template method, the co-precipitation method, or the impregnated method.

In an alternative embodiment, the isolated residual acetone can be converted to isobutylene using a β-zeolite catalyst. See, e.g., Hutchings et al., 1994, *Journal of Catalysis* 147: 177-185, which is herein incorporated by reference in its entirety for all purposes. In a further alternative embodiment, the isolated residual acetone can be converted to isobutylene using an alkali metal ion-exchanged BEA zeolite catalyst See, e.g., Tago et al., 2011, *Catalysis Today* 164: 158-162. In some embodiments, sequential reactors may be utilized to first convert ethanol to a product stream comprising isobutylene and acetone, and then subsequently acetone to isobutylene. For example, a first reactor may be utilized to first convert ethanol to a product stream comprising isobutylene and acetone, and a second reactor may be utilized to convert residual acetone to isobutylene.

In some embodiments, acetone is generated from ethanol at a yield of at least about 5%. In one embodiment, acetone is generated from ethanol at a yield of at least about 10%. In another embodiment, acetone is generated from ethanol at a yield of at least about 15%, at least about 20%, at least about 25%, at least about 30%, or at least about 35%.

As described herein, the present inventors have found that increasing the superficial velocity can increase selectivity to acetone with a corresponding decrease in isobutylene and/or propylene selectivity. Accordingly, the technology of the present application provides flexibility in that it allows one to swing the reaction towards isobutylene/propylene or towards acetone depending on which product is preferred based upon the prevailing market prices of isobutylene, propylene, and acetone. Thus, in another aspect, the present application is directed to a process for preparing a composition comprising at least one of isobutylene, propylene, and acetone, comprising: (a) feeding to a reactor a reactor feed comprising ethanol at a molar concentration of at least about 14%, and (b) contacting the ethanol with a $Zn_xZr_yA_vQ_sMn_wO_z$ mixed oxide catalyst in the reactor, whereby ethanol is converted to at least one of isobutylene, propylene, and acetone. In one embodiment, ethanol is converted to at least one functionalized hydrocarbon at a yield of at least about 30%. In other embodiments, ethanol is converted to at least one functionalized lower olefin at a yield of at least 50%. In such embodiments, co-products, e.g., propylene and/or acetone, are produced at a yield of less than 30%, e.g., a yield in the range of from 1% to 20%.

In some embodiments, hydrogen is generated during the ethanol to a functionalized lower hydrocarbon conversion. In one embodiment, the hydrogen generated during the ethanol to a functionalized lower hydrocarbon conversion is recovered, e.g., via a hydrogen recovery system. In some embodiments, the hydrogen recovery system comprises one or more units configured for condensation, amine scrubbing, pressure swing adsorption, cryogenic purification, flow of the gaseous waste stream through a hydrogen-permeable membrane, flow of the gaseous waste stream through a palladium membrane, flow of the gaseous waste stream through a hydrocarbon absorption medium, flow of the gaseous waste stream through a gas expansion unit, flow of the gaseous waste stream through a water gas shift chemical converter unit, or combinations thereof.

In some embodiments, $CO_2$ is generated during the ethanol to functionalized lower hydrocarbon conversion. In one embodiment, the $CO_2$ generated during the ethanol to functionalized lower hydrocarbon conversion is recovered. $CO_2$ may be recovered by a variety of techniques that are conventional and well-known in the art, e.g., through the use of a $CO_2$ absorbing solution, pressure swing adsorption, temperature swing adsorption, cryogenic purification, membrane separation, or combinations thereof.

In some embodiments, methane is generated during the ethanol to functionalized lower hydrocarbon conversion. In one embodiment, the methane generated during the ethanol to functionalized lower hydrocarbon conversion is recovered. Methane may be recovered by a variety of techniques that are conventional and well-known in the art, e.g., through the use of pressure swing adsorption, cryogenic purification, membrane separation, or combinations thereof.

In some embodiments, at least one phenolic compound selected from phenol, 2-methyl phenol, 3-methyl phenol (meta-cresol), 2,5-dimethyl phenol, 3,5-dimethyl phenol (3,5-xylenol), 2,3-dimethyl phenol, and 3,4-dimethyl phenol is generated during the conversion of ethanol to functionalized lower hydrocarbon conversion (e.g., isobutylene and/or propylene). In one embodiment, each of the phenolic compounds selected from phenol, 2-methyl phenol, 3-methyl phenol (meta-cresol), 2,5-dimethyl phenol, 3,5-dimethyl phenol (3,5-xylenol), 2,3-dimethyl phenol, and 3,4-dimethyl phenol are generated during the conversion of ethanol to functionalized lower hydrocarbon. In some embodiments, at least one phenolic compound selected from phenol, 2-methyl phenol, 3-methyl phenol (meta-cresol), 2,5-dimethyl phenol, 3,5-dimethyl phenol (3,5-xylenol), 2,3-dimethyl phenol, and 3,4-dimethyl phenol is recovered following the conversion of ethanol to functionalized lower hydrocarbon. In one embodiment, each of the phenolic compounds selected from phenol, 2-methyl phenol, 3-methyl phenol (meta-cresol), 2,5-dimethyl phenol, 3,5-dimethyl phenol (3,5-xylenol), 2,3-dimethyl phenol, and 3,4-dimethyl phenol are recovered following the conversion of ethanol to functionalized lower hydrocarbon. One or more of the phenolic compounds may be recovered by a variety of processes which are well-known and conventional in the art, e.g., by distillation techniques, including, but not limited to, vacuum distillation. In some embodiments, isolated unreacted water may be separated from phenolic compounds using a single stage flash, followed by distillation of the phenolic rich stream to remove any remaining water.

In certain embodiments, acetaldehyde is produced during the conversion of ethanol to functionalized lower hydrocarbon at a selectivity of less than about 10%. In another embodiment, acetaldehyde is produced during the conversion of ethanol to functionalized lower hydrocarbon at a selectivity of less than about 8%, less than about 6%, less than about 4%, less than about 2%, or less than about 0.5%. In an exemplary embodiment, acetaldehyde is produced during the conversion of ethanol to functionalized lower hydrocarbon at a selectivity of less than about 0.1%.

In another aspect, the present application provides at least one functionalized hydrocarbon (e.g., isobutylene) prepared by the methods of the present invention. In a further aspect, the present application provides high purity isobutylene prepared by the methods of the present invention. In yet another aspect, the present application provides high purity propylene prepared by the methods of the present invention. In other aspects, the present application provides isobutylene, propylene, acetone, hydrogen, carbon dioxide, methane, and one or more phenolic compounds selected from phenol, 2-methyl phenol, 3-methyl phenol (meta-cresol), 2,5-dimethyl phenol, 3,5-dimethyl phenol (3,5-xylenol), 2,3-dimethyl phenol, and 3,4-dimethyl phenol prepared by the methods of the present invention.

In another aspect, the present application provides methods for converting isobutylene produced by the methods of the present invention into high-value, beneficial hydrocarbons. In some embodiments, the beneficial hydrocarbons are selected from the group consisting of jet fuel blendstocks, isooctane, para-xylene, methacrolein, methyl methacrylate, and butyl rubber.

In yet another aspect, the present application provides methods for converting propylene produced by the methods of the present invention into high-value, beneficial hydrocarbons. In some embodiments, polypropylene and derivatives thereof are produced from high purity propylene produced via the ethanol to propylene reaction.

In yet another aspect, the present application provides methods for converting acetone produced by the methods of the present invention into high-value beneficial hydrocarbons. In some embodiments, the beneficial hydrocarbons are methyl methacrylate, and solvents.

In some embodiments, the beneficial hydrocarbons are selected from the group consisting of jet fuel blendstocks, isooctane, para-xylene, methacrolein, methyl methacrylate, tert-butanol, and butyl rubber.

Conversion of Isobutylene to Jet Fuels

In various embodiments described herein, the isobutylene generated by the methods of the present application can be converted into jet fuels and jet fuel blendstocks. Methods for the conversion of isobutylene into these products are described in U.S. Pat. Nos. 8,193,402, 8,373,012, 8,378,160, 8,450,543, 8,487,149, and 8,546,627. Accordingly, in another aspect, the application provides a process for preparing a jet fuel or jet fuel blendstock, comprising: (a) preparing isobutylene by the ethanol to isobutylene process described herein; and (b) converting said isobutylene into a jet fuel or jet fuel blendstock.

Conversion of Isobutylene to Isooctane

In various embodiments described herein, the isobutylene generated by the methods of the present application can be converted into isooctane. Methods for the conversion of isobutylene into this product are described in U.S. Pat. Nos. 8,193,402, 8,373,012, 8,378,160, 8,450,543, 8,487,149, and 8,546,627. Accordingly, in another aspect, the application provides a process for preparing isooctane, comprising: (a) preparing isobutylene by the ethanol to isobutylene process described herein; and (b) converting said isobutylene into isooctane.

Conversion of Isobutylene to Para-Xylene

In various embodiments described herein, the isobutylene generated by the methods of the present application can be converted into para-xylene. Methods for the conversion of isobutylene into para-xylene are described in U.S. Pat. Nos. 8,193,402, 8,373,012, 8,378,160, 8,450,543, 8,487,149, and 8,546,627, as well as U.S. Patent Application Publication Nos. 2011/0087000, and 2012/0171741. Accordingly, in another aspect, the application provides a process for preparing para-xylene, comprising: (a) preparing isobutylene by the ethanol to isobutylene process described herein; and (b) converting said isobutylene into para-xylene.

Conversion of Isobutylene to Methacrolein and Methyl Methacrylate

In various embodiments described herein, the isobutylene generated by the methods of the present application can be converted into methacrolein and methyl methacrylate. Methods for the conversion of isobutylene into methacrolein and methyl methacrylate are described in U.S. Pat. Nos. 8,193,402, 8,373,012, 8,378,160, 8,450,543, 8,487,149, and 8,546,627. Briefly, isobutylene can be oxidized over suitable metal oxide catalysts (e.g., using the methods described in JP 2005-253415) at temperatures of about 300-500° C. to methacrolein (MAL) which is then further oxidized to methacrylic acid at temperatures of about 350-500° C. The resultant methacrylic acid can be further esterified to methylmethacrylate. The oxidation of isobutene to MMA may also be accomplished in a single step (e.g., as described in WO/2003/053570). Accordingly, in another aspect, the application provides a process for preparing methacrolein, comprising: (a) preparing isobutylene by the ethanol to isobutylene process described herein; and (b) converting said isobutylene into methacrolein.

In yet another aspect, the application provides a process for preparing methylmethacrylate, comprising: (a) preparing isobutylene by the ethanol to isobutylene process described herein; (b) converting said isobutylene into methacrolein; (c) oxidizing the methacrolein of (b) into methacrylic acid; and (d) esterifying the methacrylic acid of (c) into methylmethacrylate.

Conversion of Isobutylene to Butadiene and Butyl Rubber

One of the major industrial uses of isobutylene is in the production of butyl rubber primarily for use in automobile tires. Butyl rubber is a high performance polymer comprised of high purity isobutylene cross-linked with di-olefins such as butadiene or isoprene (e.g. U.S. Pat. No. 2,984,644; Dhaliwal G K, Rubber Chemistry and Technology 1994, 67, p. 567). Typically, 1-3% of isoprene is blended with isobutylene and co-polymerized in the presence of a polymerization catalyst such as aluminum chloride and other metal salts. Thus, in various embodiments described herein, the isobutylene generated by the methods of the present application can be converted into butadiene and butyl rubber. Methods for the conversion of isobutylene into butyl rubber are described in U.S. Patent Application Publication No. 2010/0216958. Accordingly, in another aspect, the application provides a process for preparing butyl rubber, comprising: (a) preparing isobutylene by the ethanol to isobutylene process described herein; and (b) converting said isobutylene into butyl rubber.

This invention is further illustrated by the following examples that should not be construed as limiting.

EXAMPLES

Example 1

Ethanol to Isobutylene Conversion Using Hard-Template $Zn_xZr_yO_z$ Catalyst

Example 1A

Hard-Template $Zn_xZr_yO_z$ Catalyst Preparation & Reactor Setup

The $Zn_xZr_yO_z$ mixed-oxide catalyst was synthesized by the hard-templating method described in Sun et al., 2011, *J. Am. Chem. Soc.* 133: 11096-11099. Briefly, 12 g of BP2000 Carbon Black (Cabot) was dried overnight at 180° C. The precursor metal salts (Sigma Aldrich) were added to deionized water in an amount to produce a zinc-to-zirconium molar ratio of 1:12. The solution contained 19 g of zirconyl nitrate hydrate, 1.4 g zinc nitrate hexahydrate, and approximately 85 mL deionized water. The Zn and Zr nitrate mixture was sonicated for 15 minutes to produce a clear solution. 50 g of the solution was added to 12 g of dried carbon black to achieve incipient wetness.

The impregnated carbon black was dried overnight in the fume hood and then transferred to a box furnace for calcination at 400° C. for 4 h. Final calcination was carried out at 550° C. for 20 h. Ramp rates to calcination temperatures were 3° C./min. The yield of dry catalyst powder is approximately 3.5 g.

Heterogeneously catalyzed ethanol to isobutylene reactions take place in a packed bed of catalyst located inside of a ⅜" OD stainless steel reaction tube. Gaseous reagents are supplied by mass flow controllers and liquid reactants are supplied by syringe pump. The liquid reactants are mixtures of ethanol and water. A co flow of nitrogen provides an internal standard to quantify gaseous products. Prior to entering the reactor the nitrogen/ethanol/water mixture is effectively vaporized by preheating to 320° C. The flow reactor is enclosed in a heating furnace capable of heating the packed bed to 550° C.

Downstream of the flow reactor, gaseous products are separated from liquid products by a cold trap and both streams are sent to instrumentation for composition analysis.

Product streams are analyzed by gas chromatography (GC). Liquid samples are collected in a cold trap for offline analysis. Gaseous samples are directed to a GC sample loop equipped with a thermal conductivity detector (TCD).

Example 1B

Results with 14.8% Molar Concentration of Ethanol

Ethanol and water were mixed in a 1:2 ratio by mass. The ethanol-water mixture was fed to the reactor at a rate of 0.1 mL/min. A co-feed of nitrogen enables quantification of gaseous products including isobutylene, propylene, $CO_2$, acetone and methane. The total inlet mole concentration of ethanol for the baseline condition is 14.8%. The catalyst temperature is set to 485° C. The stainless steel reactor is loaded with 2.5 g of Zn—Zr mixed-metal-oxide catalyst prepared in Example 1A.

The product distribution based on carbon selectivity for the baseline conditions described above is shown in Table 1. The primary product is isobutylene at 45% carbon selectivity. The 45% carbon selectivity represents 67% of the theoretical maximum. There is 8% carbon converted to propylene (i.e., 11% of the theoretical maximum) and 14% carbon converted to acetone (i.e., 19% of the theoretical maximum). 26% carbon is converted to $CO_2$ and the remainder is converted to methane. Results for the present example indicate improved isobutylene selectivity at high concentrations of ethanol in the reactor feed. Increased selectivity to propylene relative to prior art methods was also observed. Indeed, 8% carbon was converted to propylene, which currently has a higher value relative to acetone and acetaldehyde.

TABLE 1

Carbon Selectivity in Product for Ethanol to Isobutylene Experiments at Ethanol Molar Concentration of 14.8%

| $CO_2$ | Propylene | Isobutylene | Acetone | Methane |
| --- | --- | --- | --- | --- |
| 26% | 8% | 45% | 14% | 8% |

Example 1C

Results with 25.3% Molar Concentration of Ethanol

The purpose of this example is to illustrate high isobutylene selectivity at increased concentrations of ethanol in the ethanol-to-isobutylene reactor feed.

In this example, ethanol and water were mixed in a 1:1 ratio by mass. The ethanol-water mixture was fed to the reactor at a rate of 0.1 mL/min. A co-feed of nitrogen enables quantification of gaseous products including isobutylene, propylene, $CO_2$, acetone and methane. The total inlet mole concentration of ethanol for this experiment is 25.3%. The catalyst temperature is set to 485° C. The stainless steel reactor is loaded with 2.5 g catalyst. The catalyst is a Zn—Zr mixed metal oxide as prepared in Example 1A.

The carbon selectivity for increased-ethanol-concentration experiments is shown in Table 2. The primary product is isobutylene at 46% carbon selectivity. The 46% carbon selectivity represents 69% of the theoretical maximum. There is 14% carbon converted to propylene (i.e., 19% of the theoretical maximum) and 3% carbon converted to acetone (i.e., 4% of the theoretical maximum). 25% carbon converts to $CO_2$ and the remainder converts to methane. The results here illustrate that the isobutylene selectivity is maintained at a high level for increased ethanol concentrations in the reactor feed. Increased selectivity to propylene relative to prior art methods was also observed. Indeed, 14% carbon was converted to propylene, which currently has a higher value relative to acetone and acetaldehyde.

TABLE 2

Carbon Selectivity in Product for Ethanol to Isobutylene Experiments at Ethanol Molar Concentration of 25.3%.

| $CO_2$ | Propylene | Isobutylene | Acetone | Methane |
|---|---|---|---|---|
| 25% | 14% | 46% | 3% | 12% |

Example 1D

Results Over Temperature Range

The following series of experimental results show the product selectivity for an inlet ethanol mole concentration of 14.8% with varying catalyst temperatures.

Figure 2:
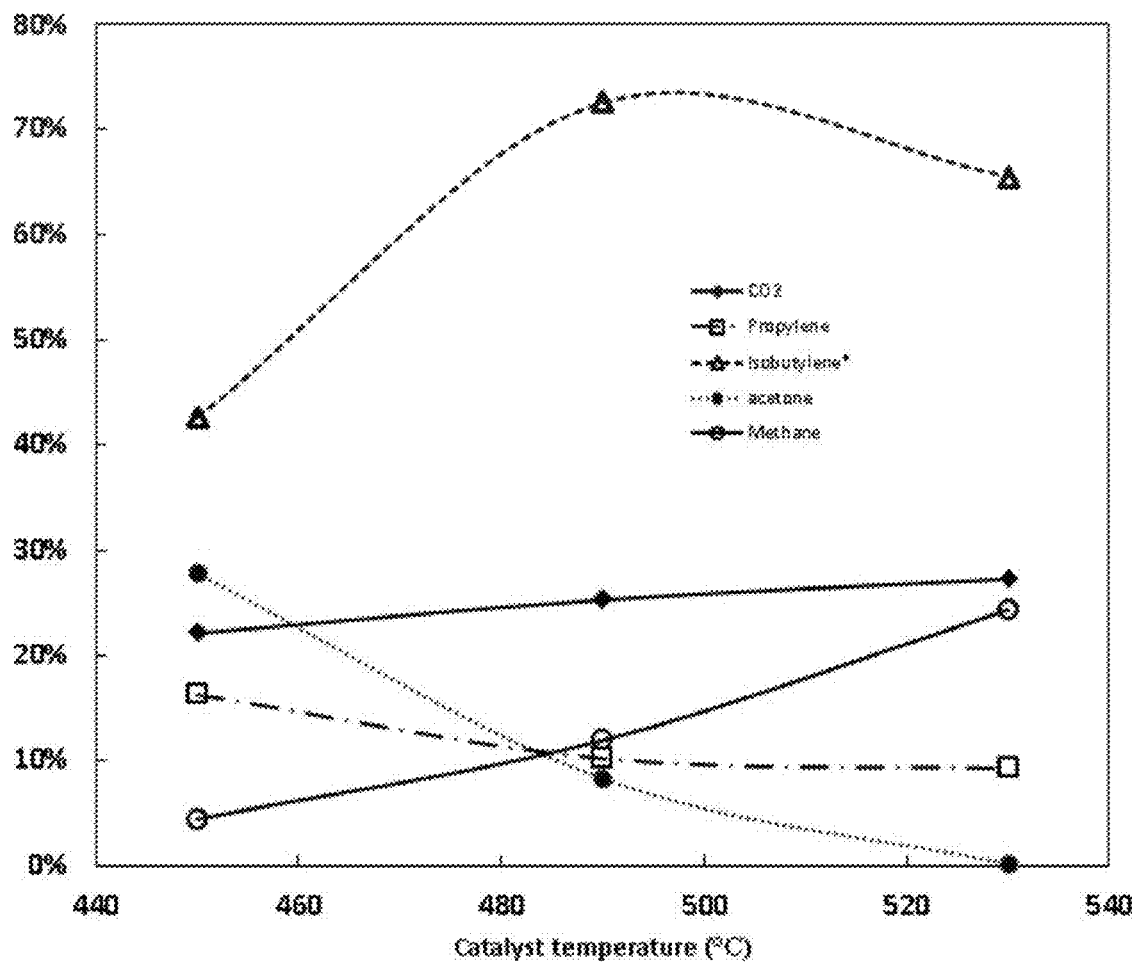
FIG. 2 illustrates product selectivity for an inlet ethanol mole concentration of 14.8% over a range of catalyst temperatures. Isobutylene is represented as a percent of theoretical maximum.

The baseline result is represented in the middle of FIG. 2 (485° C.). At lower temperatures (450° C.) the isobutylene selectivity is reduced while the acetone selectivity increases. At high temperatures (530° C.), the acetone selectivity decreases to a minimal value while the methane selectivity increases to 24%. At all temperatures tested the isobutylene selectivity was greater than 40% of the theoretical maximum with an inlet ethanol mole concentration of 14.8%.

Example 1E

Results Over Ethanol Range

This example illustrates high isobutylene selectivity over a range of feed ethanol concentrations. The tests were carried out at a catalyst temperature of 485° C. using the Zn—Zr catalyst prepared in Example 1A. The feed rate of the ethanol-water mixture was 0.1 mL/min.

Isobutylene selectivity was at least 60% of the theoretical maximum over a range of ethanol feed concentrations from 15% to 25%.

Example 1F

Shift from Isobutylene to Acetone by Modifying Superficial Velocity

This example illustrates that the product distribution can be varied by altering the superficial velocity of the feed to the ethanol-to-isobutylene reactor. All experiments in the following figure were carried out using a Zn—Zr mixed metal oxide catalyst prepared as described in Example 1A. The catalyst temperature for this experiment was 485° C.

Figure 3:
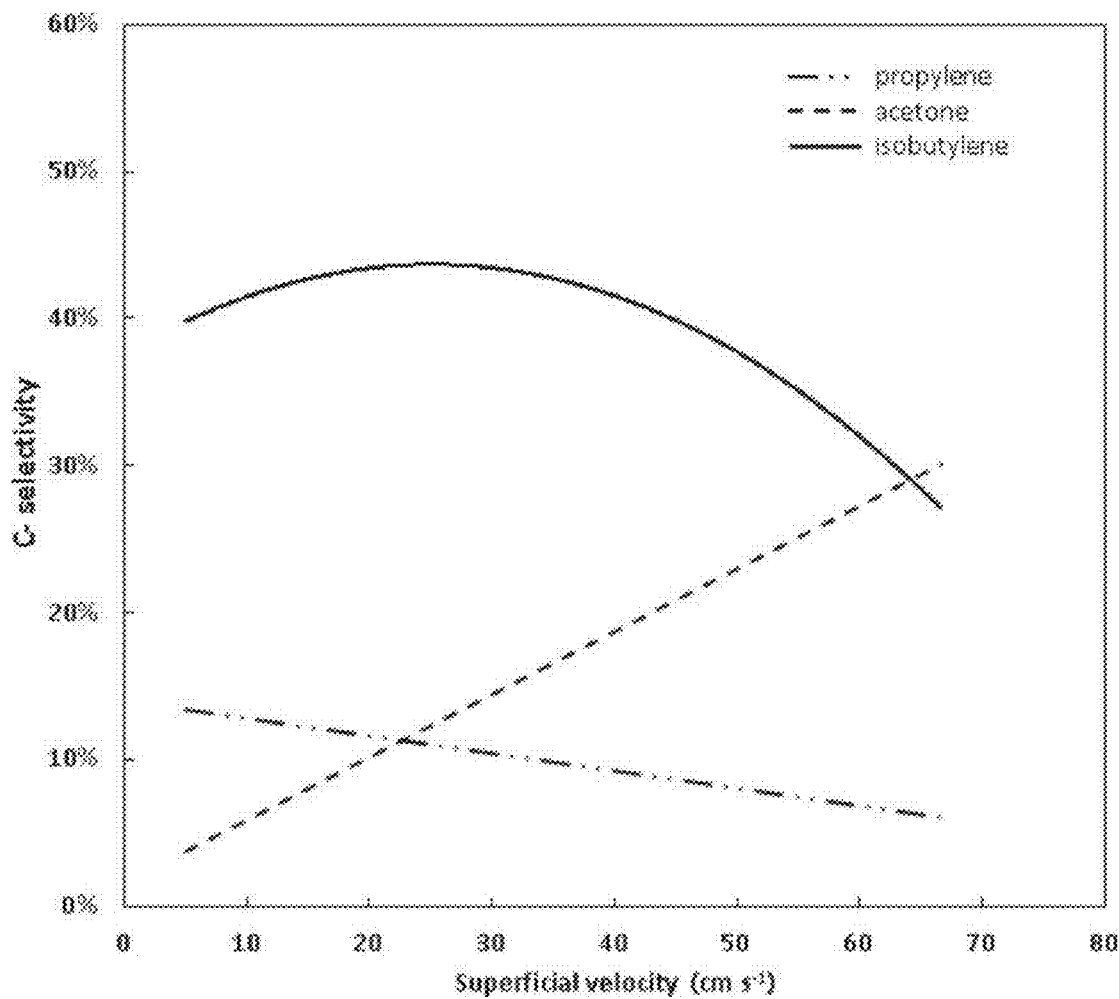
FIG. 3 illustrates product distributions for ethanol to isobutylene reactions relative to superficial velocity. Numbers are shown in terms of carbon selectivity.

The results in FIG. 3 indicate that the product distribution can be altered by varying the feed rate to the reactor. At high superficial velocities the dominant product is acetone with similar conversion to isobutylene and minimal conversion to propylene. As one increases the residence time (decreases the superficial velocity) the acetone selectivity is reduced while selectivities to propylene and isobutylene increase. The isobutylene selectivity reaches a maximum around 25-30 cm s$^{-1}$ while the propylene carbon selectivity continues to increase with increasing residence time (decreasing velocity).

Example 1G

Fuel-Grade Ethanol Vs. Solvent-Grade Ethanol

The purpose of this example is to evaluate the impact of using fuel-gradeethanol (97.5% w/w pure) on the ethanol-to-isobutylene reaction. For this experiment an ethanol-water mixture was fed to the Zn—Zr catalyst prepared in Example 1 at a rate of 0.1 mL/min. The catalyst temperature was 485° C. and the inlet mole concentration of ethanol is approximately 14.8%.

Figure 4:
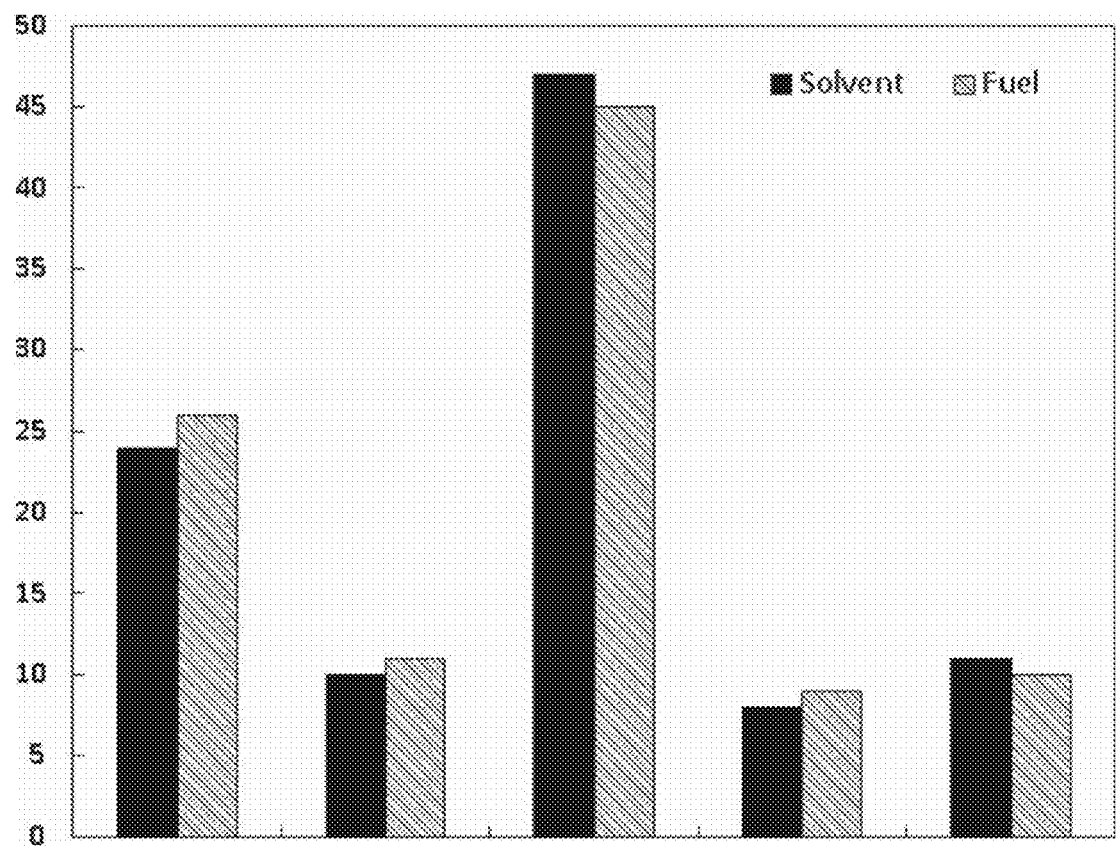
FIG. 4 illustrates product distributions for fuel-grade and solvent-grade ethanol feeds to the ethanol to isobutylene reaction. Numbers are shown in terms of carbon selectivity.

FIG. 4 illustrates the product distribution when using fuel-grade ethanol relative to solvent-grade ethanol. The impact of using fuel-grade ethanol as a feed to the reaction isobutylene carbon selectivity is minimal.

Example 1H

Isobutylene Purity

The following experiment was carried out to determine the purity of isobutylene formed from ethanol using a Zn—Zr mixed-metal-oxide catalyst. During a baseline ethanol-to-isobutylene experiment (described in Example 2A) the product stream was collected in a dry-ice trap and then dissolved into diisobutylene for liquid injection on GC equipped with FID. The resulting chromatogram is shown in FIG. 5 with the relative peak areas in Table 3.

TABLE 3

Figure 5:
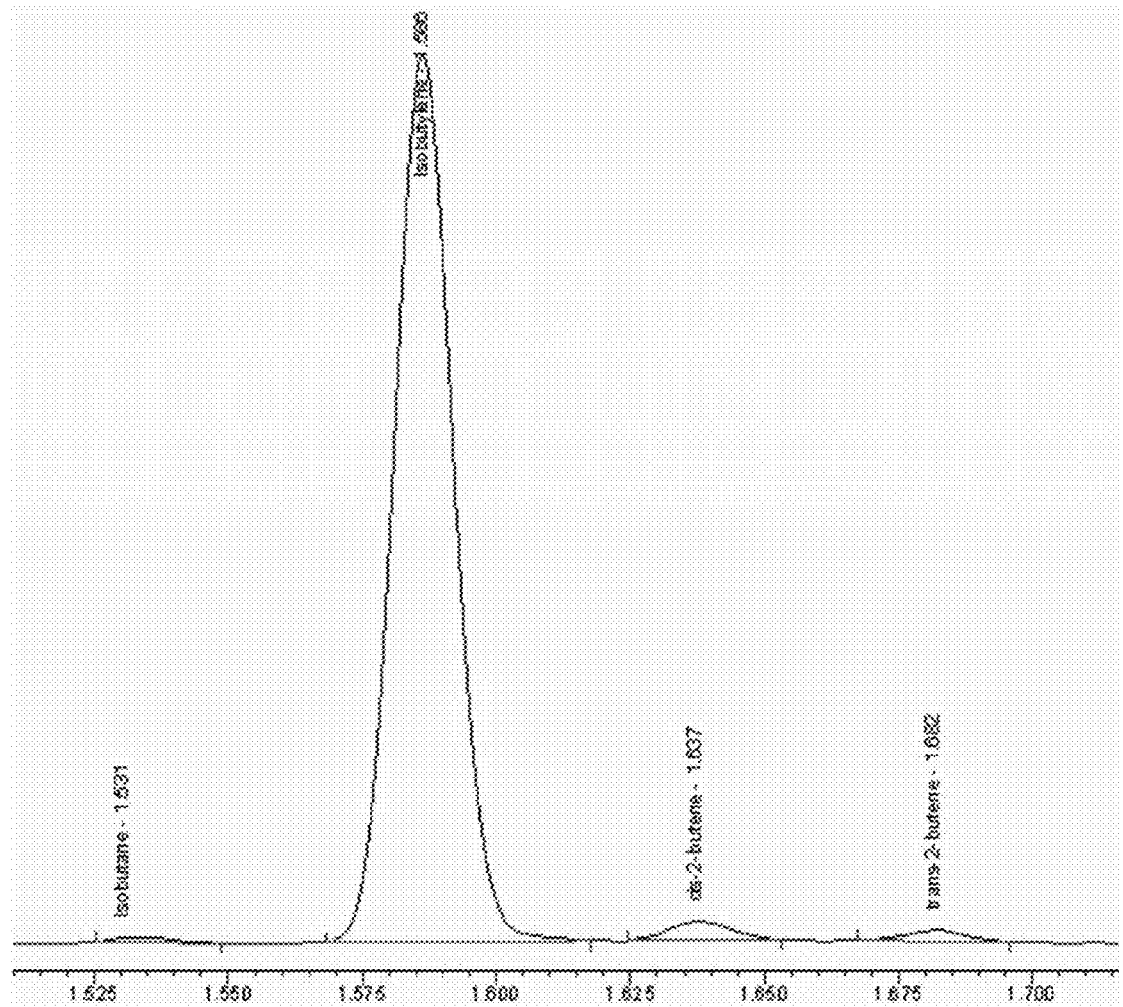
FIG. 5 illustrates a GC chromatogram showing C4 purity from ethanol to isobutylene experiments.

Relative Peak Areas for GC Chromatogram in FIG. 5.

| Peak Name | Relative Area (%) |
|---|---|
| Isobutane | 0.56 |
| Isobutylene | 96.21 |
| cis-2-butene | 2.08 |
| trans-2-butene | 1.16 |

* - Less than 0.5% of the peak is likely attributable to n-butene

The results indicate a high selectivity to isobutylene relative to other C4 olefins and paraffins from the ethanol-to-isobutylene reaction carried out on Zn—Zr mixed metal oxide catalysts.

Example 1I

Phenolic Compounds

Figure 6:
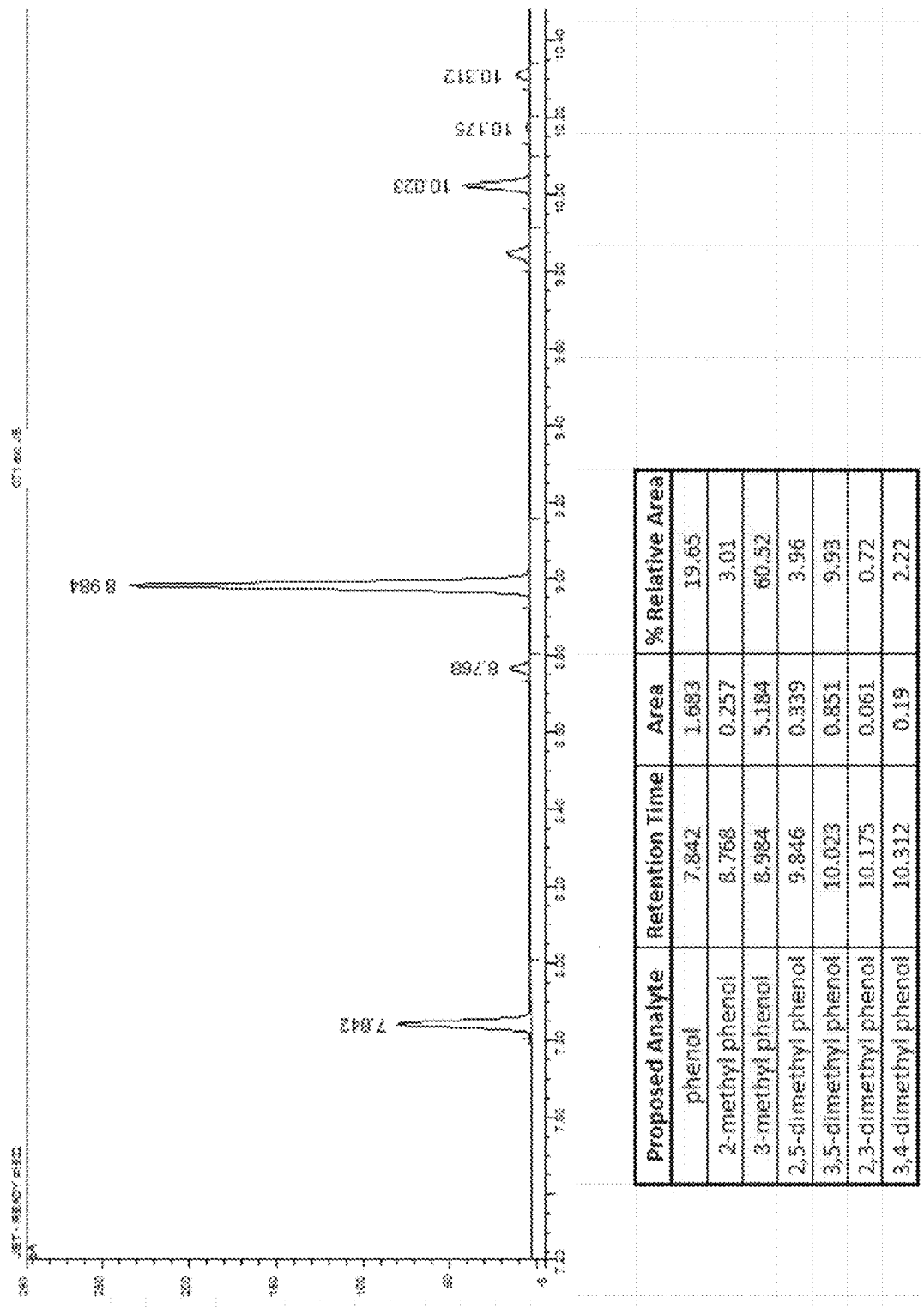
FIG. 6 illustrates a GC chromatogram showing the production of phenolic compounds and the relative distributions.

The primary products in the liquid concentration of the ethanol to isobutylene reaction products are acetone, water, and phenolic compounds. The phenolic compounds include phenol, 2-methyl phenol, 3-methyl phenol (meta-cresol), 2,5-dimethyl phenol, 3,5-dimethyl phenol (3,5-xylenol), 2,3-dimethyl phenol, and 3,4-dimethyl phenol. An internal standard (butanone) enables quantification of acetone in the liquid product. A chromatogram showing the typical phenolic compounds and relative distributions is shown in FIG. 6. The phenolic compounds such as phenol, meta-cresol, and 3,5-xylenol are currently more valuable in the marketplace relative to acetone. They have a variety of uses in the production of foods, cosmetics, and pharmaceuticals. This is the first report to describe the production of high-value phenolic compounds in an ethanol to isobutylene conversion.

Example 2

Ethanol to High Purity Isobutylene Conversion Using Co-Precipitated $Zn_xZr_yO_z$ Catalyst

Example 2A

Co-Precipitation Catalyst Preparation & Reactor Setup

Separately, the required amount of $ZrO(NO_3)_2$ (99%) and $Zn(NO_3)_2 \cdot 6H_2O$ (99.8%) were dissolved in 70 g DI (deionized) water to prepare the stock metal salt solutions to deliver the required Zn/Zr molar ratio. For example, a 1/20 Zn/Zr ratio was prepared by adding 10 g of $ZrO(NO_3)_2$ (99%) and 0.66 g of $Zn(NO_3)_2 \cdot 6H_2O$ (99.8%) to 70 g of DI water. The resulting salt solution is heated until the salts are fully dissolved. The various Zn to Zr molar ratios (1:12, 1:20, 1:25, 1:36) were all prepared from these stock solutions. To a 0.5 L round bottom flask equipped with a magnetic stirrer, the appropriate metal salt solution was added. To the stirring acidic salt solution (pH<1), at room temperature, was initiated drop wise addition of a 20 wt % NaOH solution (typical addition times are 10-15 minutes), prepared from DI water and NaOH pellets as purchased from Aldrich chemical, until pH 7.25-7.75 is attained. After addition of the 20 wt % NaOH solution (typical addition amounts 11-12 g), and attaining target pH, the solution is stirred at room temperature for an additional 60 minutes. The resulting precipitate is filtered and washed with warm DI water. The filter cake is dried at 140° C. for 3 hours, and calcined at 500° C. for 4 h in a muffle furnace. The metal oxides were used directly as prepared.

Heterogeneously catalyzed ethanol to isobutylene reactions take place in a packed bed of catalyst located inside of a ⅜" OD stainless steel reaction tube. Gaseous reagents are supplied by mass flow controllers and liquid reactants are supplied by syringe pump. The liquid reactants are mixtures of ethanol and water. A co-flow of nitrogen provides an internal standard to quantify gaseous products. Prior to entering the reactor the nitrogen/ethanol/water mixture is effectively vaporized by preheating to 320° C. The flow reactor is enclosed in a heating furnace capable of heating the packed bed to 550° C.

Downstream of the flow reactor, gaseous products are separated from liquid products by a cold trap and both streams are sent to on-line instrumentation for composition analysis.

Product streams are analyzed by gas chromatography (GC). Liquid samples are collected in a cold trap for offline analysis. Gaseous samples are directed to a GC sample loop equipped with a thermal conductivity detector (TCD).

Example 2B

Results with 25.4% Molar Concentration of Ethanol

Ethanol and water were mixed in a 1:1 ratio by mass. The ethanol-water mixture was fed to the reactor at a rate of 0.1 mL/min. A co-feed of nitrogen enables quantification of gaseous products including isobutylene, propylene, $CO_2$, acetone and methane. The total inlet mole concentration of ethanol for the baseline condition is 25.4%. The catalyst temperature is set to 460° C. The stainless steel reactor is loaded with 2.5 g of Zn—Zr mixed-metal-oxide catalyst prepared in Example 2A for a co-precipitated catalyst prepared with a 1/25 Zn/Zr ratio.

The product distribution based on carbon selectivity for the baseline conditions described above is shown in Table 4. The primary product is isobutylene at 50.4% carbon selectivity. The 50.4% carbon selectivity represents 75.2% of the theoretical maximum. There is 10.8% carbon converted to propylene, 1.2% carbon converted to ethylene, 2.3% carbon converted to acetone, 24.6% carbon converted to $CO_2$, and the remainder or carbon is converted to methane. Tables 5-7 present results of isobutylene purity for co-precipitated catalyst versus impregnated and hard-templated catalysts at various Zn/Zr ratios. Results for the present example indicate improved isobutylene selectivity at high concentrations of ethanol in the reactor feed.

TABLE 4

Carbon Selectivity in Product for Ethanol to Isobutylene Experiments at Ethanol Molar Concentration of 25.4%

| $CO_2$ | Ethylene | Propylene | Isobutylene | Acetone | Methane |
|---|---|---|---|---|---|
| 24.6% | 1.2% | 10.8% | 50.4% | 2.3% | 9.9% |

TABLE 5

Isobutylene Purity in Product for Ethanol to Isobutylene Experiments at Ethanol Molar Concentration of 25.4% with co-precipitated catalyst with Zn/Zr ratio of 1/25 at reaction temperature of 460° C.

| Isobutylene | n-Butene | cis-2-butene | trans-2-butene | isobutane |
|---|---|---|---|---|
| 99.70% | 0.04% | 0.01% | 0.04% | 0.21% |

TABLE 6

Isobutylene Purity in Product for Ethanol to Isobutylene Experiments at Ethanol Molar Concentration of 25.4% with impregnated catalyst with Zn/Zr ratio of 1/12 at reaction temperature of 460° C.

| Isobutylene | n-Butene | cis-2-butene | trans-2-buyene | isobutane |
|---|---|---|---|---|
| 97.28% | 0.85% | 0.70% | 1.09% | 0.08% |

TABLE 7

Isobutylene Purity in Product for Ethanol to Isobutylene Experiments at Ethanol Molar Concentration of 25.4% with impregnated catalyst with Zn/Zr ratio of 1/25 at reaction temperature of 460° C.

| Isobutylene | n-Butene | cis-2-butene | trans-2-butene | isobutane |
|---|---|---|---|---|
| 95.68% | 1.72% | 1.15% | 1.45% | 0.00% |

Example 2C

Comparative Results with 25.3% Molar Concentration of Ethanol with Impregnated Catalyst at Zn/Zr Ratio 1/25

The purpose of this example is to illustrate carbon selectivity at increased concentrations of ethanol in the ethanol-to-isobutylene reactor feed with impregnated catalyst at an identical Zn/Zr ratio of 1/25 as a direct comparison to the co-precipitated catalyst In this example, ethanol and water were mixed in a 1:1 ratio by mass. The ethanol-water mixture was fed to the reactor at a rate of 0.1 mL/min. A co-feed of nitrogen enables quantification of gaseous products including isobutylene, propylene, $CO_2$, acetone and methane. The total inlet mole concentration of ethanol for this experiment is 25.3%. The catalyst temperature is set to 460° C. The stainless steel reactor is loaded with 2.5 g catalyst. The catalyst is a Zn—Zr mixed metal oxide as prepared via classical incipient wetness impregnation technique.

The carbon selectivity for increased-ethanol-concentration experiments is shown in Table 8 for the impregnated catalyst with a Zn/Zr ratio of 1/25. The primary product is acetone at 39.7% carbon selectivity indicative of poor catalytic activity with regard to conversion of acetone to isobutylene. There is 14.1% carbon converted to propylene (19% molar yield from ethanol), 22.9% carbon converted to isobutylene (34% molar yield from ethanol), 5.8% carbon converted to ethylene (indicating significantly higher levels of ethanol dehydration), 14.2% carbon converts to $CO_2$ (indicative of higher ethylene levels and lower isobutylene levels), and the remainder converts to methane. The results here illustrate the significantly different performance between the impregnated and co-precipitated catalyst with regard to catalyst activity with regard to isobutylene formation, optimal Zn/Zr ratios, and product isobutylene purity.

TABLE 8

Carbon Selectivity in Product for Ethanol to Isobutylene Experiments at Ethanol Molar Concentration of 25.3% with impregnated catalyst with Zn/Zr ratio 1/25.

| $CO_2$ | Ethylene | Propylene | Isobutylene | Acetone | Methane |
|---|---|---|---|---|---|
| 14.2% | 5.8% | 14.1% | 22.9% | 39.7% | 3.2% |

Example 3

Ethanol to High Purity Propylene Conversion Using Co-Precipitated $Zn_2Zr_yO_z$ Catalyst Example 3A Co-Precipitation Catalyst Preparation & Reactor Setup Separately, the required amount of $ZrO(NO_3)_2$ (99%) and $Zn(NO_3)_2 \cdot 6H_2O$ (99.8%) were dissolved in 70 g DI (deionized) water to prepare the stock metal salt solutions to deliver the required Zn/Zr molar ratio. For example, a 1/12 Zn/Zr ratio was prepared by adding 10 g of $ZrO(NO_3)_2$ (99%) and 1.2 g of $Zn(NO_3)_2 \cdot 6H_2O$ (99.8%) to 70 g of DI water. The resulting salt solution is heated until the salts are fully dissolved. The various Zn to Zr molar ratios (1:12, 1:20, 1:25, 1:36) were all prepared from these stock solutions. To a 0.5 L round bottom flask equipped with a magnetic stirrer, the appropriate metal salt solution was added followed by the addition of 3 g of BP2000 Carbon Black (Cabot). To the stirring acidic salt and carbon black slurry solution (pH<1), preferably at room temperature or between 25-100° C., was initiated drop wise addition of a 20 wt % NaOH solution (typical addition times are 10-15 minutes), prepared from DI water and NaOH pellets as purchased from Aldrich chemical, until pH 7-9 is attained. After addition of the 20 wt % NaOH solution (typical addition amounts 11-12 g), and attaining target pH, the solution is stirred at room temperature, or at the target precipitation temperature, for an additional 60 minutes. The resulting precipitate is filtered and washed with warm DI water. The filter cake is dried at 140° C. for 3 hours, and calcined at 500° C. for 4 h in a muffle furnace. The metal oxides were used directly as prepared.

Heterogeneously catalyzed ethanol to propylene reactions take place in a packed bed of catalyst located inside of a ⅜" OD stainless steel reaction tube. Gaseous reagents are supplied by mass flow controllers and liquid reactants are supplied by syringe pump. The liquid reactants are mixtures of ethanol and water. A co-flow of nitrogen provides an internal standard to quantify gaseous products. Prior to entering the reactor the nitrogen/ethanol/water mixture is effectively vaporized by preheating to 320° C. The flow reactor is enclosed in a heating furnace capable of heating the packed bed to 550° C.

Downstream of the flow reactor, gaseous products are separated from liquid products by a cold trap and both streams are sent to on-line instrumentation for composition analysis.

Product streams are analyzed by gas chromatography (GC). Liquid samples are collected in a cold trap for offline analysis. Gaseous samples are directed to a GC sample loop equipped with a thermal conductivity detector (TCD).

Example 3B

Results with 25.4% Molar Concentration of Ethanol

Fuel grade Ethanol and water were mixed in a 1:1 ratio by mass. The ethanol-water mixture was fed to the reactor at a rate of 0.1 mL/min. A co-feed of nitrogen enables quantification of gaseous products including isobutylene, propylene, $CO_2$, acetone and methane. The total inlet mole concentration of ethanol for the baseline condition is 25.4%. The catalyst temperature is set to 460° C. The stainless steel reactor is loaded with a mixture of 2.5 g of Zn—Zr mixed-metal-oxide catalyst prepared in Example 3A for a co-precipitated catalyst prepared with a 1/12 Zn/Zr ratio with 2.5 g of glass beads.

The product distribution based on carbon selectivity for the baseline conditions described above is shown in Table 9. The primary product is propylene at 63.2% carbon selectivity. The 63.2% carbon selectivity represents 84.3% of the theoretical maximum (63.2%/75.0%=84.3%). There is 6.2% carbon converted to isobutylene, 4.1% carbon converted to ethylene, 0.8% carbon converted to acetone, 23.1% carbon converted to $CO_2$, and the remainder or carbon is converted to methane. Table 10 present results of propylene purity for co-precipitated catalyst prepared in the presence of carbon black at Zn/Zr ratio of 1/12. Results for the present example indicate improved propylene selectivity at high concentrations of ethanol in the reactor feed.

TABLE 9

Carbon Selectivity in Product for Ethanol to Propylene Experiments at Ethanol Molar Concentration of 25.4%

| Propylene | $CO_2$ | Ethylene | Isobutylene | Acetone | Methane |
|---|---|---|---|---|---|
| 63.2% | 23.1% | 4.1% | 6.2% | 0.8% | 3.0% |

TABLE 10

Propylene Purity based on GC Area % in Product for Ethanol to Propylene Experiments at Ethanol Molar Concentration of 25.4% with co-precipitated catalyst with Zn/Zr ratio of 1/12 at reaction temperature of 460° C.

| Propylene | Propane |
|---|---|
| 99.68% | 0.32% |

Example 4

Ethanol to High Purity Butylene Using Impregnated $Zn_xZr_yMn_wO$ Catalyst

Example 4A

Impregnated $Zn_xZr_yMn_wO$ Catalyst Preparation & Reactor Setup

Separately, the required amount of $Zn(NO_3)_2 \cdot 6H_2O$ (99.8%) was dissolved in 3.5 g DI (deionized) water to prepare the stock metal salt solutions to deliver the required Zn/Zr/Mn molar ratio. For example, a 0.3/8/1 Zn/Zr/Mn ratio was prepared by adding 0.60 g of $Zn(NO_3)_2 \cdot 6H_2O$ (99.8%) to 3.5 g of DI water. The resulting salt solution is added dropwise to 6 g of commercially available Zr/Mn catalyst as supplied by Clariant Corporation. The resulting impregnated $Zn_xZr_yMn_wO$ paste is dried at 413 K for 3 hours, and calcined at 500° C. for 4 h in a muffle furnace. The metal oxides were used directly as prepared.

Heterogeneously catalyzed ethanol to isobutylene reactions take place in a packed bed of catalyst located inside of a ⅜" OD stainless steel reaction tube. Gaseous reagents are supplied by mass flow controllers and liquid reactants are supplied by syringe pump. The liquid reactants are mixtures of ethanol and water. A co-flow of nitrogen provides an internal standard to quantify gaseous products. Prior to entering the reactor the nitrogen/ethanol/water mixture is effectively vaporized by preheating to 320° C. The flow reactor is enclosed in a heating furnace capable of heating the packed bed to 550° C.

Downstream of the flow reactor, gaseous products are separated from liquid products by a cold trap and both streams are sent to on-line instrumentation for composition analysis.

Product streams are analyzed by gas chromatography (GC). Liquid samples are collected in a cold trap for offline analysis. Gaseous samples are directed to a GC sample loop equipped with a thermal conductivity detector (TCD).

Example 4B

Results with 25.4% Molar Concentration of Ethanol

Ethanol and water were mixed in a 1:1 ratio by mass. The ethanol-water mixture was fed to the reactor at a rate of 0.1 mL/min. A co-feed of nitrogen enables quantification of gaseous products including isobutylene, propylene, $CO_2$, acetone and methane. The total inlet mole concentration of ethanol for the baseline condition is 25.4%. The catalyst temperature is set to 460° C. The stainless steel reactor is loaded with 2.5 g of Zn—Zr—Mn mixed-metal-oxide catalyst prepared in Example 4A for an impregnated catalyst prepared with a 0.3/8/1 Zn/Zr ratio.

The product distribution based on carbon selectivity for the baseline conditions described above is shown in Table 11. The primary product is isobutylene at 50.4% carbon selectivity. The 50.4% carbon selectivity represents 75.2% of the theoretical maximum. There is 10.8% carbon converted to propylene, 1.2% carbon converted to ethylene, 2.3% carbon converted to acetone, 24.6% carbon converted to $CO_2$, and the remainder or carbon is converted to methane. Results for the present example indicate improved isobutylene selectivity at high concentrations of ethanol in the reactor feed.

TABLE 11

Carbon Selectivity in Product for Ethanol to Isobutylene Experiments at Ethanol Molar Concentration of 25.4%

| $CO_2$ | Ethylene | Propylene | Isobutylene | Acetone | Methane |
|---|---|---|---|---|---|
| 24.6% | 1.2% | 10.8% | 50.4% | 2.3% | 9.9% |

Example 4C

Comparative Results with 25.3% Molar Concentration of Ethanol with Commercial Zr/Mn Catalyst at Ratio 8/1

The purpose of this example is to illustrate carbon selectivity at increased concentrations of ethanol in the ethanol-to-isobutylene reactor feed with commercial catalyst at an identical Zr/Mn ratio of 8/1 as a direct comparison to the zinc impregnated Zn—Zr—Mn mixed-metal-oxide catalyst.

In this example, ethanol and water were mixed in a 1:1 ratio by mass. The ethanol-water mixture was fed to the reactor at a rate of 0.1 mL/min. A co-feed of nitrogen enables quantification of gaseous products including isobutylene, propylene, $CO_2$, acetone and methane. The total inlet mole concentration of ethanol for this experiment is 25.3%. The catalyst temperature is set to 460° C. The stainless steel reactor is loaded with 2.5 g catalyst. The catalyst is a Zr/Mn mixed metal oxide as commercially available.

The carbon selectivity for increased-ethanol-concentration experiments is shown in Table 12 for the commercial catalyst with a Zr/Mn ratio of 8/1. The primary product is ethylene at 39.7% carbon selectivity indicative of poor selectivity with regard to conversion of ethanol to isobutylene. There is 14.1% carbon converted to propylene (19% molar yield from ethanol), 22.9% carbon converted to isobutylene (34% molar yield from ethanol), 5.8% carbon converted to ethylene (indicating significantly higher levels of ethanol dehydration), 14.2% carbon converts to $CO_2$ (indicative of higher ethylene levels and lower isobutylene levels), and the remainder converts to methane. The results here illustrate the significantly different performance between the impregnated and co-precipitated catalyst with regard to catalyst activity with regard to isobutylene formation, optimal Zr/Mn ratios, and product isobutylene purity.

TABLE 12

Carbon Selectivity in Product for Ethanol to Isobutylene Experiments at Ethanol Molar Concentration of 25.4%

| $CO_2$ | Ethylene | Propylene | Isobutylene | Acetone | Methane |
|---|---|---|---|---|---|
| 15% | 40% | 15% | 5% | 24% | 1% |

Example 5

Ethanol to High Purity Propylene Conversion Using Co-Precipitated $Zn_xZr_ySi_wO_z$ Catalyst

Example 5A

Co-Precipitation Catalyst Preparation & Reactor Setup

Separately, the required amount of $ZrO(NO_3)_2$ (99%) and $Zn(NO_3)_2 \cdot 6H_2O$ (99.8%) were dissolved in 70 g DI (deionized) water to prepare the stock metal salt solutions to deliver the required Zn/Zr molar ratio. For example, a 1/12 Zn/Zr ratio was prepared by adding 10 g of $ZrO(NO_3)_2$ (99%) and 1.2 g of $Zn(NO_3)_2 \cdot 6H_2O$ (99.8%) to 70 g of DI water. The resulting salt solution is heated until the salts are fully dissolved. The various Zn to Zr molar ratios (1:8, 1:12, 1:20, 1:25, 1:36) were all prepared from these stock solutions. To a 0.5 L round bottom flask equipped with a magnetic stirrer, the appropriate metal salt solution was added followed by the addition of 3 g of BP2000 Carbon Black (Cabot). After assuring the carbon black is fully wetted, add 0.45 g of finely crushed silicon dioxide to the flask, and stir the resulting mixture for an additional 5-10 minutes. To the stirring acidic salt, carbon black, and silicon dioxide slurry solution (pH<1), preferably at room temperature or between 25-100° C., was initiated drop wise addition of a 20 wt % NaOH solution (typical addition times are 10-15 minutes), prepared from DI water and NaOH pellets as purchased from Aldrich chemical, until pH 6-8 is attained. After addition of the 20 wt % NaOH solution (typical addition amounts 11-12 g), and attaining target pH, the solution is stirred at room temperature, or at the target precipitation temperature, for an additional 60 minutes. The resulting precipitate is filtered and washed with warm DI water. The filter cake is dried at 140° C. for 2-3 hours, and calcined at 500° C. for 4 h in a muffle furnace. The metal oxides were used directly as prepared.

Heterogeneously catalyzed ethanol to propylene reactions take place in a packed bed of catalyst located inside of a 3/8" OD stainless steel reaction tube. Gaseous reagents are supplied by mass flow controllers and liquid reactants are supplied by syringe pump. The liquid reactants are mixtures of ethanol and water. A co-flow of nitrogen provides an internal standard to quantify gaseous products. Prior to entering the reactor the nitrogen/ethanol/water mixture is effectively vaporized by preheating to 320° C. The flow reactor is enclosed in a heating furnace capable of heating the packed bed to 550° C.

Downstream of the flow reactor, gaseous products are separated from liquid products by a cold trap and both streams are sent to on-line instrumentation for composition analysis.

Product streams are analyzed by gas chromatography (GC). Liquid samples are collected in a cold trap for offline analysis. Gaseous samples are directed to a GC sample loop equipped with a thermal conductivity detector (TCD).

Example 5B

Results with 25.4% Molar Concentration of Ethanol

Fuel grade Ethanol and water were mixed in a 1:1 ratio by mass. The ethanol water mixture was fed to the reactor at a rate of 0.1 mL/min. A co-feed of nitrogen enables quantification of gaseous products including isobutylene, propylene, $CO_2$, acetone and methane. The total inlet mole concentration of ethanol for the baseline condition is 25.4%. The catalyst temperature is set to 460° C. The stainless steel reactor is loaded with a mixture of 2.5 g of Zn—Zr—Si mixed-metal-oxide catalyst prepared in Example 5A for a co-precipitated catalyst prepared with a 1/12/2 Zn/Zr/Si ratio with 2.5 g of glass beads.

The product distribution based on carbon selectivity for the baseline conditions described above is shown in Table 13. The primary product is propylene at 60.7% carbon selectivity. The 60.7% carbon selectivity represents 80.9% of the theoretical maximum. There is 8.4% carbon converted to isobutylene, 3.3% carbon converted to ethylene, 0.20% carbon converted to acetone, 22.9% carbon converted to $CO_2$, and the remainder or carbon is converted to methane. Results for the present example indicate improved propylene selectivity at high concentrations of ethanol in the reactor feed.

TABLE 13

Carbon Selectivity in Product for Ethanol to Propylene Experiments at Ethanol Molar Concentration of 25.4%

| Propylene | $CO_2$ | Ethylene | Isobutylene | Acetone | Methane |
|---|---|---|---|---|---|
| 60.7% | 22.9% | 3.3% | 8.4% | 0.20% | 4.5% |

Example 6

Ethanol to High Quality Propylene Conversion Using Co-Precipitated $Zn_xZr_yAl_wO_z$ Mixed Oxide Catalyst

Example 6A

Co-Precipitation Catalyst Preparation & Reactor Setup

Separately, the required amount of $ZrO(NO_3)_2$ (99%) and $Zn(NO_3)_2 \cdot 6H_2O$ (99.8%) were dissolved in 70 g DI (deionized) water to prepare the stock metal salt solutions to deliver the required Zn/Zr molar ratio. For example, a 1/12 Zn/Zr ratio was prepared by adding 10 g of $ZrO(NO_3)_2$ (99%) and 1.2 g of $Zn(NO_3)_2 \cdot 6H_2O$ (99.8%) to 70 g of DI water. The resulting salt solution is heated until the salts are fully dissolved. The various Zn to Zr molar ratios (1:8, 1:12, 1:20, 1:25, 1:36) were all prepared from these stock solutions. To a 0.5 L round bottom flask equipped with a magnetic stirrer, the appropriate (Zn/Zr) metal salt solution was added followed by addition of the required amount of finely ground $Al_2O_3$ (0.20 g). The heterogeneous mixture is stirred for 10 minutes to assure complete wetting and dispersion of the $Al_2O_3$. After stirring, the addition of 3 g of BP2000 Carbon Black (Cabot) is added and stirred for an additional 10 minutes to assure the carbon black is fully wetted. To the stirring acidic salt, carbon black, and aluminum oxide slurry solution (pH<1), preferably at room temperature or between 25-100° C., was initiated drop wise addition of a 20 wt % NaOH solution (typical addition times are 10-15 minutes), prepared from DI water and NaOH pellets as purchased from Aldrich chemical, until pH 7-8 is attained. After addition of the 20 wt % NaOH solution (typical addition amounts 11-12 g), and attaining target pH, the solution is stirred at room temperature, or at the target precipitation temperature, for an additional 60 minutes. The resulting precipitate is filtered and washed with warm DI water. The filter cake is dried at 140° C. for 2-3 hours, and calcined at 500° C. for 4 h in a muffle furnace. The metal oxides were used directly as prepared.

Heterogeneously catalyzed ethanol to propylene reactions take place in a packed bed of catalyst located inside of a ⅜" OD stainless steel reaction tube. Gaseous reagents are supplied by mass flow controllers and liquid reactants are supplied by syringe pump. The liquid reactants are mixtures of ethanol and water. A co-flow of nitrogen provides an internal standard to quantify gaseous products. Prior to entering the reactor the nitrogen/ethanol/water mixture is effectively vaporized by preheating to 320° C. The flow reactor is enclosed in a heating furnace capable of heating the packed bed to 550° C.

Downstream of the flow reactor, gaseous products are separated from liquid products by a cold trap and both streams are sent to on-line instrumentation for composition analysis.

Product streams are analyzed by gas chromatography (GC). Liquid samples are collected in a cold trap for offline analysis. Gaseous samples are directed to a GC sample loop equipped with a thermal conductivity detector (TCD).

Example 6B

Results with 37% Molar Concentration of Ethanol

Fuel grade Ethanol and water were mixed in a 3:2 ratio by mass. The ethanol-water mixture was fed to the reactor at a rate of 0.08 mL/min over a 24 hr period. A co-feed of nitrogen enables quantification of gaseous products including isobutylene, propylene, $CO_2$, acetone and methane. The total inlet mole concentration of ethanol for the baseline condition is 37.0%. The catalyst temperature is set to 440° C. The stainless steel reactor is loaded with a mixture of 2.5 g of Zn—Zr—Al mixed-metal-oxide catalyst prepared in Example 6A for a co-precipitated catalyst prepared with a 1/11/0.6 Zn/Zr/Al ratio with 2.5 g of glass beads.

The product distribution based on carbon selectivity for the baseline conditions described above is shown in Table 14. The primary product is propylene at 59.1% carbon selectivity. The 59.1% carbon selectivity represents 78.8% of the theoretical maximum. There is 9.8% carbon converted to isobutylene, 22.7% carbon converted to ethylene, 0.8 0.20% carbon converted to acetone, 23.1 22.9% carbon converted to $CO_2$, and the remainder or carbon is converted to methane. Results for the present example indicate improved propylene selectivity at high concentrations of ethanol in the reactor feed.

TABLE 14

Carbon Selectivity in Product for Ethanol to Propylene Experiments at Ethanol Molar Concentration of 37%

| Propylene | $CO_2$ | Ethylene | Isobutylene | Acetone | Methane |
|---|---|---|---|---|---|
| 59.1% | 22.7% | 3.9% | 9.8% | 0.70% | 3.1% |

Example 7

Ethanol to Propylene Conversion Using Co-Precipitated $Zn_xZr_yAl_vSi_sO_z$ Mixed Oxide Catalyst Example 7A Co-Precipitation Catalyst Preparation & Reactor Setup Separately, the required amount of $ZrO(NO_3)_2$ (99%) and $Zn(NO_3)_2 \cdot 6H_2O$ (99.8%) were dissolved in 70 g DI (deionized) water to prepare the stock metal salt solutions to deliver the required Zn/Zr molar ratio. For example, a 1/12 Zn/Zr ratio was prepared by adding 10 g of $ZrO(NO_3)_2$ (99%) and 1.2 g of $Zn(NO_3)_2 \cdot 6H_2O$ (99.8%) to 70 g of DI water. The resulting salt solution is heated until the salts are fully dissolved. The various Zn to Zr molar ratios (1:8, 1:12, 1:20, 1:25, 1:36) were all prepared from these stock solutions. To a 0.5 L round bottom flask equipped with a magnetic stirrer, the appropriate (Zn/Zr) metal salt solution was added followed by addition of the required amount of finely ground Al2O3 (0.40 g), and SiO2 (0.44 g). The heterogeneous mixture is stirred for 10 minutes to assure complete wetting and dispersion of the Al2O3 and SiO2. After stirring, the addition of 3 g of BP2000 Carbon Black (Cabot) is added and stirred for an additional 10 minutes to assure the carbon black is fully wetted. To the stirring acidic salt, carbon black, aluminum oxide, and silicon dioxide slurry solution (pH<1), preferably at room temperature or between 25-100° C., was initiated drop wise addition of a 20 wt % NaOH solution (typical addition times are 10-15 minutes), prepared from DI water and NaOH pellets as purchased from Aldrich chemical, until pH 7-8 is attained. After addition of the 20 wt % NaOH solution (typical addition amounts 11-12 g), and attaining target pH, the solution is stirred at room temperature, or at the target precipitation temperature, for an additional 60 minutes. The resulting precipitate is filtered and washed with warm DI water. The filter cake is dried at 140° C. for 2-3 hours, and calcined at 500° C. for 4 h in a muffle furnace. The metal oxides were used directly as prepared.

Heterogeneously catalyzed ethanol to propylene reactions take place in a packed bed of catalyst located inside of a ⅜" OD stainless steel reaction tube. Gaseous reagents are supplied by mass flow controllers and liquid reactants are supplied by syringe pump. The liquid reactants are mixtures of ethanol and water. A co-flow of nitrogen provides an internal standard to quantify gaseous products. Prior to entering the reactor the nitrogen/ethanol/water mixture is effectively vaporized by preheating to 320° C. The flow reactor is enclosed in a heating furnace capable of heating the packed bed to 550° C.

Downstream of the flow reactor, gaseous products are separated from liquid products by a cold trap and both streams are sent to on-line instrumentation for composition analysis.

Product streams are analyzed by gas chromatography (GC). Liquid samples are collected in a cold trap for offline analysis. Gaseous samples are directed to a GC sample loop equipped with a thermal conductivity detector (TCD).

Example 7B

Results with 37% Molar Concentration of Ethanol

Fuel grade Ethanol and water were mixed in a 3:2 ratio by mass. The ethanol-water mixture was fed to the reactor at a rate of 0.08 mL/min over a 52 hr period. A co-feed of nitrogen enables quantification of gaseous products including isobutylene, propylene, $CO_2$, acetone and methane. The total inlet mole fraction of ethanol for the baseline condition is 37.0%. The catalyst temperature is set to 470° C. The stainless steel reactor is loaded with a mixture of 2.5 g of Zn—Zr—Al—Si mixed-metal-oxide catalyst prepared in Example 1 for a co-precipitated catalyst prepared with a 1/12/2/2 Zn/Zr/Al/Si ratio with 2.5 g of glass beads.

The product distribution based on carbon selectivity for the baseline conditions described above is shown in Table 15. The primary product is propylene at 59.1% carbon selectivity. The 56.6% carbon selectivity represents 75.5% of the theoretical maximum. There is 7.4% carbon converted to isobutylene, 8.7% carbon converted to ethylene, 0.90% carbon converted to acetone, 20.5% carbon converted to $CO_2$, and the remainder or carbon is converted to methane. Results for the present example indicate improved propylene selectivity at high concentrations of ethanol in the reactor feed.

TABLE 15

Carbon Selectivity in Product for Ethanol to Propylene Experiments at Ethanol Molar Concentration of 37%

| Propylene | $CO_2$ | Ethylene | Isobutylene | Acetone | Methane |
|---|---|---|---|---|---|
| 56.6% | 20.5% | 8.7% | 7.4% | 0.90% | 4.5% |

Example 8

Ethanol to Acetone Conversion Using a Co-Precipitated $Zn_xMg_vZr_yO_z$ or $Zn_xCu_vZr_yO_z$ Mixed Oxide Catalyst Example 8A Co-Precipitation $Zn_xMg_vZr_yO_z$ Catalyst Preparation & Reactor Setup Separately, the required amount of $ZrO(NO_3)_2$ (99%) and $Zn(NO_3)_2 \cdot 6H_2O$ (99.8%), and $Mg(OAc)_2 \cdot 4H_2O$ were dissolved in 70 g DI water to prepare the stock metal salt solutions to deliver the required Zn/Mg/Zr molar ratio. For example, a 1/1/25 Zn/Mg/Zr ratio was prepared by adding 10 g of $ZrO(NO_3)_2$ (99%), 0.51 g of $Zn(NO_3)_2 \cdot 6H_2O$ (99.8%), and 0.37 g of $Mg(OAc)_2 \cdot 4H_2O$ to 70 g of DI water. The resulting ternary salt solution is heated until the salts are fully dissolved. To a 0.5 L round bottom flask equipped with a magnetic stirrer, the appropriate metal salt solution was added. To the stirring acidic salt solution (pH<1), at room temperature, was initiated drop wise addition of a 20 wt % NaOH solution (typical addition times are 10-15 minutes), prepared from DI water and NaOH pellets as purchased from Aldrich chemical, until pH 7.0-9.0 is attained. After addition of the 20 wt % NaOH solution (typical addition amounts 11-12 g), and attaining target pH, the solution is stirred at room temperature for an additional 60 minutes. The resulting precipitate is filtered and washed with warm DI water. The filter cake is dried at 140° C. for 3 hours, and calcined at 500° C. for 4 h in a muffle furnace. The ternary metal oxides thus prepared were used directly as prepared.

Heterogeneously catalyzed ethanol to acetone reactions take place in a packed bed of catalyst located inside of a ⅜" OD stainless steel reaction tube. Gaseous reagents are supplied by mass flow controllers and liquid reactants are supplied by syringe pump. The liquid reactants are mixtures of ethanol and water. A co-flow of nitrogen provides an internal standard to quantify gaseous products. Prior to entering the reactor the nitrogen/ethanol/water mixture is effectively vaporized by preheating to 320° C. The flow reactor is enclosed in a heating furnace capable of heating the packed bed to 550° C.

Downstream of the flow reactor, gaseous products are separated from liquid products by a cold trap and both streams are sent to on-line instrumentation for composition analysis.

Product streams are analyzed by gas chromatography (GC). Liquid samples are collected in a cold trap for offline analysis. Gaseous samples are directed to a GC sample loop equipped with a thermal conductivity detector (TCD).

Example 8B

Co-Precipitation $Zn_xCu_vZr_yO_z$ Catalyst Preparation & Reactor Setup

Separately, the required amount of $ZrO(NO_3)_2$ (99%) and $Zn(NO_3)_2 \cdot 6H_2O$ (99.8%), and $Cu(OAc)_2 \cdot H_2O$ were dissolved in 70 g DI water to prepare the stock metal salt solutions to deliver the required Zn/Cu/Zr molar ratio. For example, a 1/1/25 Zn/Cu/Zr ratio was prepared by adding 10 g of $ZrO(NO_3)_2$ (99%), 0.51 g of $Zn(NO_3)_2 \cdot 6H_2O$ (99.8%), and 0.35 g of $Cu(OAc)_2 \cdot H_2O$ to 70 g of DI water. The resulting ternary salt solution is heated until the salts are fully dissolved. To a 0.5 L round bottom flask equipped with a magnetic stirrer, the appropriate metal salt solution was added. To the stirring acidic salt solution (pH<1), at room temperature, was initiated drop wise addition of a 20 wt % NaOH solution (typical addition times are 10-15 minutes), prepared from DI water and NaOH pellets as purchased from Aldrich chemical, until pH 7.0-9.0 is attained. After addition of the 20 wt % NaOH solution (typical addition amounts 11-12 g), and attaining target pH, the solution is stirred at room temperature for an additional 60 minutes. The resulting precipitate is filtered and washed with warm DI water. The filter cake is dried at 140° C. for 3 hours, and calcined at 500° C. for 4 h in a muffle furnace. The ternary metal oxides thus prepared were used directly as prepared.

Heterogeneously catalyzed ethanol to acetone reactions take place in a packed bed of catalyst located inside of a ⅜" OD stainless steel reaction tube. Gaseous reagents are supplied by mass flow controllers and liquid reactants are supplied by syringe pump. The liquid reactants are mixtures of ethanol and water. A co-flow of nitrogen provides an internal standard to quantify gaseous products. Prior to entering the reactor the nitrogen/ethanol/water mixture is effectively vaporized by preheating to 320° C. The flow reactor is enclosed in a heating furnace capable of heating the packed bed to 550° C.

Downstream of the flow reactor, gaseous products are separated from liquid products by a cold trap and both streams are sent to on-line instrumentation for composition analysis.

Product streams are analyzed by gas chromatography (GC). Liquid samples are collected in a cold trap for offline analysis. Gaseous samples are directed to a GC sample loop equipped with a thermal conductivity detector (TCD).

Example 8C

Results with 25.4% Molar Concentration of Ethanol

Ethanol and water were mixed in a 1:1 ratio by mass. The ethanol-water mixture was fed to the reactor at a rate of 0.1 mL/min. A co-feed of nitrogen enables quantification of gaseous products including acetone, isobutylene, propylene, $CO_2$, and methane. The total inlet mole concentration of ethanol for the baseline condition is 25.4%. The catalyst temperature is set to 460° C. The stainless steel reactor is loaded with 2.5 g of Zn—Mg—Zr mixed-metal-oxide catalyst prepared in Example 8A for a co-precipitated catalyst prepared with a 1/1/25 Zn/Mg/Zr ratio.

The product distribution based on carbon selectivity for the baseline conditions described above is shown in Table 16. The primary product is acetone at 65.2% carbon selectivity. The 65.2% carbon selectivity represents 87% of the theoretical maximum. There is 2.1% carbon converted to propylene, 8.5% carbon converted to isobutylene, 20.6% carbon converted to $CO_2$, and the remainder or carbon is converted to methane with non-detectable levels of ethylene. Results for the present example indicate improved acetone selectivity at high concentrations of ethanol in the reactor feed.

TABLE 16

Carbon Selectivity in Product for Ethanol to Isobutylene Experiments at Ethanol Molar Concentration of 25.4%

| $CO_2$ | Ethylene | Propylene | Isobutylene | Acetone | Methane |
|---|---|---|---|---|---|
| 20.6% | 0% | 2.1% | 8.5% | 65.2% | 3.5% |

Example 8D

Results with 25.4% Molar Concentration of Ethanol

Ethanol and water were mixed in a 1:1 ratio by mass. The ethanol-water mixture was fed to the reactor at a rate of 0.1 mL/min. A co-feed of nitrogen enables quantification of gaseous products including acetone, isobutylene, propylene, $CO_2$, and methane. The total inlet mole concentration of ethanol for the baseline condition is 25.4%. The catalyst temperature is set to 460° C. The stainless steel reactor is loaded with 2.5 g of Zn—Cu—Zr mixed-metal-oxide catalyst prepared in Example 8B for a co-precipitated catalyst prepared with a 1/1/25 Zn/Cu/Zr ratio.

The product distribution based on carbon selectivity for the baseline conditions described above is shown in Table 17. The primary product is acetone at 54% carbon selectivity. The 54% carbon selectivity represents 72% of the theoretical maximum. There is 5% carbon converted to propylene, 11.2% carbon converted to isobutylene, 22.0% carbon converted to $CO_2$, and the remainder or carbon is converted to methane with low levels of ethylene. Results for the present example indicate improved acetone selectivity at high concentrations of ethanol in the reactor feed.

TABLE 17

Carbon Selectivity in Product for Ethanol to Isobutylene Experiments at Ethanol Molar Concentration of 25.4%

| $CO_2$ | Ethylene | Propylene | Isobutylene | Acetone | Methane |
|---|---|---|---|---|---|
| 22.0% | 3.6% | 5.0% | 11.2% | 54.0% | 4.2% |

Example 9

Ethanol to Acetone Conversion Using Impregnated $Zn_xMg_yMn_wZr_yO_z$ or $Zn_xCu_vMn_wZr_yO_z$ Mixed Oxide Catalyst Example 9A Impregnated $Zn_xMg_vMn_wZr_yQ_z$ Catalyst Preparation & Reactor Setup Separately, the required amount of $Zn(NO_3)_2.6H_2O$ (99.8%), and $Mg(OAc)_2.4H_2O$ were dissolved in DI water to prepare the stock metal salt solutions to deliver the required Zn/Mg/Mn/Zr molar ratio. For example, a 1/1/4/12 Zn/Mg/Mn/Zr ratio was prepared by adding 0.60 g of $Zn(NO_3)_2.6H_2O$ (99.8%), and 0.43 g of $Mg(OAc)_2.4H_2O$ to 7.8 g of DI water. The resulting binary Zn/Mg salt solution is heated until the salts are fully dissolved. Afterwards, to 6.0 g of a Mn/Zr oxide granulated pellet (as provided by Clariant Corporation), at a Mn/Zr atom ratio of 1/3, is added in dropwise fashion the previously formed Zn/Mg salt solution as per incipient wetness technique in which solids are fully wetted with minimal liquid pooling. The resulting impregnated solid is dried at 140° C. for 3 hours, and calcined at 500° C. for 4 h in a muffle furnace. The quaternary metal oxides thus prepared were used directly as prepared.

Example 9B

Impregnated $Zn_xCu_vMn_wZr_yO_z$ Catalyst Preparation & Reactor Setup

Separately, the required amount of $Zn(NO_3)_2.6H_2O$ (99.8%), and $Cu(OAc)_2.4H_2O$ were dissolved in DI water to prepare the stock metal salt solutions to deliver the required Zn/Cu/Mn/Zr molar ratio. For example, a 1/1/4/12 Zn/Cu/Mn/Zr ratio was prepared by adding 0.60 g of $Zn(NO_3)_2.6H_2O$ (99.8%), and 0.40 g of $Cu(OAc)_2.4H_2O$ to 7.1 g of DI water. The resulting binary Zn/Cu salt solution is heated until the salts are fully dissolved. Afterwards, to 6.0 g of a Mn/Zr oxide granulated pellet (as provided by Clariant Corporation), at a Mn/Zr atom ratio of 1/3, is added in dropwise fashion the previously formed Zn/Cu salt solution as per incipient wetness technique in which solids are fully wetted with minimal liquid pooling. The resulting impregnated solid is dried at 140° C. for 3 hours, and calcined at 500° C. for 4 h in a muffle furnace. The quaternary metal oxides thus prepared were used directly as prepared.

Heterogeneously catalyzed ethanol to acetone reactions take place in a packed bed of catalyst located inside of a ⅜" OD stainless steel reaction tube. Gaseous reagents are supplied by mass flow controllers and liquid reactants are supplied by syringe pump. The liquid reactants are mixtures of ethanol and water. A co-flow of nitrogen provides an internal standard to quantify gaseous products. Prior to entering the reactor the nitrogen/ethanol/water mixture is effectively vaporized by preheating to 320° C. The flow reactor is enclosed in a heating furnace capable of heating the packed bed to 550° C.

Downstream of the flow reactor, gaseous products are separated from liquid products by a cold trap and both streams are sent to on-line instrumentation for composition analysis.

Product streams are analyzed by gas chromatography (GC). Liquid samples are collected in a cold trap for offline analysis. Gaseous samples are directed to a GC sample loop equipped with a thermal conductivity detector (TCD).

Example 9C

Results with 36.6% Molar Concentration of Ethanol

Ethanol and water were mixed in a 3:2 ratio by mass. The ethanol-water mixture was fed to the reactor at a rate of 0.08 mL/min. A co-feed of nitrogen enables quantification of gaseous products including acetone, isobutylene, propylene, CO2, and methane. The total inlet mole concentration of ethanol for the baseline condition is 36.6%. The catalyst temperature is set to 450° C. The stainless steel reactor is loaded with 2.5 g of Zn—Mg—Mn—Zr mixed-metal-oxide catalyst prepared in Example 8A for impregnated catalyst prepared with a 1/1/4/12 Zn/Mg/Mn/Zr ratio.

The product distribution based on carbon selectivity for the baseline conditions described above is shown in Table 18. The primary product is acetone at 65.2% carbon selectivity. The 62.2% carbon selectivity represents 83% of the theoretical maximum. There is 1.4% carbon converted to propylene, 10.1% carbon converted to isobutylene, 20.2% carbon converted to $CO_2$, and the remainder or carbon is converted to methane with non-detectable levels of ethylene. Results for the present example indicate improved acetone selectivity at high concentrations of ethanol in the reactor feed.

TABLE 18

Carbon Selectivity in Product for Ethanol to Isobutylene Experiments at Ethanol Molar Concentration of 36.6%

| $CO_2$ | Ethylene | Propylene | Isobutylene | Acetone | Methane |
|---|---|---|---|---|---|
| 20.2% | 1.1% | 1.4% | 10.1% | 62.2% | 2.4% |

Example 9D

Results with 36.6% Molar Concentration of Ethanol

Ethanol and water were mixed in a 3:2 ratio by mass. The ethanol-water mixture was fed to the reactor at a rate of 0.08 mL/min. A co-feed of nitrogen enables quantification of gaseous products including acetone, isobutylene, propylene, CO2, and methane. The total inlet mole concentration of ethanol for the baseline condition is 36.6%. The catalyst temperature is set to 450° C. The stainless steel reactor is loaded with 2.5 g of Zn—Cu—Mn—Zr mixed-metal-oxide catalyst prepared in Example 8D for impregnated catalyst prepared with a 1/1/4/12 Zn/Cu/Mn/Zr ratio.

The product distribution based on carbon selectivity for the baseline conditions described above is shown in Table 19. The primary product is acetone at 54% carbon selectivity. The 61% carbon selectivity represents 78% of the theoretical maximum. There is 1.4% carbon converted to propylene, 9.5% carbon converted to isobutylene, 19.7% carbon converted to $CO_2$, and the remainder or carbon is converted to methane with low levels of ethylene. Results for the present example indicate improved acetone selectivity at high concentrations of ethanol in the reactor feed.

TABLE 19

Carbon Selectivity in Product for Ethanol to Isobutylene Experiments at Ethanol Molar Concentration of 36.6%

| $CO_2$ | Ethylene | Propylene | Isobutylene | Acetone | Methane |
|---|---|---|---|---|---|
| 19.7% | 1.4% | 1.4% | 9.5% | 61.1% | 2.4% |

Example 10

Ethanol to Lower Olefin Conversion Using a Bifunctional Catalyst

Example 10A

$Ba_xZr_yO_z$ Catalyst Preparation

The purpose of this example is to illustrate the preparation of a bifunctional heterogeneous catalyst comprising acid and base functionality.

Commercial Zirconium Oxide was crushed and sieved in order to produce a nominal particle size of <1 mm and >0.625 mm. The calculated amount (1.0 g) of Barium Acetate (Sigma Aldrich, more than 99% purity) was dissolved in 3.5 grams of deionized water, and added in drop wise fashion by incipient wetness technique to 6 grams of previously classified Zirconium Oxide particles to produce a Zirconium Oxide wetted particle impregnated with Barium Acetate at an elemental molar ratio of 1:12 relative to Barium and Zirconium. The resulting wetted material was allowed to dry overnight at room temperature, followed by calcination at 400° C. for 2 hours and 3 hours at 600° C. to obtain a $Ba_xZr_yO_z$ catalyst.

Example 10B

$Rb_xZr_yO_z$ Catalyst Preparation

The purpose of this example is to illustrate the preparation of another bifunctional heterogeneous catalyst comprising acid and base functionality.

Commercial Zirconium Oxide was crushed and sieved in order to produce a nominal particle size of <1 mm and >0.625 mm. The calculated amount (0.60 g) of Rubidium Acetate (Sigma Aldrich, more than 99% purity) was dissolved in 3.5 grams of deionized water, and added in drop wise fashion by incipient wetness technique to 6 grams of previously classified Zirconium Oxide particles to produce a Zirconium Oxide wetted particle impregnated with Barium Acetate at an elemental molar ratio of 1:12 relative to Barium and Zirconium. The resulting wetted material was allowed to dry overnight at room temperature, followed by calcination at 400° C. for 2 hours and 3 hours at 600° C. to obtain a $Rb_xZr_yO_z$ catalyst.

Example 10C

$Sc_wBa_xZr_yO_z$ Catalyst Preparation

The purpose of this example is to illustrate the preparation of yet another bifunctional heterogeneous catalyst comprising acid and base functionality.

Commercial Zirconium Oxide was crushed and sieved in order to produce a nominal particle size of <1 mm and >0.625 mm. The calculated amount (1.0 g) of Barium Acetate (Sigma Aldrich, more than 99% purity), and Scandium Acetate (0.05 g) as promoter (Sigma Aldrich, more than 99% purity), was dissolved in 3.5 grams of deionized water, and added in drop wise fashion by incipient wetness technique to 6 grams of previously classified Zirconium Oxide particles to produce a Zirconium Oxide wetted particle impregnated with Barium Acetate and 2000 ppm of Scandium Acetate at an elemental molar ratio of 1:12 relative to Barium and Zirconium. The resulting wetted material was allowed to dry overnight at room temperature, followed by calcination at 400° C. for 2 hours and 3 hours at 600° C. to obtain a $Sc_wBa_xZr_yO_z$ catalyst.

The foregoing detailed description has been given for clearness of understanding only and no unnecessary limitations should be understood there from as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The disclosures, including the claims, figures and/or drawings, of each and every patent, patent application, and publication cited herein are hereby incorporated herein by reference in their entireties.

What is claimed is:

1. A process for preparing a functionalized lower hydrocarbon, comprising:
   (a) feeding to a reactor a reactor feed comprising ethanol at a concentration of at least 14 mol %; and
   (b) contacting the ethanol with a mixed oxide catalyst in the reactor, the mixed oxide catalyst having the formula $Zn_xZr_yA_vQ_sMn_wO_z$, whereby the ethanol is converted to at least one functionalized lower hydrocarbon at a yield of at least about 30% of the maximum theoretical molar yield,
   wherein X is 1 to 10,
   wherein Y is 1 to 100,
   wherein A is Al, Si, Mg, or Cu, and V is 0 to 100,
   wherein Q is Al, Si, Mg, or Cu, and S is 0 to 100,
   wherein W is 0 to 30, and
   wherein Z is 5 to 250.

2. The process of claim 1, further comprising step (c) of recovering at least one of the functionalized lower hydrocarbons.

3. The process of claim 2, wherein the functionalized lower hydrocarbon recovered in step (c) is propylene.

4. The process of claim 1, wherein the ethanol is bio-based ethanol.

5. The process of claim 1, wherein ethanol is contacted with the $Zn_xZr_yA_vQ_sMn_wO_z$ mixed oxide catalyst at a temperature falling within the range of about 300° C. to about 600° C.

6. The process of claim 1, wherein the $Zn_xZr_yA_vQ_sMn_wO_z$ mixed oxide catalyst is prepared using a hard-template method, a co-precipitation method, or an impregnated method.

7. The process of claim 6, wherein V is 0, S is 0, and W is 0, and, wherein the ratio of Zn/Zr (x:y) in the $Zn_xZr_yO_z$ mixed oxide catalyst is about 1:12 and is prepared using the hard-template method, and wherein the molar concentration of the ethanol in the reactor feed is about 14.8%, and wherein the functionalized lower hydrocarbon includes isobutylene, propylene, and acetone.

8. The process claim 1, wherein the $Zn_xZr_yA_vQ_sMn_wO_z$ mixed oxide catalyst is regenerated in situ.

9. The process of claim 8, wherein the $Zn_xZr_yA_vQ_sMn_wO_z$ mixed oxide catalyst is regenerated in situ by switching the process feed to an oxygen-rich stream while maintaining catalyst reaction temperatures.

10. A process for preparing a functionalized lower hydrocarbon, comprising:
    (a) feeding to a reactor a reactor feed comprising ethanol at a concentration of at least about 14 mol %: and
    (b) contacting the ethanol with a mixed oxide catalyst in the reactor, the mixed oxide catalyst having the formula $Zn_xZr_yA_vQ_sMn_wO_z$, Whereby the ethanol is converted to at least one functionalized lower hydrocarbon at a yield of at least about 30% of the maximum theoretical molar yield,
    wherein X is 1 to 10,
    wherein Y is 1 to 100,
    wherein A is Al, and V is 1 to 100,
    wherein Q is Al, Si, Mg, or Cu, and S is 0,
    wherein W is 0, and
    wherein Z is 5 to 250.

11. The process of claim 10, wherein the ratio of Zn/Zr/Al (x:y:v) in the $Zn_xZr_yAl_vO_z$ mixed oxide catalyst is from about 1:8:8 to about 1:20:20.

12. The process of claim 10, wherein the ratio of Zn/Zr/Al (x:y:v) in the $Zn_xZr_yAl_vO_z$ mixed oxide catalyst is about 1:12:1.

13. The process of claims 12, wherein the $Zn_xZr_yAl_vO_z$ mixed oxide catalyst is prepared using a co-precipitation method.

14. The process of claim 13, wherein the functionalized lower hydrocarbon is propylene.

15. The process of claim 14, wherein the yield of the propylene is at least about 59% of the maximum theoretical molar yield.

16. The process of claim 12, wherein the molar concentration of the ethanol in the reactor feed is about 37%.

17. A process for preparing a functionalized lower hydrocarbon, comprising:
    (a) feeding to a reactor a reactor feed comprising ethanol at a concentration of at least about 14 mol %: and
    (b) contacting the ethanol with a mixed oxide catalyst in the reactor, the mixed oxide catalyst having the formula $Zn_xZr_yA_vQ_sMn_wO_z$ whereby the ethanol is converted to at least one functionalized lower hydrocarbon at a yield of at least about 30% of the maximum theoretical molar vies d,
    wherein X is 1 to 10,
    wherein Y is 1 to 100,
    wherein A is Al and V is 1 to 100,
    wherein Q is Si and S is 1to 100,
    wherein W is 0, and
    wherein Z is5 to 250.

18. The process of claim 17, wherein the ratio of Zn/Zr/Al/Si (x:y:v:s) in the $Zn_xZr_yAl_vSi_sO_z$ mixed oxide catalyst is from about 1:8:8:8 to about 1:20:20:20.

19. The process of claim 17, wherein the ratio of Zn/Zr/Al/Si (x:y:v:s) in the $Zn_xZr_yAl_vSi_sO_z$ mixed oxide catalyst is about 1:12:2:2.

20. The process of claim 19, wherein the $Zn_xZr_yAl_vSi_sO_z$ mixed oxide catalyst is prepared using a co-precipitation method.

21. The process of claim 20, wherein the functionalized lower hydrocarbon is propylene.

22. The process of claim 21, wherein the yield of the propylene is at least about 70% of the maximum theoretical molar yield.

23. The process of claim 21, wherein the molar concentration of the ethanol in the reactor feed is about 37%.

* * * * *